United States Patent
Adachi et al.

(10) Patent No.: US 9,714,262 B2
(45) Date of Patent: Jul. 25, 2017

(54) COMPOSITION FOR FORMING PASSIVATION LAYER, SEMICONDUCTOR SUBSTRATE HAVING PASSIVATION LAYER, METHOD OF PRODUCING SEMICONDUCTOR SUBSTRATE HAVING PASSIVATION LAYER, PHOTOVOLTAIC CELL ELEMENT, METHOD OF PRODUCING PHOTOVOLTAIC CELL ELEMENT AND PHOTOVOLTAIC CELL

(71) Applicant: Hitachi Chemical Company, Ltd., Tokyo (JP)

(72) Inventors: Shuichiro Adachi, Ibaraki (JP); Masato Yoshida, Ibaraki (JP); Takeshi Nojiri, Ibaraki (JP); Yasushi Kurata, Ibaraki (JP); Tooru Tanaka, Ibaraki (JP); Akihiro Orita, Ibaraki (JP); Tsuyoshi Hayasaka, Ibaraki (JP); Takashi Hattori, Tokyo (JP); Mieko Matsumura, Tokyo (JP); Keiji Watanabe, Tokyo (JP); Masatoshi Morishita, Tokyo (JP); Hirotaka Hamamura, Tokyo (JP)

(73) Assignee: Hitachi Chemical Company, Ltd., Tokyo (JP)

( * ) Notice: Subject to any disclaimer, the term of this patent is extended or adjusted under 35 U.S.C. 154(b) by 0 days.

(21) Appl. No.: 14/414,865

(22) PCT Filed: Jul. 19, 2013

(86) PCT No.: PCT/JP2013/069698
§ 371 (c)(1),
(2) Date: Jan. 14, 2015

(87) PCT Pub. No.: WO2014/014108
PCT Pub. Date: Jan. 23, 2014

(65) Prior Publication Data
US 2015/0166582 A1    Jun. 18, 2015

(30) Foreign Application Priority Data

Jul. 19, 2012  (JP) .................................. 2012-160336
Sep. 28, 2012  (JP) .................................. 2012-218389
(Continued)

(51) Int. Cl.
*H01L 31/0216*    (2014.01)
*C07F 9/00*    (2006.01)
(Continued)

(52) U.S. Cl.
CPC .............. *C07F 9/005* (2013.01); *C07F 5/069* (2013.01); *C07F 7/006* (2013.01);
(Continued)

(58) Field of Classification Search
CPC ........... H01L 31/02168; H01L 31/1868; H01L 31/02013; H01L 31/02161; H01L 31/1864
See application file for complete search history.

(56) References Cited

U.S. PATENT DOCUMENTS 4,328,260 A * 5/1982 Whitehouse ............. C09D 5/32
136/256
4,496,398 A    1/1985 Whitehouse
(Continued)

FOREIGN PATENT DOCUMENTS

CN    1441504    9/2003
JP    A H03-188938    8/1991
(Continued)

OTHER PUBLICATIONS

JP 2000-294817 A online machine translation, translated on Jan. 13, 2016.*
(Continued)

Primary Examiner — Golam Mowla
(74) Attorney, Agent, or Firm — Seyfarth Shaw LLP

(57) ABSTRACT

A composition for forming a passivation layer, comprising a compound represented by Formula (I): $M(OR^1)_m$. In Formula (I), M comprises at least one metal element selected from the group consisting of Nb, Ta, V, Y and Hf, each $R^1$ independently represents an alkyl group having from 1 to 8 carbon atoms or an aryl group having from 6 to 14 carbon atoms, and m represents an integer from 1 to 5.

8 Claims, 10 Drawing Sheets

(30) Foreign Application Priority Data

Jan. 25, 2013 (JP) .................................. 2013-011934
Feb. 28, 2013 (JP) .................................. 2013-040153

(51) Int. Cl.
  *H01L 31/18* (2006.01)
  *C07F 5/06* (2006.01)
  *C07F 7/00* (2006.01)
  *H01L 31/02* (2006.01)

(52) U.S. Cl.
  CPC .. *H01L 31/02013* (2013.01); *H01L 31/02161* (2013.01); *H01L 31/02168* (2013.01); *H01L 31/1864* (2013.01); *H01L 31/1868* (2013.01); *Y02E 10/50* (2013.01); *Y02P 70/521* (2015.11)

(56) References Cited

U.S. PATENT DOCUMENTS

| | | | |
|---|---|---|---|
| 4,830,879 A | 5/1989 | Debsikdar | |
| 5,234,556 A | 8/1993 | Oishi et al. | |
| 5,460,877 A | 10/1995 | Oishi et al. | |
| 5,643,642 A | 7/1997 | Oishi et al. | |
| 5,843,591 A | 12/1998 | Oishi et al. | |
| 5,907,766 A | 5/1999 | Swanson et al. | |
| 6,312,565 B1* | 11/2001 | Misra | C01G 33/00 204/157.5 |
| 6,982,230 B2 | 1/2006 | Cabral, Jr. et al. | |
| 2005/0003085 A1 | 1/2005 | Yonekura et al. | |
| 2010/0275964 A1* | 11/2010 | Kinoshita | H01L 31/022433 136/244 |
| 2012/0248451 A1 | 10/2012 | Sone et al. | |

FOREIGN PATENT DOCUMENTS

| | | |
|---|---|---|
| JP | A 2000-294817 | 10/2000 |
| JP | B 3107287 | 11/2000 |
| JP | A 2004-006565 | 1/2004 |
| JP | A 2004-359532 | 12/2004 |
| JP | A 2008-019285 | 1/2008 |
| JP | B 4767110 | 9/2011 |
| JP | A 2011-216845 | 10/2011 |
| JP | WO2014/014110 | 7/2016 |
| TW | 200503956 | 2/2005 |
| TW | 201308633 | 2/2013 |

OTHER PUBLICATIONS

Hoex B. et al. "On the c-Si Passivation Mechanism by the Negative-Charge-Dielectric $Al_2O_3$" Journal of Applied Physics, vol. 104, pp. 113703-1-113703-7 (2008).

Vitanov P. et al. "Chemical Deposition of $Al_2O_3$ Thin Films on Si Substrates" Thin Solid Films, vol. 517, pp. 6327-6330 (2009).

Xiao Hai-Qing. et al. "Excellent Passivation of p-Type Si Surface by Sol-Gel $Al_2O_3$ Films" Chinese Physics Letters, vol. 26, No. 8, pp. 088102-1-1088102-4 (2009).

First Office Action issued in corresponding Chinese Patent Application No. 201380038209.0 dated Jan. 28, 2016.

Notice of Reasons for Rejection issued in Japanese Patent Application No. 2014-525892, mailed Jan. 10, 2017.

Notification of Reason for Refusal in Taiwanese Patent Application No. 102126031, mailed Jan. 9, 2017.

* cited by examiner

COMPOSITION FOR FORMING PASSIVATION LAYER, SEMICONDUCTOR SUBSTRATE HAVING PASSIVATION LAYER, METHOD OF PRODUCING SEMICONDUCTOR SUBSTRATE HAVING PASSIVATION LAYER, PHOTOVOLTAIC CELL ELEMENT, METHOD OF PRODUCING PHOTOVOLTAIC CELL ELEMENT AND PHOTOVOLTAIC CELL

CROSS-REFERENCE TO RELATED APPLICATION

This application is a United States National Stage Application of PCT International Patent Application No. PCT/JP2013/069698, which was filed Jul. 19, 2013, which claims priority to Japanese Patent Application No. 2012-160336, which was filed Jul. 19, 2012, Japanese Patent Application No. 2012-218389, which was filed Sep. 28, 2012, Japanese Patent Application No. 2013-011934, which was filed on Jan. 25, 2013, and Japanese Patent Application No. 2013-040153, which was filed Feb. 28, 2013, the disclosures of each of which is incorporated herein by reference in their entirety.

TECHNICAL FIELD

The present invention relates to a composition for forming a passivation layer, a semiconductor substrate having a passivation layer, a method of producing a semiconductor substrate having a passivation layer, a photovoltaic cell element, a method of producing a photovoltaic cell element, and a photovoltaic cell.

BACKGROUND ART

A conventional method of producing a silicon photovoltaic cell element is explained.

First, in order to improve efficiency by promoting an optical confinement effect, a p-type silicon substrate having a textured structure formed on its light receiving surface is prepared. Then, the p-type silicon substrate is subjected to treatment in a mixed gas atmosphere of phosphorus oxychloride ($POCl_3$), nitrogen and oxygen at a temperature of from 800° C. to 900° C. for several ten minutes, thereby uniformly forming an n-type diffusion layer. In this method, since phosphorus diffusion is performed using a mixed gas, an n-type diffusion layer is formed not only at a light-receiving surface but also at back and side surfaces. Therefore, side etching is performed in order to remove an n-type diffusion layer formed at side surfaces. In addition, an n-type diffusion layer formed at a back surface needs to be converted into a $p^+$-type diffusion layer. Therefore, an aluminum paste including an aluminum powder and a binder is applied to the entire back surface, and this is subjected to thermal treatment (sintering) in order to convert the n-type diffusion layer to a $p^+$-type diffusion layer and to form an aluminum electrode, thereby obtaining an ohmic contact.

However, an aluminum electrode formed from an aluminum paste has a low electric conductivity. Therefore, an aluminum electrode, which is generally formed on an entire back surface, usually has a thickness of from about 10 µm to 20 µm after the thermal treatment (sintering) in order to reduce the sheet resistance. Furthermore, since there is a great difference between thermal expansion coefficients of silicon and aluminum, a large internal stress is generated in a silicon substrate on which an aluminum electrode is formed during thermal treatment (sintering) and cooling, thereby causing a damage to a crystalline interface, an increase in crystal defect, and warpage.

In order to solve the problems as described above, there is a method of reducing the thickness of the back surface electrode layer by reducing the amount of an aluminum paste to be applied. However, reducing the amount of aluminum to be applied results in insufficient amount of aluminum to diffuse from the surface to the inside of a p-type silicon semiconductor substrate. As a result, a desired BSF (Back Surface Field) effect (effect to enhance collection efficiency of generated carriers by the existence of a $p^+$-type diffusion layer) cannot be achieved and the properties of a photovoltaic cell are deteriorated.

With reference to the above, a point contact method, in which an aluminum paste is applied onto a part of a silicon substrate surface to locally form a $p^+$-type diffusion layer and an aluminum electrode (see, for example, Japanese Patent No. 3107287) is proposed.

In a case of a photovoltaic cell having a point contact structure at a surface opposite to the light-receiving surface (hereinafter, also referred to as a "back surface"), it is necessary to suppress a recombination velocity of minority carriers at a surface other than a region at which the aluminum electrode is formed. As a passivation layer for a back surface used for this purpose, a $SiO_2$ film is suggested (see, for example, Japanese Patent Application Laid-Open (JP-A No. 2004-6565). As a passivation effect achieved by forming a $SiO_2$ film, there is an effect of reducing the surface level density, which causes recombination, by terminating a dangling bond of a silicon atom in a back surface portion of a silicon substrate.

As another method to inhibit recombination of minority carriers, there is a method of reducing a minority carrier density by means of an electric field that generates a fixed charge in the passivation layer. Such a passivation effect is generally referred to as an electrical field effect, and an aluminum oxide ($Al_2O_3$) layer and the like are suggested as a material having a negative fixed charge (see, for example, Japanese Patent No. 4767110).

Such a passivation layer is generally formed by a method such as an ALD (Atomic Layer Deposition) method, a CVD (Chemical Vapor Deposition) method and the like (see, for example, Journal of Applied Physics, 104 (2008), 113703-1 to 113703-7). As a simple method of forming an aluminum oxide film on a semiconductor substrate, a method employing a sol gel process is suggested (see, for example, Thin Solid Films, 517 (2009), 6327-6330, and Chinese Physics Letters, 26 (2009), 088102-1 to 088102-4).

SUMMARY OF THE INVENTION

Since a method described in Journal of Applied Physics, 104 (2008), 113703-1 to 113703-7 includes a complicated process such as vapor deposition, it is sometimes difficult to enhance productivity. A composition to be used for a method of forming a passivation layer described in Thin Solid Films, 517 (2009), 6327-6330, and Chinese Physics Letters, 26 (2009), 088102-1 to 088102-4, may cause a trouble such as gelation over time and have an insufficient storage stability.

The invention has been made in view of the above-described conventional problems, and aims to provide a composition for forming a passivation layer that exhibits an excellent storage stability and enables formation of a passivation layer having an excellent passivation effect by a simple method. In addition, the invention aims to provide a semiconductor substrate having a passivation layer that is obtained by using the composition for forming a passivation layer and is provided with a passivation layer having an excellent passivation effect; a method of producing the semiconductor substrate having a passivation layer; a photovoltaic cell element that exhibits an excellent conversion efficiency; a method of producing the photovoltaic cell element; and a photovoltaic cell.

DESCRIPTION OF EMBODIMENTS

Specific means for solving the above-mentioned problem are as follows.

<1> A composition for forming a passivation layer, comprising a compound represented by the following Formula (I):

$$M(OR^1)_m \quad (I)$$

wherein, in Formula (I), M comprises at least one metal element selected from the group consisting of Nb, Ta, V, Y and Hf, each $R^1$ independently represents an alkyl group having from 1 to 8 carbon atoms or an aryl group having from 6 to 14 carbon atoms, and m represents an integer from 1 to 5.

<2> The composition for forming a passivation layer according to <1>, further comprising a compound represented by the following Formula (II):

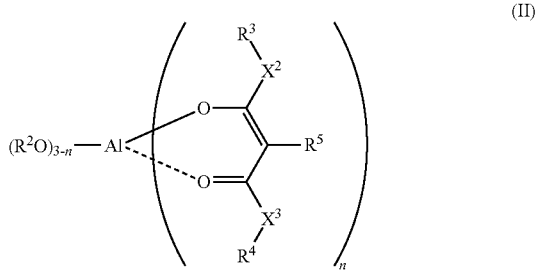

wherein, in Formula (II), each $R^2$ independently represents an alkyl group having from 1 to 8 carbon atoms, n represents an integer from 0 to 3, each of $X^2$ and $X^3$ independently represents an oxygen atom or a methylene group, and each of $R^3$, $R^4$ and $R^5$ independently represents a hydrogen atom or an alkyl group having from 1 to 8 carbon atoms.

<3> The composition for forming a passivation layer according to <1> or <2>, further comprising a liquid medium.

<4> The composition for forming a passivation layer according to any one of <1> to <3>, further comprising a resin.

<5> The composition for forming a passivation layer according to <4>, the composition comprising the liquid medium and the resin, and a total content of the liquid medium and the resin being from 5% by mass to 98% by mass.

<6> The composition for forming a passivation layer according to any one of <2> to <5>, the composition comprising the compound represented by Formula (II), and a total content of the compound represented by Formula (I) and the compound represented by Formula (II) being from 0.1% by mass to 80% by mass.

<7> A semiconductor substrate having a passivation layer, comprising:
a semiconductor substrate; and
a passivation layer that is a thermally-treated product of the composition for forming a passivation layer according to any one of <1> to <6> that is provided at an entire or partial surface of the semiconductor substrate.

<8> A method of producing a semiconductor substrate having a passivation layer, the method comprising:
a process of forming a composition layer by applying the composition for forming a passivation layer according to any one of <1> to <6> on an entire or partial surface of a semiconductor substrate; and
a process of forming a passivation layer by subjecting the composition layer to a thermal treatment.

<9> A photovoltaic cell element, comprising:
a semiconductor substrate having a pn junction of a p-type layer and an n-type layer;
a passivation layer that is a thermally-treated product of the composition for forming a passivation layer according to any one of <1> to <6> and that is provided at an entire or partial surface of the semiconductor substrate; and
an electrode provided at at least one of the p-type layer or the n-type layer.

<10> A method of producing a photovoltaic cell element, the method comprising:
a process of forming a composition layer by applying the composition for forming a passivation layer according to any one of <1> to <6> at an entire or partial surface of a semiconductor substrate having a pn junction of a p-type layer and an n-type layer;
a process of forming a passivation layer by subjecting the composition layer to a thermal treatment; and
a process of forming an electrode at at least one of the p-type layer or the n-type layer.

<11> A photovoltaic cell, comprising:
the photovoltaic cell element according to <9>; and
a wiring material provided on the electrode of the photovoltaic cell element.

Effect of the Invention

According to the invention, it is possible to provide a composition for forming a passivation layer that exhibits an excellent storage stability and enables formation of a passivation layer by a simple method. In addition, it is possible to provide a semiconductor substrate having a passivation layer that is obtained by using the composition for forming a passivation layer and is provided with a passivation layer having an excellent passivation effect; a method of producing the semiconductor substrate having a passivation layer; a photovoltaic cell element that exhibits an excellent conversion efficiency; a method of producing the photovoltaic cell element; and a photovoltaic cell.

EMBODIMENTS FOR IMPLEMENTING THE INVENTION

Figure 1:
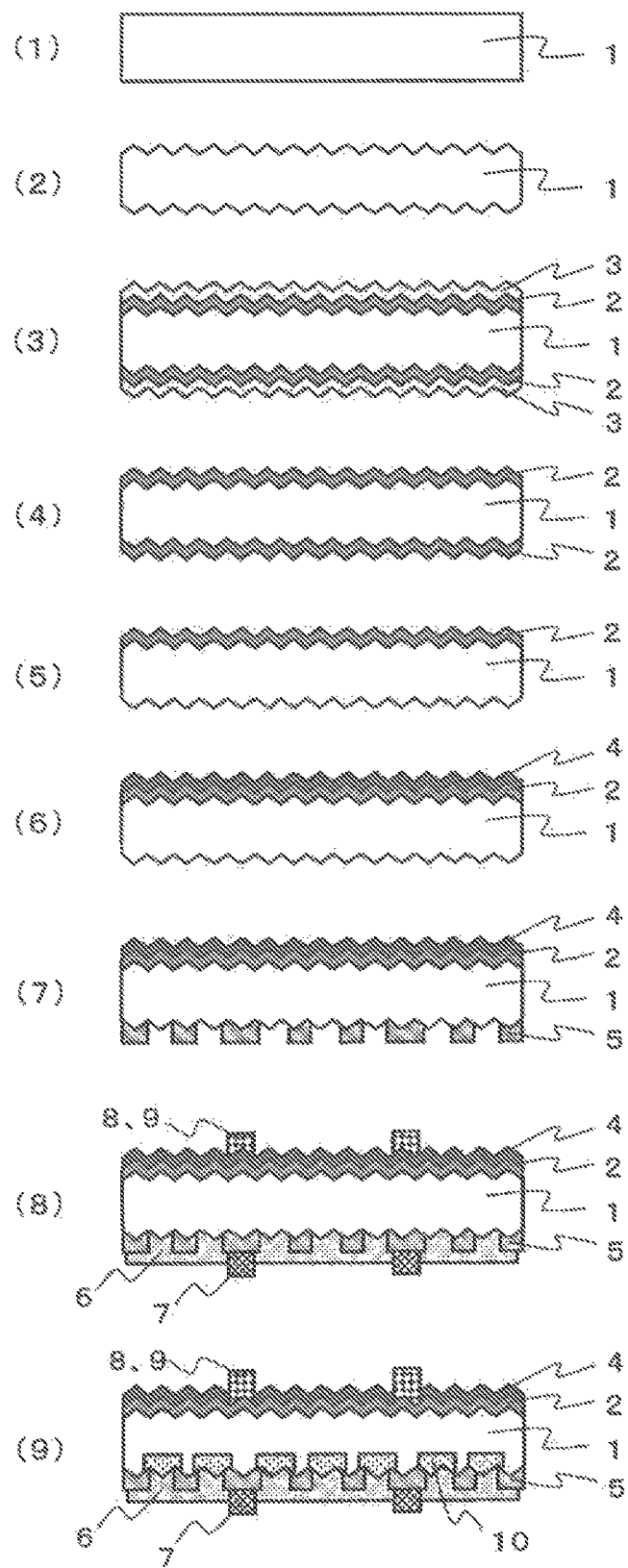
FIG. 1 is a cross sectional view that schematically shows an example of a method of producing a photovoltaic cell element having a passivation layer.

In the present specification, the term "process" as used herein includes not only an independent process but also a process that is not clearly distinguishable from one another, so long as it can attain its object. The numerical value range expressed as "A to B" indicates a range that includes A as a maximum value and B as a minimum value, respectively. Furthermore, unless otherwise indicated, when there are plural kinds of substances that correspond to a component, the content of the component refers to the total contents of the substances. The term "layer" includes a construction having a shape formed on a part of a region, in addition to a construction having a shape formed on an entire region.

<Composition for Forming Passivation Layer>

The composition for forming a passivation layer includes a compound represented by the following Formula (I) (hereinafter, also referred to as a Formula (I) compound). The composition for forming a passivation layer may include other components, if necessary. Since the composition includes the component, it is possible to form a passivation layer having an excellent passivation effect by a simple method. In addition, the composition for forming a passivation layer has an excellent storage stability.

$$M(OR^1)_m \quad (I)$$

In Formula (I), M includes at least one metal element selected from the group consisting of Nb, Ta, V, Y and Hf. $R^1$ represents an alkyl group having from 1 to 8 carbon atoms or an aryl group having from 6 to 14 carbon atoms. m represents an integer from 1 to 5.

In the present specification, a passivation effect of a semiconductor substrate can be evaluated by measuring the effective lifetime of minority carriers in a semiconductor substrate on which a passivation layer is formed, by a microwave reflection photoconductivity decay method with a device such as WT-2000PVN manufactured by Semilab Japan K.K.

Effective lifetime $\tau$ is represented by the following Formula (A) in which $\tau_b$ represents a bulk lifetime inside a semiconductor substrate and $\tau_S$ represents a surface lifetime at a surface of a semiconductor substrate. The smaller the surface level density at a surface of the semiconductor substrate is, the longer the $\tau_S$ is, which results in longer effective lifetime $\tau$. Alternatively, as the defects such as dangling bonds inside the semiconductor substrate decrease, bulk lifetime $\tau_b$ becomes longer, which results in longer effective lifetime $\tau$. That is, measurement of effective lifetime $\tau$ enables evaluation of interfacial properties between the passivation layer and the semiconductor substrate, as well as internal properties of the semiconductor substrate such as dangling bonds.

$$1/\tau = 1/\tau_b + 1/\tau_S \quad (A)$$

The longer the effective lifetime $\tau$ is, the slower the recombination velocity of the minority carriers is. By using a semiconductor substrate having a longer effective lifetime for a photovoltaic cell element, the conversion efficiency thereof is improved.

(Compound Represented by Formula (I))

The composition for forming a passivation layer includes at least one compound represented by Formula (I) (Formula (I) compound). By including at least one kind of Formula (I) compound in the composition for forming a passivation layer, a passivation layer having an excellent passivation effect can be formed. The possible reason for this is as follows.

In a metal oxide, which is formed by performing thermal treatment (sintering) of a composition for forming a passivation layer that includes a Formula (I) compound, it is considered that a fixed charge is readily generated due to defects of metal atoms or oxygen atoms. Further, it is considered that the fixed charge generates a charge near an interface of a semiconductor substrate, thereby reducing the concentration of minority carriers. As a result, it is considered that the recombination velocity of the carriers at the interface is suppressed, and an excellent passivation effect is exhibited.

As for the state of a passivation layer that generates a fixed charge on a semiconductor substrate, its binding mode can be analyzed from a cross section of the semiconductor substrate by electron energy loss spectroscopy (EELS) with a scanning transmission electron microscope (STEM). In addition, a crystalline phase near an interface of a passivation layer can be determined by measuring an X-ray diffraction spectrum (XRD). Also, a fixed charge of a passivation layer can be evaluated by capacitance voltage measurement (CV).

In Formula (I), M includes at least one metal element selected from the group consisting of Nb, Ta, V, Y and Hf. In view of a passivation effect, storage stability of the composition for forming a passivation layer, and operability during the preparation of the composition for forming a passivation layer, M is preferably at least one selected from the group consisting of Nb, Ta and Y, more preferably Nb. In view of obtaining a negative fixed charge density of a passivation layer, M is preferably at least one selected from the group consisting of Nb, Ta, VO and Hf.

In Formula (I), each $R^1$ independently represents an alkyl group having from 1 to 8 carbon atoms or an aryl group having from 6 to 14 carbon atoms, preferably an alkyl group having from 1 to 8 carbon atoms, more preferably an alkyl group having from 1 to 4 carbon atoms. An alkyl group represented by $R^1$ may be straight or branched. Examples of an alkyl group represented by $R^1$ include a methyl group, an ethyl group, a propyl group, an isopropyl group, a butyl group, an isobutyl group, a sec-butyl group, a t-butyl group, a hexyl group, an octyl group, a 2-ethylhexyl group and a 3-ethylhexyl group. Examples of an aryl group represented by $R^1$ include a phenyl group. An alkyl group and an aryl group represented by $R^1$ may have a functional group, and examples of a functional group of an alkyl group include an amino group, a hydroxyl group, a carboxyl group, a sulfonic group and a nitro group. Examples of a functional group of an aryl group include a methyl group, an ethyl group, an isopropyl group, an amino group, a hydroxyl group, a carboxyl group, a sulfonic group and a nitro group.

From the viewpoint of storage stability and a passivation effect, $R^1$ is preferably an unsubstituted alkyl group having from 1 to 8 carbon atoms, more preferably an unsubstituted alkyl group having from 1 to 4 carbon atoms.

In Formula (I), m represents an integer from 1 to 5. From the viewpoint of storage stability, m is preferably 5 when M is Nb, m is preferably 5 when M is Ta, m is preferably 3 when M is VO, m is preferably 3 when M is Y, and m is preferably 4 when M is Hf.

Examples of the compound represented by Formula (I) preferably include a compound in which M is at least one selected from the group consisting of Nb, Ta and Y; $R^1$ is an unsubstituted alkyl group having from 1 to 4 carbon atoms; and m is an integer from 1 to 5.

Examples of the compound represented by Formula (I) preferably include a compound in which M is at least one selected from the group consisting of Nb, Ta, VO and Hf; $R^1$ is an unsubstituted alkyl group having from 1 to 4 carbon atoms; and m is an integer from 1 to 5.

The state of a compound represented by Formula (I) may be solid or liquid. The compound represented by Formula (I) is preferably in a liquid state from the viewpoint of storage stability of the composition for forming a passivation layer, and mixability with a compound represented by Formula (II) as described later, if it is used in combination.

Examples of the compound represented by Formula (I) include niobium methoxide, niobium ethoxide, niobium isopropoxide, niobium n-propoxide, niobium n-butoxide, niobium t-butoxide, niobium isobutoxide, tantalum methoxide, tantalum ethoxide, tantalum isopropoxide, tantalum n-propoxide, tantalum n-butoxide, tantalum t-butoxide, tantalum isobutoxide, yttrium methoxide, yttrium ethoxide, yttrium isopropoxide, yttrium n-propoxide, yttrium n-butoxide, yttrium t-butoxide, yttrium isobutoxide, vanadium methoxide oxide, vanadium ethoxide oxide, vanadium isopropoxide oxide, vanadium n-propoxide oxide, vanadium n-butoxide oxide, vanadium t-butoxide oxide, vanadium isobutoxide oxide, hafnium methoxide, hafnium ethoxide, hafnium isopropoxide, hafnium n-propoxide, hafnium n-butoxide, hafnium t-butoxide and hafnium isobutoxide. Among them, niobium ethoxide, niobium n-propoxide, niobium n-butoxide, tantalum ethoxide, tantalum n-propoxide, tantalum n-butoxide, yttrium isopropoxide and yttrium n-butoxide are preferred. From the viewpoint of obtaining a negative fixed charge density, niobium ethoxide, niobium n-propoxide, niobium n-butoxide, tantalum ethoxide, tantalum n-propoxide, tantalum n-butoxide, vanadium ethoxide oxide, vanadium n-propoxide oxide, vanadium n-butoxide oxide, hafnium ethoxide, hafnium n-propoxide and hafnium n-butoxide are preferred.

As a compound represented by Formula (I), either a prepared product or a commercially available product may be used. Examples of a commercially available product include niobium pentamethoxide, niobium pentaethoxide, niobium penta-i-propoxide, niobium penta-n-propoxide, niobium penta-i-butoxide, niobium penta-n-butoxide, niobium penta-sec-butoxide, tantalum pentamethoxide, tantalum pentaethoxide, tantalum penta-i-propoxide, tantalum penta-n-propoxide, tantalum penta-i-butoxide, tantalum penta-n-butoxide, tantalum penta-sec-butoxide, tantalum penta-t-butoxide, vanadium (V) trimethoxide oxide, vanadium (V) triethoxide oxide, vanadium (V) tri-i-propoxide oxide, vanadium (V) tri-n-propoxide oxide, vanadium (V) tri-i-butoxide oxide, vanadium (V) tri-n-butoxide oxide, vanadium (V) tri-sec-butoxide oxide, vanadium (V) tri-t-butoxide oxide, yttrium tri-i-propoxide, yttrium tri-n-butoxide, hafnium tetramethoxide, hafnium tetraethoxide, hafnium tetra-i-propoxide and hafnium tetra-t-butoxide, manufactured by Kojundo Chemical Lab. Co., Ltd.; niobium pentaethoxide, tantalum pentaethoxide, tantalum pentabutoxide, yttrium-n-butoxide, hafnium-tert-butoxide, manufactured by Hokko Chemical Industry Co., Ltd.; vanadium oxy triethoxide, vanadium oxy tri-normal-propoxide, vanadium oxy tri-normal-butoxide, vanadium oxy tri-iso-butoxide, and vanadium oxy tri-secondary-butoxide, manufactured by Nichia Corporation.

In order to prepare a compound represented by Formula (I), a known method such as a method in which a halide of a specific metal (M) and an alcohol are reacted in the presence of an inert organic solvent, and an ammonia or an amine compound is further added to withdraw a halogen (see JP-A No. 63-227593 and JP-A No. H03-291247) can be used.

The compound represented by Formula (I) may be a compound having a chelate structure formed by mixing with a compound of a specific structure having two carbonyl groups as described below. The number of carbonyl groups to chelate is not particularly limited, and preferably from 1 to 5 when M is Nb, preferably 1 to 5 when M is Ta, preferably 1 to 3 when M is V, preferably from 1 to 3 when M is Y, and preferably from 1 to 4 when M is Hf.

The presence of a chelate structure in a compound represented by Formula (I) can be confirmed by a conventional analysis method. For example, it is confirmed by analyzing infrared spectroscopy spectra, nuclear magnetic resonance spectra, a melting point, or the like.

The content of Formula (I) compound in the composition for forming a passivation layer may be appropriately selected, if necessary. From the viewpoint of storage stability and a passivation effect, the content of Formula (I) compound may be from 0.1% by mass to 80% by mass, preferably from 0.5% by mass to 70% by mass, more preferably from 1% by mass to 60% by mass, still more preferably from 1% by mass to 50% by mass, in the composition for forming a passivation layer.

Compound Represented by Formula (II))

The composition for forming a passivation layer of the invention may include at least one of a compound represented by the following Formula (II) (hereinafter, also referred to as an "organic aluminum compound").

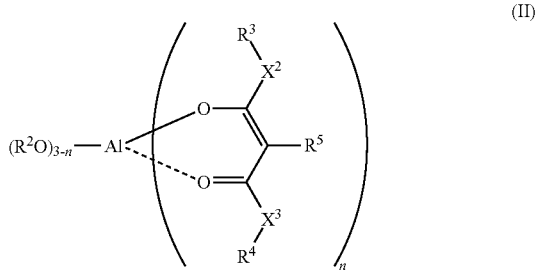

(II)

In Formula (II), each $R^2$ independently represents an alkyl group having from 1 to 8 carbon atoms. n represents an integer from 0 to 3. Each of $X^2$ and $X^3$ independently represents an oxygen atom or a methylene group. Each of $R^3$, $R^4$ and $R^5$ independently represents a hydrogen atom or an alkyl group having from 1 to 8 carbon atoms.

By including the organic aluminum compound as described above in the composition for forming a passivation layer, a passivation effect can be further improved. A possible reason for this is as follows.

The organic aluminum compound includes a compound that is referred to as aluminum alkoxide, aluminum chelate, or the like, and preferably includes an aluminum chelate structure in addition to an aluminum alkoxide structure. As described in Nippon Seramikkusu Kyokai Gakujitsu Ronbunshi, 97 (1989), 369-399, an organic aluminum compound is converted to an aluminum oxide ($Al_2O_3$) by thermal treatment (sintering). In that case, it is considered that the formed aluminum oxide tends to become amorphous, and a 4-fold coordinated aluminum oxide layer tends to be formed near the interface with a semiconductor substrate, and a large negative fixed charge attributed to a 4-fold coordinated aluminum oxide tends to be obtained. In that case, it is considered that complexation with an oxide derived from the Formula (I) compound having a fixed charge is achieved, and a passivation layer having an excellent passivation effect is formed.

In addition to the above, it is considered that a passivation effect is further improved in a passivation layer due to the act of the compounds represented by Formula (I) and Formula (II), respectively. Moreover, by performing thermal treatment (sintering) to a compound represented by Formula (I) and a compound represented by Formula (II) in a mixed state, it is considered that a complex metal alkoxide of a metal (M) represented by Formula (I) and aluminum (Al) is formed and physical properties such as reactivity and vapor pressure are improved. As a result, it is considered that the passivation layer as a thermally-treated (sintered) product becomes denser and its passivation effect is further improved.

In Formula (II), each $R^2$ independently represents an alkyl group having from 1 to 8 carbon atoms, preferably an alkyl group having from 1 to 4 carbon atoms. An alkyl group represented by $R^2$ may be straight or branched. Examples of an alkyl group represented by $R^2$ include a methyl group, an ethyl group, a propyl group, an isopropyl group, a butyl group, an isobutyl group, a sec-butyl group, a t-butyl group, a hexyl group, an octyl group, a 2-ethylhexyl group, a 3-ethylhexyl group. From the viewpoint of storage stability and a passivation effect, an alkyl group represented by $R^2$ is preferably an unsubstituted alkyl group having from 1 to 8 carbon atoms, more preferably an unsubstituted alkyl group having from 1 to 4 carbon atoms.

In Formula (II), n represents an integer from 0 to 3. From the viewpoint of storage stability, n is preferably an integer from 1 to 3, more preferably 1 or 3. Each of $X^2$ and $X^3$ independently represents an oxygen atom or a methylene group. From the viewpoint of storage stability, at least one of $X^2$ and $X^3$ is preferably an oxygen atom.

Each of $R^3$, $R^4$ and $R^5$ in Formula (II) independently represents a hydrogen atom or an alkyl group having from 1 to 8 carbon atoms. An alkyl group represented by $R^3$, $R^4$ and $R^5$ may be straight or branched. An alkyl group represented by $R^3$, $R^4$ and $R^5$ may have a substituent, or may be unsubstituted, and is preferably unsubstituted. Examples of an alkyl group represented by $R^3$, $R^4$ and $R^5$ include an alkyl group having from 1 to 8 carbon atoms, preferably an alkyl group having from 1 to 4 carbon atoms. Examples of an alkyl group represented by $R^3$, $R^4$ and $R^5$ include a methyl group, an ethyl group, a propyl group, an isopropyl group, a butyl group, an isobutyl group, a sec-butyl group, a t-butyl group, a hexyl group, an octyl group and an ethylhexyl group.

From the viewpoint of storage stability and a passivation effect, it is preferred that each of $R^3$ and $R^4$ in Formula (II) independently represents a hydrogen atom or an unsubstituted alkyl group having from 1 to 8 carbon atoms, more preferably a hydrogen atom or an unsubstituted alkyl group having from 1 to 4 carbon atoms.

From the viewpoint of storage stability and a passivation effect, $R^5$ in Formula (II) is preferably a hydrogen atom or an unsubstituted alkyl group having from 1 to 8 carbon atoms, more preferably a hydrogen atom or an unsubstituted alkyl group having from 1 to 4 carbon atoms.

From the viewpoint of storage stability, the compound represented by Formula (II) is preferably a compound in which n is from 1 to 3, and each $R^5$ independently represents a hydrogen atom or an alkyl group having from 1 to 4 carbon atoms.

From the viewpoint of storage stability and a passivation effect, the compound represented by Formula (II) is preferably at least one selected from the group consisting of: a compound in which n is 0 and each $R^2$ independently represents an alkyl group having from 1 to 4 carbon atoms; and a compound in which n is from 1 to 3, each $R^2$ independently represents an alkyl group having from 1 to 4 carbon atoms, at least one of $X^2$ and $X^3$ is an oxygen atom, each of $R^3$ and $R^4$ independently represents a hydrogen atom or an alkyl group having from 1 to 4 carbon atoms, and each $R^5$ is independently a hydrogen atom or an alkyl group having from 1 to 4 carbon atoms.

More preferably, the compound represented by Formula (II) is at least one selected from the group consisting of: a compound in which n is 0 and each $R^2$ is independently an unsubstituted alkyl group having from 1 to 4 carbon atoms; and a compound in which n is from 1 to 3, each $R^2$ independently represents an unsubstituted alkyl group having from 1 to 4 carbon atoms, at least one of $X^2$ and $X^3$ is an oxygen atom, $R^3$ or $R^4$ that is bonded to this oxygen atom is an alkyl group having from 1 to 4 carbon atoms, wherein when $X^2$ or $X^3$ is a methylene group, $R^3$ or $R^4$ that is bonded to the methylene group is a hydrogen atom, and $R^5$ is a hydrogen atom.

Examples of an aluminum trialkoxide, which is an organic aluminum compound represented by Formula (II) in which n is 0, include aluminum trimethoxide, aluminum triethoxide, aluminum triisopropoxide, aluminum tri-sec-butoxide, aluminum mono-sec-butoxy-diisopropoxide, aluminum tri-t-butoxide and aluminum tri-n-butoxide.

Examples of an organic aluminum compound represented by Formula (II) in which n is from 1 to 3 include aluminum ethyl acetoacetate diisopropylate and tri(ethyl acetoacetate) aluminum.

The organic aluminum compound represented by Formula (II) in which n is from 1 to 3 may be a prepared product or a commercially available product. Examples of the commercially available product include ALCH, ALCH-50F, ALCH-75, ALCH-TR and ALCH-TR-20 (all trade names) manufactured by Kawaken Fine Chemicals Co., Ltd.

An organic aluminum compound represented by Formula (II) in which n is from 1 to 3 can be prepared by mixing an aluminum trialkoxide with a compound of a specific structure having two carbonyl groups. Alternatively, a commercially available aluminum chelate compound may be used.

When an aluminum trialkoxide is mixed with a compound of a specific structure having two carbonyl groups, at least some of alkoxide groups in the aluminum trialkoxide is substituted with the compound of a specific structure to form an aluminum chelate structure. If necessary, a liquid medium may exist, and thermal treatment, addition of a catalyst, or the like may be performed. When at least a part of the aluminum alkoxide structure is substituted with an aluminum chelate structure, stability of the organic aluminum compound against hydrolysis and polymerization reaction is improved, and storage stability of the composition for forming a passivation layer is further improved.

From the viewpoint of reactivity and storage stability, the compound of a specific structure having two carbonyl groups is preferably at least one selected from the group consisting of a β-diketone compound, a β-keto ester compound and a malonic diester.

Examples of a β-diketone compound include acetylacetone, 3-methyl-2,4-pentanedione, 2,3-pentanedione, 3-ethyl-2,4-pentanedione, 3-butyl-2,4-pentanedione, 2,2,6,6-tetramethyl-3,5-heptanedione, 2,6-dimethyl-3,5-heptanedione and 6-methyl-2,4-heptanedione.

Examples of a β-keto ester compound include methyl acetoacetate, ethyl acetoacetate, propyl acetoacetate, isopropyl acetoacetate, isobutyl acetoacetate, butyl acetoacetate, t-butyl acetoacetate, pentyl acetoacetate, isopentyl acetoacetate, hexyl acetoacetate, n-octyl acetoacetate, heptyl acetoacetate, 3-pentyl acetoacetate, ethyl 2-acetylheptanoate, ethyl 2-methylacetoacetate, ethyl 2-butylacetoacetate, ethyl hexylacetoacetate, ethyl 4,4-dimethyl-3-oxovarelate, ethyl 4-methyl-3-oxovarelate, ethyl 2-ethylacetoacetate, methyl 4-methyl-3-oxovarelate, ethyl 3-oxohexanoate, ethyl 3-oxovarelate, methyl 3-oxovarelate, methyl 3-oxohexanoate, ethyl 3-oxoheptanoate, methyl 3-oxoheptanoate and methyl 4,4-dimethyl-3-oxovarelate.

Examples of a malonic diester typically include dimethyl malonate, diethyl malonate, dipropyl malonate, diisopropyl malonate, dibutyl malonate, di-t-butyl malonate, dihexyl malonate, t-butylethyl malonate, diethyl methylmalonate, diethyl ethylmalonate, diethyl isopropylmalonate, diethyl butylmalonate, diethyl sec-butylmalonate, diethyl isobutylmalonate and diethyl 1-methylbutylmalonate.

When the organic aluminum compound has an aluminum chelate structure, the number of the aluminum chelate structure is not particularly limited so long as it falls within the range of from 1 to 3. In particular, from the viewpoint of storage stability, it is preferably 1 or 3, and from the viewpoint of solubility, it is more preferably 1. The number of an aluminum chelate structure can be controlled by appropriately adjusting the mixing ratio of an aluminum trialkoxide and a compound of a specific structure having two carbonyl groups. Alternatively, a compound having a desired structure may be selected from the commercially available aluminum chelate compounds.

From the viewpoint of a passivation effect and compatibility with a solvent that may be optionally included in the composition, the compound represented by Formula (II) is specifically preferably at least one selected from the group consisting of aluminum ethylacetoacetate diisopropylate and aluminum triisopropoxide, more preferably aluminum ethylacetoacetate diisopropylate.

The presence of an aluminum chelate structure in an organic aluminum compound can be confirmed by the conventionally used analysis method. For example, it can be confirmed by analyzing infrared spectroscopy spectra, nuclear magnetic resonance spectra, a melting point, or the like.

The organic aluminum compound may be liquid or solid, and is not particularly limited. From the viewpoint of a passivation effect and storage stability, an organic aluminum compound that exhibits favorable stability at an ambient temperature (25° C.) and favorable solubility or dispersibility in a solvent may be used to further improve homogeneity of the formed passivation layer, thereby stably providing a desired passivation effect.

When the composition for forming a passivation layer includes an organic aluminum compound, the content thereof is not particularly limited. In particular, the content of the organic aluminum compound is preferably 0.1% by mass or more and 80% by mass or less, more preferably 0.5% by mass or more and 80% by mass or less, still more preferably 1% by mass or more and 75% by mass or less, particularly preferably 2% by mass or more and 70% by mass or less, and extremely preferably 3% by mass or more and 70% by mass or less, provided that the total content of the Formula (I) compound and the organic aluminum compound is 100% by mass.

When the content of the organic aluminum compound is 0.1% by mass or more, storage stability of the composition for forming a passivation layer tends to be improved. When the content of the organic aluminum compound is 80% by mass or less, the passivation effect tends to be improved.

When the composition for forming a passivation layer includes an organic aluminum compound, the content of the organic aluminum compound in the composition for forming a passivation layer may be appropriately selected. From the viewpoint of storage stability and a passivation effect, the content of the organic aluminum compound in the composition for forming a passivation layer may be from 0.1% by mass to 60% by mass, preferably from 0.5% by mass to 55% by mass, more preferably from 1% by mass to 50% by mass, still more preferably from 1% by mass to 45% by mass.

(Liquid Medium)

The composition for forming a passivation layer may include a liquid medium (a solvent or a dispersion medium). By including a liquid medium in the composition for forming a passivation layer, adjustment of the viscosity becomes easier and applicability improves, thereby enabling formation of a more uniform passivation layer. The liquid medium is not particularly limited, and appropriately selected. In particular, the solvent is preferably a liquid medium that can dissolve a compound represented by Formula (I) and a compound represented by Formula (II) that is optionally added, more preferably includes at least one kind of organic solvent. A liquid medium refers to a medium that is in a liquid state at room temperature (25° C.).

Examples of a liquid medium typically include a ketone solvent such as acetone, methyl ethyl ketone, methyl-n-propyl ketone, methyl isopropyl ketone, methyl-n-butyl ketone, methyl isobutyl ketone, methyl-n-pentyl ketone, methyl-n-hexyl ketone, diethyl ketone, dipropyl ketone, diisobutyl ketone, trimethyl nonanone, cyclohexanone, cyclopentanone, methyl cyclohexanone, 2,4-pentanedione and acetonitrile acetone; an ether solvent such as diethyl ether, methyl ethyl ether, methyl-n-propyl ether, diisopropyl ether, tetrahydrofuran, methyl tetrahydrofuran, dioxane, dimethyl dioxane, ethyleneglycol dimethyl ether, ethyleneglycol diethyl ether, ethyleneglycol di-n-propyl ether, ethyleneglycol dibutyl ether, diethyleneglycol dimethyl ether, diethyleneglycol diethyl ether, diethyleneglycol methyl ethyl ether, diethyleneglycol methyl-n-propyl ether, diethyleneglycol methyl-n-butyl ether, diethyleneglycol di-n-propyl ether, diethyleneglycol di-n-butyl ether, diethyleneglycol methyl-n-hexyl ether, triethyleneglycol dimethyl ether, triethyleneglycol diethyl ether, triethyleneglycol methyl ethyl ether, triethyleneglycol methyl-n-butyl ether, triethyleneglycol di-n-butyl ether, triethyleneglycol methyl-n-hexyl ether, tetraethyleneglycol dimethyl ether, tetraethyleneglycol diethyl ether, tetraethyleneglycol methyl ethyl ether, tetraethyleneglycol methyl-n-butyl ether, tetraethyleneglycol di-n-butyl ether, tetraethyleneglycol methyl-n-hexyl ether, tetraethyleneglycol di-n-butyl ether, propyleneglycol dimethyl ether, propyleneglycol diethyl ether, propyleneglycol di-n-propyl ether, propyleneglycol dibutyl ether, dipropyleneglycol dimethyl ether, dipropyleneglycol diether ether, dipropyleneglycol methyl ethyl ether, dipropyleneglycol methyl-n-butyl ether, dipropyleneglycol di-n-propyl ether, dipropyleneglycol di-n-butyl ether, dipropyleneglycol methyl-n-hexyl ether, tripropyleneglycol dimethyl ether, tripropyleneglycol diethyl ether, tripropyleneglycol methyl ethyl ether, tripropyleneglycol methyl-n-butyl ether, tripropyleneglycol di-n-butyl ether, tripropyleneglycol methyl-n-hexyl ether, tetrapropyleneglycol dimethyl ether, tetrapropyleneglycol diethyl ether, tetrapropyleneglycol methyl ethyl ether, tetrapropyleneglycol methyl-n-butyl ether, tetrapropyleneglycol di-n-butyl ether, tetrapropyleneglycol methyl-n-hexyl ether and tetrapropyleneglycol di-n-butyl ether; an ester solvent such as methyl acetate, ethyl acetate, n-propyl acetate, isopropyl acetate, n-butyl acetate, isobutyl acetate, sec-butyl acetate, n-pentyl acetate, sec-pentyl acetate, 3-methoxybutyl acetate, methylpentyl acetate, 2-ethylbutyl acetate, 2-ethylhexyl acetate, 2-(2-butoxyethoxy)ethyl acetate, benzyl acetate, cyclohexyl acetate, methylcyclohexyl acetate, nonyl acetate, methyl acetoacetate, ethyl acetoacetate, diethyleneglycol methyl ether acetate, diethyleneglycol monoethyl ether acetate, dipropyleneglycol methyl ether acetate, dipropyleneglycol ethyl ether acetate, glycol diacetate, methoxytriethyleneglycol acetate, isoamyl acetate, ethyl propionate, n-butyl propionate, isoamyl propionate, diethyl oxalate, di-n-butyl oxalate, methyl lactate, ethyl lactate, n-butyl lactate, n-amyl lactate, ethyleneglycol methyl ether propionate, ethyleneglycol ethyl ether propionate, ethyleneglycol methyl ether acetate, ethyleneglycol ethyl ether acetate, propyleneglycol methyl ether acetate, propyleneglycol ethyl ether acetate, propyleneglycol propyl ether acetate, γ-butyrolactone and γ-valerolactone; an aprotic polar solvent such as acetonitrile, N-methyl pyrrolidinone, N-ethyl pyrrolidinone, N-propyl pyrrolidinone, N-butyl pyrrolidinone, N-hexyl pyrrolidinone, N-cyclohexyl pyrrolidinone, N,N-dimethyl formamide, N,N-dimethyl acetoamide and dimethyl sulfoxide; a hydrophobic organic solvent such as methylene chloride, chloroform, dichloroethane, benzene, toluene, xylene, hexane, octane, dichlorobenzene, 2-ethylhexanoic acid, methyl isobutyl ketone and methyl ethyl ketone; an alcoholic solvent such as methanol, ethanol, n-propanol, isopropanol, n-butanol, isobutanol, sec-butanol, t-butanol, n-pentanol, isopentanol, 2-methyl butanol, sec-pentanol, t-pentanol, 3-methoxybutanol, n-hexanol, 2-methylpentanol, sec-hexanol, 2-ethylbutanol, sec-heptanol, n-octanol, 2-ethylhexanol, sec-octanol, n-nonylalcohol, n-decanol, sec-undecylalcohol, trimethylnonylalcohol, sec-tetradecylalcohol, sec-heptadecylalcohol, cyclohexanol, methylcyclohexanol, benzylalcohol, ethyleneglycol, 1,2-propyleneglycol, 1,3-butyleneglycol, diethyleneglycol, dipropyleneglycol, triethyleneglycol and tripropyleneglycol; a glycol monoether solvent such as ethyleneglycol monomethyl ether, ethyleneglycol monoethyl ether, ethyleneglycol monophenylether, diethyleneglycol monomethyl ether, diethyleneglycol monoethyl ether, diethyleneglycol mono-n-butyl ether, diethyleneglycol mono-n-hexyl ether, ethoxytriglycol, tetraethyleneglycol mono-n-butyl ether, propyleneglycol monomethyl ether, dipropyleneglycol monomethyl ether, dipropyleneglycol monoethyl ether and tripropyleneglycol monomethyl ether; a terpene solvent such as terpinene, terpineol, myrcene, alloocimene, limonene, dipentene, pinene, carvone, ocimene and phellandrene; and water. These liquid media may be used singly or in a combination of two or more kinds.

In particular, from the viewpoint of applicability with respect to a semiconductor substrate and pattern formability, a liquid medium preferably includes at least one selected from the group consisting of a terpene solvent, an ester solvent and an alcohol solvent, more preferably includes at least one selected from the group consisting of a terpene solvent.

When the composition for forming a passivation layer includes a liquid medium, the content of the liquid medium is determined in view of applicability, pattern formability and storage stability. For example, from the viewpoint of applicability and pattern formability, the content of the liquid medium in the composition for forming a passivation layer is preferably from 5% by mass to 98% by mass, more preferably from 10% by mass to 95% by mass.

(Resin)

The composition for forming a passivation layer may further include at least one kind of resin. By including a resin, morphological stability of a composition layer that is formed by applying the composition for forming a passivation layer on a semiconductor substrate is further improved, and a passivation layer can be formed in a desired shape at a region at which the composition layer has been formed.

The type of the resin is not particularly limited. A preferred resin is easy to adjust its viscosity to a range in which a favorable pattern can be formed upon application of the composition for forming a passivation layer on a semiconductor substrate. Examples of the resin include polyvinyl alcohol, polyacrylamide, a polyacrylamide derivative, polyvinyl amide, a polyvinyl amide derivative, polyvinyl pyrrolidone, polyethylene oxide, a polyethylene oxide derivative, polysulfonic acid, polyacrylamide alkylsulfonic acid, cellulose, a cellulose derivative (cellulose ether such as carboxymethyl cellulose, hydroxyethyl cellulose and ethyl cellulose), gelatin, a gelatin derivative, starch, a starch derivative, sodium alginate, a sodium alginate derivative, xanthan, a xanthan derivative, guar gum, a guar gum derivative, scleroglucan, a scleroglucan derivative, tragacanth, a tragacanth derivative, dextrin, a dextrin derivative, a (meth) acrylic acid resin, a (meth)acrylate resin (such as an alkyl (meth)acrylate resin and a dimentylaminoethyl (meth)acrylate resin), a butadiene resin, a styrene resin, a siloxane resin, and a copolymer of these resins. These resins may be used singly or a combination of two or more kinds.

In the present specification, "(meth)acrylic acid" refers to at least one of "acrylic acid" and "methacrylic acid", and "(meth)acrylate" refers to at least one of "acrylate" and "methacrylate".

Among these resins, it is preferred to use a neutral resin that does not have either an acidic functional group or a basic functional group, from the viewpoint of storage stability and pattern formability. It is more preferred to use a cellulose derivative, because a cellulose derivative is easy to adjust its viscosity and thixotropic property even with a small amount.

The molecular weight of the resin is not particularly limited, and is appropriately adjusted in view of a desired viscosity for the composition for forming a passivation layer. The weight average molecular weight of the resin is preferably from 1,000 to 10,000,000, more preferably from 1,000 to 5,000,000, from the viewpoint of storage stability and pattern formability. The weight average molecular weight of a resin can be calculated from a calibration curve of a standard polystyrene, from a molecular weight distribution measured by GPC (gel permeation chromatography). The calibration curve is approximated by third degree equation using five sets of standard polystyrene samples (PStQuick MP-H, PStQuick B [TOSOH CORPORATION, trade name]). The measurement conditions of GPC are shown below.

Apparatus:
(Pump: Model L-2130 [Hitachi High-Technologies Corporation])
(Detector: Model L-2490 RI [Hitachi High-Technologies Corporation])
(Column oven: L-2350 [Hitachi High-Technologies Corporation])
Column:
Gelpack GL-R440+Gelpack GL-R450+Gelpack GL-R400M (3 columns in total)
(Hitachi Chemical Company, Ltd., trade name)
Column size: 10.7 mm (inner diameter)×300 mm
Eluent: tetrahydrofuran
Sample Concentration: 10 mg/2 mL
Injected Amount: 200 μL
Flow Rate: 2.05 mL/min.
Measurement Temperature: 25° C.

When the composition for forming a passivation layer includes a resin, the content of the resin in the composition for forming a passivation layer may be appropriately selected, if necessary. For example, the content of the resin is preferably from 0.1% by mass to 50% by mass in the total mass of the composition for forming a passivation layer. In order to develop the thixotropic property so that pattern formation is readily performed, the content of the resin is more preferably from 0.2% by mass to 25% by mass, still more preferably from 0.5% by mass to 20% by mass, particularly preferably from 0.5% by mass to 15% by mass.

(Other Components)

The composition for forming a passivation layer of the invention may further include other components that are generally used in the art, if necessary, in addition to the above described components.

The composition for forming a passivation layer may include an acidic compound or a basic compound. When the composition for forming a passivation layer includes an acidic compound or a basic compound, from the viewpoint of storage stability, the content of the acidic compound or the basic compound is preferably 1% by mass or less, more preferably 0.1% by mass or less, respectively, in the composition for forming a passivation layer.

Examples of an acidic compound include a Bronsted acid and a Lewis acid. Specific examples include an inorganic acid such as hydrochloric acid and nitric acid, and an organic acid such as acetic acid. Examples of the basic compound include a Bronsted base and a Lewis base. Specific examples include an inorganic base such as an alkali metal hydroxide and an alkaline earth metal hydroxide, and an organic base such as trialkylamine and pyridine.

Examples of the other components include, for example, a plasticizer, a dispersant, a surfactant, a thixotropic agent, an inorganic filler, other metal alkoxide compounds, and high-boiling point materials. In particular, the composition for forming a passivation layer preferably includes at least one selected from a thixotropic agent and an inorganic filler. By including at least one selected from a thixotropic agent and an inorganic filler, morphological stability of a composition layer that is formed by applying the composition for forming a passivation layer on a semiconductor substrate is further improved, and a passivation layer can be formed in a desired shape at a region at which the composition layer has been formed.

Examples of a thixotropic agent include a fatty acid amide, a polyalkylene glycol compound, and an organic filler. Examples of a polyalkylene glycol compound include a compound represented by the following Formula (III).

$$R^6-(O-R^8)_n-O-R^7 \quad (III)$$

In Formula (III), each of $R^6$ and $R^7$ independently represents a hydrogen atom or an alkyl group, $R^8$ represents an alkylene group. n is an integer of 3 or more. In $(O-R^8)$, three or more of $R^8$ may be the same or different from each other.

Examples of a fatty acid amide include a compound represented by the following Formulae (1), (2), (3) and (4).

$$R^9CONH_2 \quad (1)$$

$$R^9CONH-R^{10}-NHCOR^9 \quad (2)$$

$$R^9NHCO-R^{10}-CONHR^9 \quad (3)$$

$$R^9CONH-R^{10}-N(R^{11})_2 \quad (4)$$

In Formulae (1), (2), (3) and (4), each of $R^9$ and $R^{11}$ independently represents an alkyl group having from 1 to 30 carbon atoms or an alkenyl group having from 2 to 30 carbon atoms, and $R^{10}$ represents an alkylene group having from 1 to 10 carbon atoms. $R^9$ and $R^{11}$ may be the same or different from each other. Two of $R^{11}$ may be the same or different from each other.

Examples of an organic filler include particles of acrylic resin, cellulosic resin, polystyrene resin and the like.

Examples of an inorganic filler include particles of silicon dioxide, aluminum hydroxide, aluminum nitride, silicon nitride, aluminum oxide, zirconium oxide, silicon carbide and the like. Also, an inorganic filler may be glass particles.

The average volume particle diameter of an organic filler or an inorganic filler is preferably from 0.01 μm to 50 μm. The average volume particle diameter refers to a particle diameter (D50%) that is a diameter at which an integrated value on volume basis in a particle size distribution is 50%. The average volume particle diameter is measured with a laser diffraction scattering particle size distribution measuring apparatus (for example, Beckman Coulter, Inc., LS 13 320). The more detailed method of measuring a particle diameter is as follows. For the measurement, from 0.01 g to 0.10 g of a filler is dispersed in 125 ml of a solvent (terpineol). The refractive index of the solvent is set to 1.48, and the refractive index of the filler is set to a value corresponding to the value of the material used (for example, 1.57 for aluminum hydroxide particles). From a particle size distribution measured under the above-described conditions, a particle diameter (D50%) at which an integrated value on volume basis is 50% is calculated.

Examples of the other metal alkoxide compounds include titanium alkoxide, zirconium alkoxide and silicon alkoxide.

(High-Boiling Point Material)

The composition for forming a passivation film may use a high-boiling point material, in combination with or in place of a resin. A high-boiling point material is preferably a material that readily evaporates upon heating and does not require a defatting treatment. In particular, a high-boiling point material is preferably a high-boiling point material having a viscosity that is high enough to maintain a printed shape after printing or application. Examples of a material that satisfies the conditions include isobornyl cyclohexanol.

Isobornyl cyclohexanol is commercially available as TERUSOLVE MTPH (trade name, Nippon Terpene Chemicals, Inc.) Isobornyl cyclohexanol has a high boiling point from 308° C. to 318° C., and can be removed from a composition layer only by allowing to evaporate by heating, without performing defatting treatment by thermal treatment (sintering) like a resin. Therefore, it is possible to remove a major part of isobornyl cyclohexanol and a solvent that is optionally included in a composition layer during a drying process that is performed after application of the composition onto a semiconductor substrate.

When the composition for forming a passivation layer includes other high-boiling point materials, the content of the other high-boiling point materials is preferably from 3% by mass to 95% by mass, more preferably from 5% by mass to 90% by mass, particularly preferably from 7% by mass to 80% by mass, in the total mass of the composition for forming a passivation layer.

The composition for forming a passivation layer may include an oxide of at least one selected from the group consisting of Nb, Ta, V, Y and Hf (hereinafter, referred to as a "specific oxide"). Because a specific oxide is an oxide produced by performing thermal treatment (sintering) of a Formula (I) compound, a passivation layer formed from a composition for forming a passivation layer that includes a specific oxide is expected to exert an excellent passivation effect.

The composition for forming a passivation layer may further include aluminum oxide ($Al_2O_3$). Aluminum oxide is an oxide produced by performing thermal treatment (sintering) of a compound represented by Formula (II). Accordingly, a composition for forming a passivation layer that includes a Formula (I) compound and aluminum oxide is expected to exert an excellent passivation effect.

The viscosity of the composition for forming a passivation layer is not particularly limited, and can be appropriately selected depending on the application method onto a semiconductor substrate, and the like. For example, the viscosity of the composition for forming a passivation layer can be from 0.01 Pa·s to 10,000 Pa·s. From the viewpoint of pattern formability, the viscosity of the composition for forming a passivation layer is preferably from 0.1 Pa·s to 1,000 Pa·s. The viscosity is measured at 25° C. at a shear rate of 1.0 $s^{-1}$, with a rotational shear viscometer.

The shear viscosity of the composition for forming a passivation layer is not particularly limited, and the composition for forming a passivation layer preferably has a thixotropic property. In particular, from the viewpoint of pattern formability, a thixotropic ratio ($\eta_1/\eta_2$), which is obtained by dividing shear viscosity $\eta_1$ at a shear rate of 1.0 $s^{-1}$ by shear viscosity $\eta_2$ at a shear rate of 10 $s^{-1}$, is preferably from 1.05 to 100, more preferably from 1.1 to 50. The shear viscosity is measured at a temperature of 25° C. with a rotational shear viscometer equipped with a cone plate (diameter: 50 mm, cone angle: 1°).

On the other hand, when the composition for forming a passivation layer includes a high-boiling point material instead of a resin, a thixotropic ratio ($\eta_1/\eta_3$), which is calculated by dividing a shear viscosity $\eta_1$ at a shear rate of 1.0 $s^{-1}$ by shear viscosity $\eta_3$ at a shear rate of 1,000 $s^{-1}$, is preferably from 1.05 to 100, more preferably from 1.1 to 50, from the viewpoint of pattern formability.

The method of producing the composition for forming a passivation layer is not particularly limited. For example, the composition can be produced by mixing a specific compound represented by Formula (I), a compound represented by Formula (II), a liquid medium, a resin and the like, according to a conventional method.

Identification of the component in the composition for forming a passivation layer and determination of the content of the component can be performed by thermal analysis such as differential thermal-thermogravimetric simultaneous measurement (TG/DTA), spectral analysis such as nuclear magnetic resonance (NMR), infrared spectroscopy (IR), chromatography analysis such as high-speed liquid chromatography (HPLC), gel permeation chromatography (GPC) or the like.

<Semiconductor Substrate Having Passivation Layer>

A semiconductor substrate having a passivation layer according to the invention includes a semiconductor substrate and a passivation layer that is a thermally-treated (sintered) product of the composition for forming a passivation layer and is provided on an entire or partial surface of the semiconductor substrate. By having a passivation layer that is a thermally-treated (sintered) product of the composition for forming a passivation layer, the semiconductor substrate having a passivation layer exhibits an excellent passivation effect.

The semiconductor substrate is not particularly limited, and appropriately selected from those conventionally used depending on the purpose. Examples of the semiconductor substrate include a substrate of silicon, germanium or the like to which a p-type impurity or an n-type impurity is doped (diffused). Among them, a silicon substrate is preferred. The semiconductor substrate may be either a p-type semiconductor substrate or an n-type semiconductor substrate. In particular, from the viewpoint of a passivation effect, a semiconductor substrate having a p-type layer at a side at which a passivation layer is formed is preferred. The p-type layer on a semiconductor substrate may be a p-type layer derived from a p-type semiconductor substrate, or a p-type layer that is formed on an n-type semiconductor substrate or a p-type semiconductor substrate as a p-type diffusion layer or a $p^+$-type diffusion layer.

The thickness of the semiconductor substrate is not particularly limited, and appropriately selected depending on the purpose. For example, the thickness of the semiconductor substrate may be from 50 μm to 1,000 μm, preferably from 75 μm to 750 μm.

The thickness of the passivation layer formed on a semiconductor substrate is not particularly limited, and appropriately selected depending on the purpose. For example, the thickness of the passivation layer is preferably from 5 nm to 50 μm, more preferably from 10 nm to 30 μm, further preferably from 15 nm to 20 μm. The thickness of the passivation layer can be measured with an interference-type film thickness meter or the like.

The semiconductor substrate having a passivation layer can be applied to a photovoltaic cell element, a light-emitting diode element, or the like. For example, a photovoltaic cell element in which the semiconductor substrate having a passivation layer is used exhibits an excellent conversion efficiency.

<Method of Producing Semiconductor Substrate Having Passivation Layer>

The method of producing a semiconductor substrate having a passivation layer according to the invention includes: a process of applying the composition for forming a passivation layer on an entire or partial surface of a semiconductor substrate to form a composition layer; and a process of forming a passivation layer by subjecting the composition layer to a thermal treatment (sintering). The method may include other processes, if necessary.

By using the composition for forming a passivation layer, a passivation layer having an excellent passivation effect can be formed by a simple method.

The method of producing a semiconductor substrate having a passivation layer preferably further includes a process of applying an aqueous alkaline solution onto the semiconductor substrate before a process of forming a composition layer. In other words, a surface of a semiconductor substrate is preferably washed with an alkaline aqueous solution before the application of a composition for forming a passivation layer on a semiconductor substrate. Washing with an aqueous alkaline solution can remove organic substances, particles or the like that exist on a surface of a semiconductor substrate, thereby further enhancing the passivation effect. An example of the method of washing with an aqueous alkaline solution is RCA washing that is commonly known in the art. For example, a semiconductor substrate is immersed in a mixture of ammonium water and hydrogen peroxide water, treated at a temperature of from 60° C. to 80° C. to remove organic substances and particles, and washed. The washing time is preferably from 10 seconds to 10 minutes, more preferably from 30 seconds to 5 minutes.

The method of applying a composition for forming a passivation layer on a semiconductor substrate to form a composition layer is not particularly limited. For example, a method of applying a composition for forming a passivation layer on a semiconductor substrate by a known application method may be employed. Examples of the method include immersion, screen printing, ink jetting, dispensing, spin coating, brushing, spraying, doctor blading and roll coating. Among them, screen printing and ink jetting are preferred from the viewpoint of pattern formability and productivity.

The amount of the composition for forming a passivation layer to be applied may be appropriately selected depending on the purpose. For example, it is appropriately adjusted so that the passivation layer to be formed has a desired thickness.

The composition layer formed with a composition for forming a passivation layer is subjected to thermal treatment (sintering) to form a thermally-treated product layer (sintered product layer) derived from the composition layer, thereby forming a passivation layer on a semiconductor substrate.

The conditions for the thermal treatment (sintering) of the composition layer are not particularly limited, so long as a compound represented by Formula (I) included in a composition layer and a compound represented by Formula (II) that are optionally included are converted to a metal oxide or a complex oxide as a thermally-treated (sintered) product. In order to effectively impart a fixed charge to a passivation layer and to provide a more excellent passivation effect, the thermal treatment (sintering) is preferably performed at a temperature of from 300° C. to 900° C., more preferably from 450° C. to 800° C. The temperature for the thermal treatment (sintering) mentioned herein refers to the highest temperature in the furnace used for the thermal treatment (sintering). The time for the thermal treatment (sintering) may be appropriately selected depending on the temperature for the thermal treatment (sintering). For example, the time may be from 0.1 hours to 10 hours, preferably from 0.2 hours to 5 hours. The time for the thermal treatment (sintering) mentioned herein refers to a retention time at the highest temperature.

The thermal treatment (sintering) may be performed with a diffusion furnace (for example, ACCURON CQ-1200, Hitachi Kokusai Electric Inc. and 206A-M100, Koyo Thermo Systems Co., Ltd.) The atmosphere in which the thermal treatment (sintering) is performed is not particularly limited, and the thermal treatment may be performed in an air atmosphere.

The thickness of a passivation layer that is produced by a method of producing a semiconductor substrate having a passivation layer is not particularly limited, and appropriately selected depending on the purpose. For example, an average thickness of a passivation layer is preferably from 5 nm to 50 μm, preferably from 10 nm to 30 μm, further preferably from 15 nm to 20 μm.

The average thickness of the formed passivation layer is determined by measuring a thickness at three points with an interference type film thickness meter (e.g., Filmetrics Corporation, F20 FILM THICKNESS MEASUREMENT SYSTEM) by a routine method, and calculating an arithmetic average of the measured values.

The method of producing a semiconductor substrate having a passivation layer may further include a process of performing drying treatment of a composition layer formed from the composition for forming a passivation layer, between the process of applying a composition for forming a passivation layer onto a semiconductor substrate and the process of forming a passivation layer by performing thermal treatment (sintering). By including a process of performing drying treatment of the composition layer, a passivation layer having a more uniform thickness can be formed.

The process of performing drying treatment of a composition layer is not particularly limited, so long as at least a part of a liquid medium that may be included in the composition for forming a passivation layer can be removed. The drying treatment is, for example, a thermal treatment performed at a temperature of from 30° C. to 250° C. for one minute to 60 minutes, preferably a thermal treatment performed at a temperature of from 40° C. to 220° C. for 3 minutes to 40 minutes. The drying treatment may be performed at an ambient pressure or under reduced pressure.

When the composition for forming a passivation layer includes a resin, the method of producing a semiconductor substrate having a passivation layer may include a process of defatting a composition layer formed from the composition for forming a passivation layer between the process of applying a composition for forming a passivation layer and the process of forming a passivation layer by performing thermal treatment (sintering). By performing defatting of the composition layer, a passivation layer having a more uniform passivation effect can be formed.

The process of performing defatting of a composition layer is not particularly limited, so long as at least a part of a resin that may be optionally included in the composition for forming a passivation layer can be removed. The defatting process can be, for example, a thermal treatment performed at a temperature of from 250° C. to 450° C. for 10 minutes to 120 minutes, preferably a thermal treatment performed at a temperature of from 300° C. to 400° C. for 3 minutes to 60 minutes. The defatting process is preferably performed in the presence of oxygen, more preferably in an air atmosphere.

<Photovoltaic Cell Element>

The photovoltaic cell element of the invention includes a semiconductor substrate having a pn junction of a p-type layer and an n-type layer, a passivation layer that is a thermally-treated (sintered) product of the composition for forming a passivation layer and is provided on an entire or partial surface of the semiconductor substrate, and an electrode provided on at least one of the p-type layer and the n-type layer of the semiconductor substrate. The photovoltaic cell element may further include other constituents, if necessary.

By having a passivation layer formed from the composition for forming a passivation layer of the invention, the photovoltaic cell element exhibits an excellent conversion efficiency.

The semiconductor substrate to which the composition for forming a passivation layer is to be applied is not particularly limited, and appropriately selected from those conventionally employed depending on the purpose. As a semiconductor substrate, a substrate as described above as the semiconductor substrate having a passivation layer may be used, and the same applies to the preferably utilized ones. A surface on which a passivation layer is to be provided may be any of a back surface, a light receiving surface or a side surface of a photovoltaic cell element.

The thickness of a passivation layer formed on a semiconductor substrate is not particularly limited, and appropriately selected depending on the purpose. For example, an average thickness of a passivation layer is preferably from 5 nm to 50 μm, more preferably from 10 nm to 30 μm, still more preferably from 15 nm to 20 μm.

The shape and the size of the photovoltaic cell element may not be limited. For example, the photovoltaic cell element preferably has a rough square shape of from 125 mm to 156 mm for each side.

<Method of Producing Photovoltaic Cell Element>

The method of producing a photovoltaic cell element according to the invention includes a process of forming a composition layer by applying the composition for forming a passivation layer on an entire or partial surface of a semiconductor substrate having a pn junction of a p-type layer and an n-type layer; a process of forming a passivation layer by performing thermal treatment (sintering) of the composition layer; and a process of forming an electrode on at least one of the p-type layer and the n-type layer. The method of producing a photovoltaic cell element may further include other processes, if necessary.

By using the composition for forming a passivation layer of the invention, a photovoltaic cell element that exhibits an excellent conversion efficiency can be produced by a simple method.

As a method of forming an electrode on at least one of a p-type layer and an n-type layer of a semiconductor substrate, a conventionally used method may be employed. For example, an electrode can be formed by applying a paste for forming an electrode such as a silver paste, an aluminum paste or the like onto a desired region of a semiconductor substrate, and subjecting the same to thermal treatment (sintering), if necessary.

The surface of a semiconductor substrate on which a passivation layer is to be provided may be either a p-type layer or an n-type layer. In particular, a p-type layer is preferred from the viewpoint of conversion efficiency.

Details and preferred embodiments of the method of forming a passivation layer with the composition for forming a passivation layer are similar to those as described above in connection with the method of producing a semiconductor substrate having a passivation layer.

The thickness of a passivation layer to be formed on a semiconductor substrate is not particularly limited, and appropriately selected depending on the purpose. For example, an average thickness of a passivation layer is preferably from 5 nm to 50 μm, more preferably from 10 nm to 30 μm, further preferably from 15 nm to 20 μm.

In the following, embodiments of the invention will be illustrated with reference to the drawings.

FIG. 1 is a process chart that schematically shows, as a cross sectional view, an example of the method of producing a photovoltaic cell element having a passivation layer according to the present embodiment. However, this process chart does not limit the invention in any way.

In FIG. 1 (1), p-type semiconductor substrate 1 is washed with an alkaline aqueous solution to remove organic substances, particles or the like on a surface of p-type semiconductor substrate 1. By performing washing, a passivation effect is further improved. As a method of washing with an alkaline aqueous solution, a well-known RCA washing may be used.

Subsequently, as shown in FIG. 1 (2), a surface of p-type semiconductor substrate 1 is subjected to alkaline etching or the like, and a concave-convex surface (also referred to as texture) is formed. By forming a texture, reflection of sunlight at a light receiving surface can be suppressed. For alkaline etching, an etching solution containing NaOH and IPA (isopropyl alcohol) can be used.

Subsequently, as shown in FIG. 1 (3), phosphorus or the like is thermally diffused at a surface of p-type semiconductor substrate 1, and $n^+$-type diffusion layer 2 having a depth of submicron order is formed and a pn junction is formed at an interface with a p-type bulk portion.

Examples of the method for diffusing phosphorus include, for example, a method including performing treatment in a mixed gas atmosphere including phosphorus oxychloride (POCl$_3$), nitrogen and oxygen at a temperature of from 800° C. to 1000° C. for several ten minutes. Since phosphorus is diffused utilizing a mixed gas, $n^+$-type diffusion layer 2 is formed at a back surface and a side surface (not shown), in addition to the light receiving surface (front surface), as shown in FIG. 1 (3). Further, PSG (silicate glass) layer 3 is formed on $n^+$-type diffusion layer 2. Accordingly, side-etching is performed to remove PSG layer 3 and $n^+$-type diffusion layer 2 formed at the side surface.

Subsequently, as shown in FIG. 1 (4), PSG layer 3 formed at the light receiving surface and the back surface is removed with an etching solution such as hydrofluoric acid. Further, etching treatment is separately conducted to remove $n^+$-type diffusion layer 2 formed at the back surface, as shown in FIG. 1 (5).

Then, as shown in FIG. 1 (6), anti-reflection film 4, such as silicon nitride, having a thickness of approximately 90 nm is formed on $n^+$-type diffusion layer 2 at the light receiving surface by PECVD (plasma enhanced chemical vapor deposition) method or the like.

Then, as shown in FIG. 1 (7), the composition for forming a passivation layer of the invention is applied by screen printing or the like onto a part of the back surface. Then, after drying, thermal treatment (sintering) is performed at a temperature of from 300° C. to 900° C. to form passivation layer 5.

Figure 5:
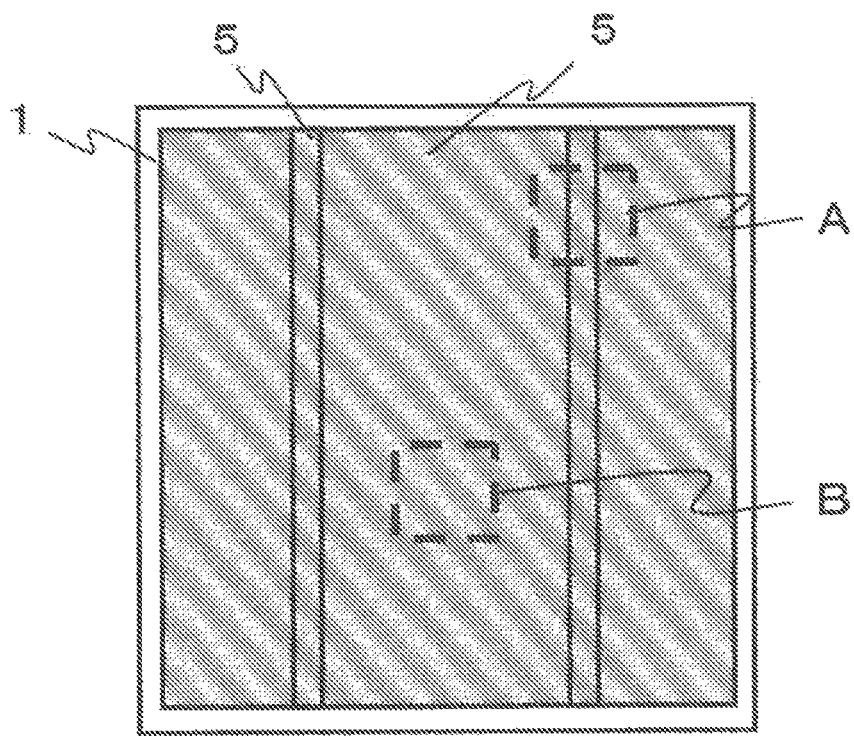
FIG. 5 is a cross sectional view that schematically shows an example of a pattern formed at a back surface of a passivation layer.
Figure 7:
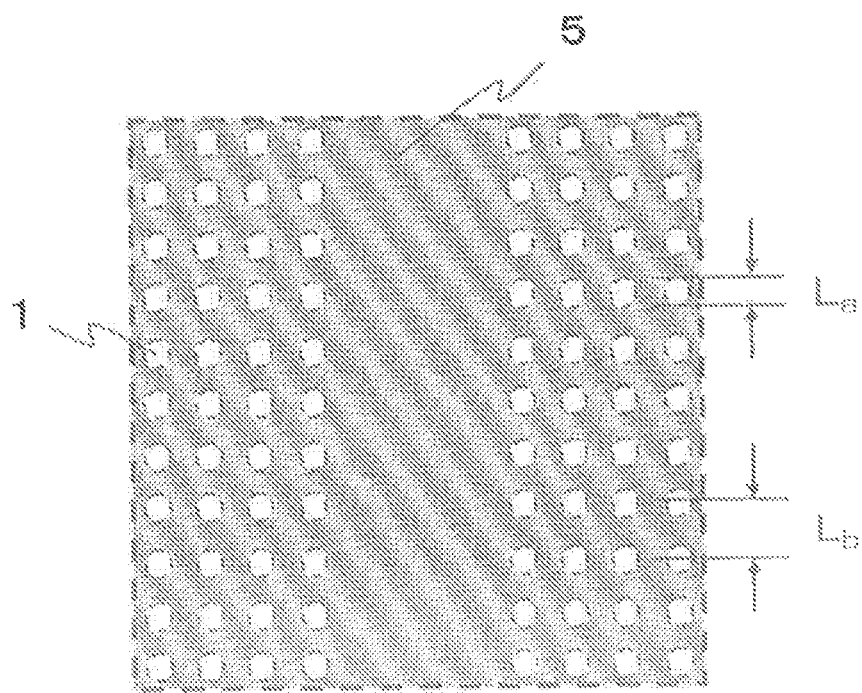
FIG. 7 is a schematic plan view of enlarged part A in FIG. 5.
Figure 8:
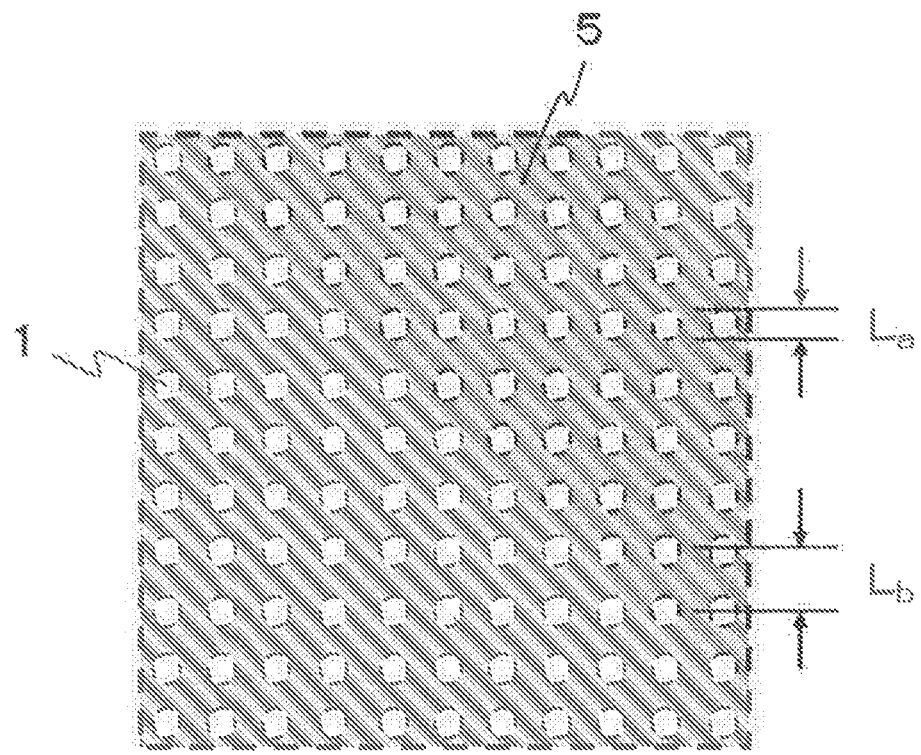
FIG. 8 is a schematic plan view of enlarged part B in FIG. 5.

An example of a pattern of passivation layer 5 at the back surface is shown as a schematic plan view in FIG. 5. FIG. 7 is an enlarged schematic plan view of part A in FIG. 5. FIG. 8 is an enlarged schematic plan view of the part B in FIG. 5. In the case of a pattern of passivation layer 5 shown in FIG. 5, as is seen from FIGS. 7 and 8, passivation layer 5 at the back surface is formed in a pattern in which p-type semiconductor substrate 1 is exposed in the form of dots, excluding the area at which back surface power extraction electrode 7 is to be formed in the subsequent process. The openings in the form of dots are preferably regularly positioned with a dot diameter ($L_a$) and an interval ($L_b$). The dot diameter ($L_a$) and the interval ($L_b$) may be arbitrarily set, but from the viewpoint of a passivation effect and suppressing recombination of minority carriers, $L_a$ is preferably from 5 µm to 2 mm and $L_b$ is preferably from 10 µm to 3 mm, and it is more preferable that $L_a$ is from 10 µm to 1.5 mm and $L_b$ is from 20 µm to 2.5 mm, and it is further preferable that $L_a$ is from 20 µm to 1.3 mm and $L_b$ is from 30 µm to 2 mm.

In the above description, a passivation layer having a desired shape is formed by applying the composition for forming a passivation layer at a portion at which a passivation layer is to be formed (a portion other than the dotted openings), and by performing thermal treatment (sintering). Alternatively, a passivation layer may be formed by applying the composition for forming a passivation layer on an entire surface including dotted openings, and after performing thermal treatment (sintering), selectively removing a passivation layer formed at the dotted openings by laser irradiation, photolithography or the like. It is also possible to selectively apply the composition for forming a passivation layer by providing a mask with a masking material to a portion to which the composition for forming a passivation layer is not to be applied, such as dotted openings.

Figure 4:
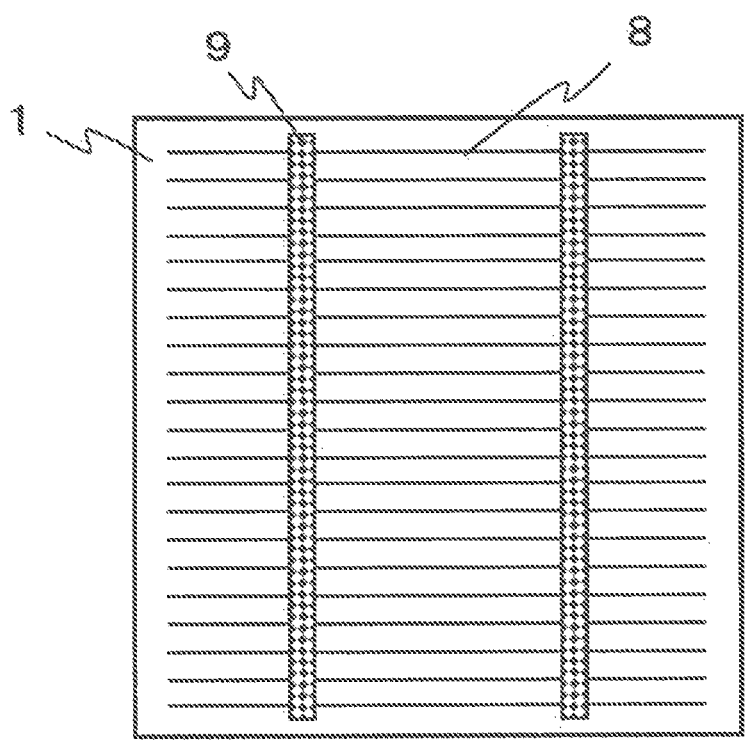
FIG. 4 is a cross sectional view that schematically shows an example of a light receiving surface of a photovoltaic cell element.

Subsequently, as shown in FIG. 1 (8), a silver electrode paste that includes glass particles is applied onto a light receiving surface by screen printing or the like. FIG. 4 is a schematic plan view showing an example of a light receiving surface of a photovoltaic cell element. As shown in FIG. 4, a light receiving surface electrode is formed of light receiving surface current collector electrode 8 and light receiving surface power extraction electrode 9. In order to secure a light receiving area, the area for forming these light receiving surface electrodes needs to be small. Moreover, from the viewpoint of resistivity of a light receiving surface electrode and productivity, light receiving surface current collector electrode 8 preferably has a width of from 10 µm to 250 µm, and light receiving surface power extraction electrode 9 preferably has a width of from 100 µm to 2 mm. Although two light receiving surface power extraction electrodes 9 are provided in FIG. 4, from the viewpoint of power extraction efficiency (power generation efficiency) of minority carriers, the number of light receiving surface power extraction electrode 9 may be three or four.

Figure 9:
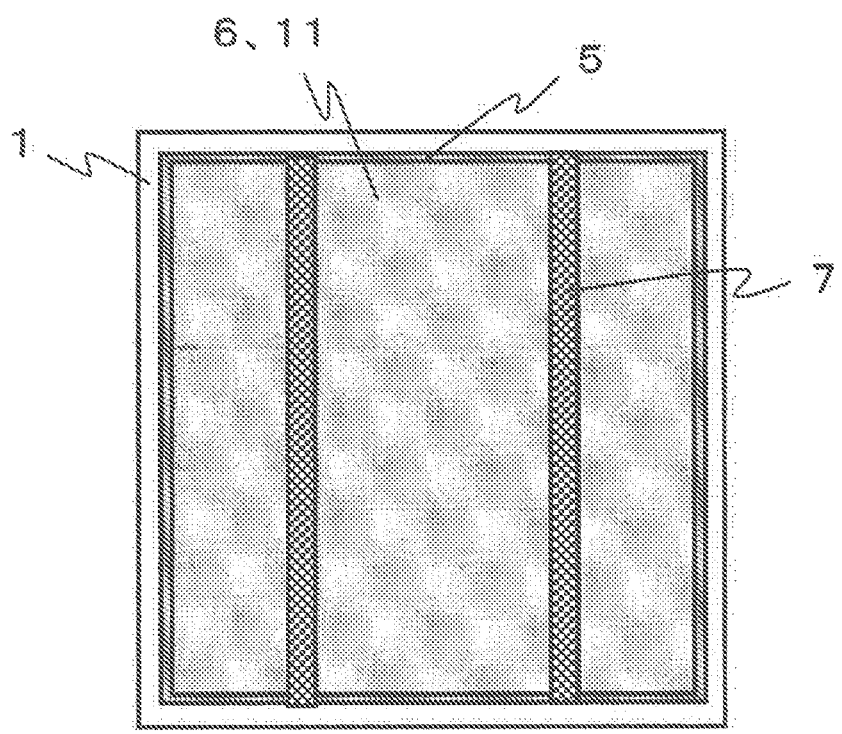
FIG. 9 is a schematic plan view showing an example of a back surface of a photovoltaic cell element.

On the other hand, as shown in FIG. 1 (8), an aluminum electrode paste including a glass powder and a silver electrode paste including glass particles are applied onto a back surface by screen printing, or the like. FIG. 9 is a schematic plan view showing an example of a back surface of a photovoltaic cell element. The width of back surface power extraction electrode 7 is not particularly limited, and from the viewpoint of connectivity or the like of a wiring material during a subsequent process of producing a photovoltaic cell, the width of back surface power extraction electrode 7 is preferably from 100 µm to 10 mm.

Light receiving surface current collector electrode 8 and light receiving surface power extraction electrode 9 are formed on the light receiving surface, and back surface current collector electrode 6 and back surface power extraction electrode 7 are formed on the back surface, by applying an electrode paste on the light receiving surface and the back surface, respectively, and after drying, performing thermal treatment (sintering) both on the light receiving surface and the back surface in an air atmosphere at a temperature of from approximately 450° C. to 900° C.

After the thermal treatment (sintering), as shown in FIG. 1 (9), at the light receiving surface, glass particles in the silver electrode paste for forming a light receiving electrode react with anti-reflection film 4 (fire-through), thereby achieving electrical connection (ohmic contact) between the light receiving surface electrodes (light receiving surface current collector electrode 8 and light receiving surface power extraction electrode 9) and $n^+$-type diffusion layer 2. At the back surface, aluminum in an aluminum electrode paste diffuses into semiconductor substrate 1 at a region at which semiconductor substrate 1 is exposed in a dotted pattern (the area at which passivation layer 5 is not formed) upon thermal treatment (sintering), thereby forming $p^+$-type diffusion layer 10. In the invention, by using the composition for forming a passivation layer that exhibits an excellent storage stability, a passivation layer that exhibits an excellent passivation effect can be formed by a simple method, and a photovoltaic cell element that exhibits an excellent power generation performance can be produced.

Figure 2:
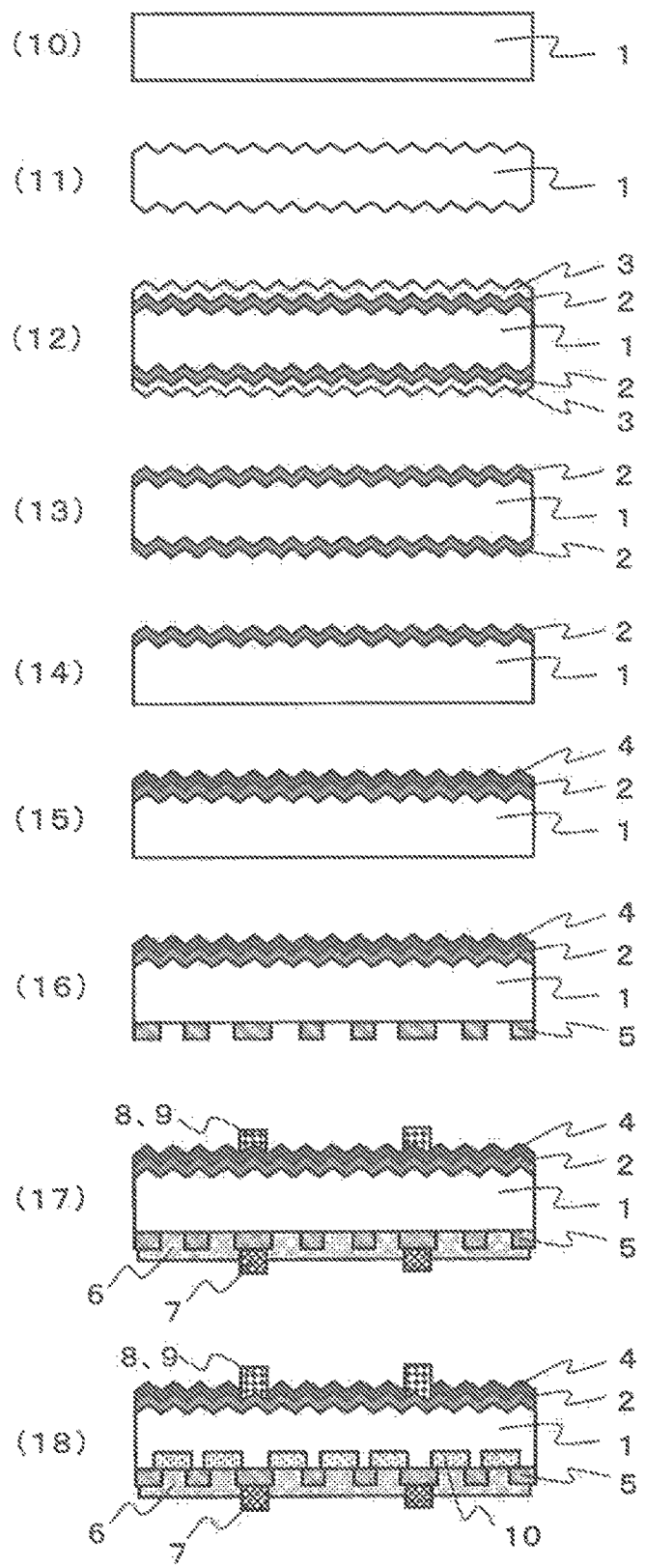
FIG. 2 is a cross sectional view that schematically shows an example of a method of producing a photovoltaic cell element having a passivation layer.

FIG. 2 is a process chart expressed as a cross sectional view, which shows another example of a method of producing a photovoltaic cell element having a passivation layer according to the embodiment, wherein a photovoltaic cell element can be manufactured in the same manner as in FIG. 1, except that $n^+$-type diffusion layer 2 of the back surface is removed by etching treatment, and the back surface is planarized. During the planarization, a method that includes immersing a back surface of a semiconductor substrate in a mixed solution of nitric acid, hydrofluoric acid and acetic acid, or a potassium hydroxide solution may be utilized.

Figure 3:
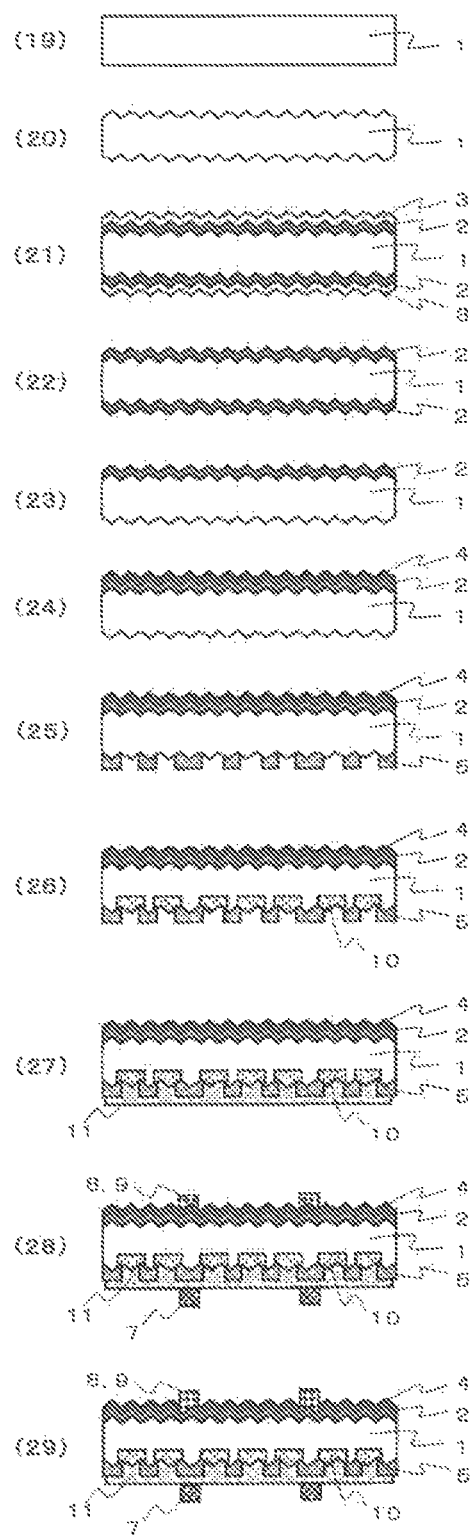
FIG. 3 is a cross sectional view that schematically shows an example of a method of producing a photovoltaic cell element having a passivation layer.

FIG. 3 is a process chart expressed as a cross sectional view that shows another example of the method of producing a photovoltaic cell element having a passivation layer according to the invention. In this method, processes for forming a textured structure, $n^+$-type diffusion layer 2 and anti-reflection film 4 on semiconductor substrate 1 (processes shown from FIG. 3 (19) to (24)) are similar to the processes of the method shown in FIG. 1.

Figure 6:
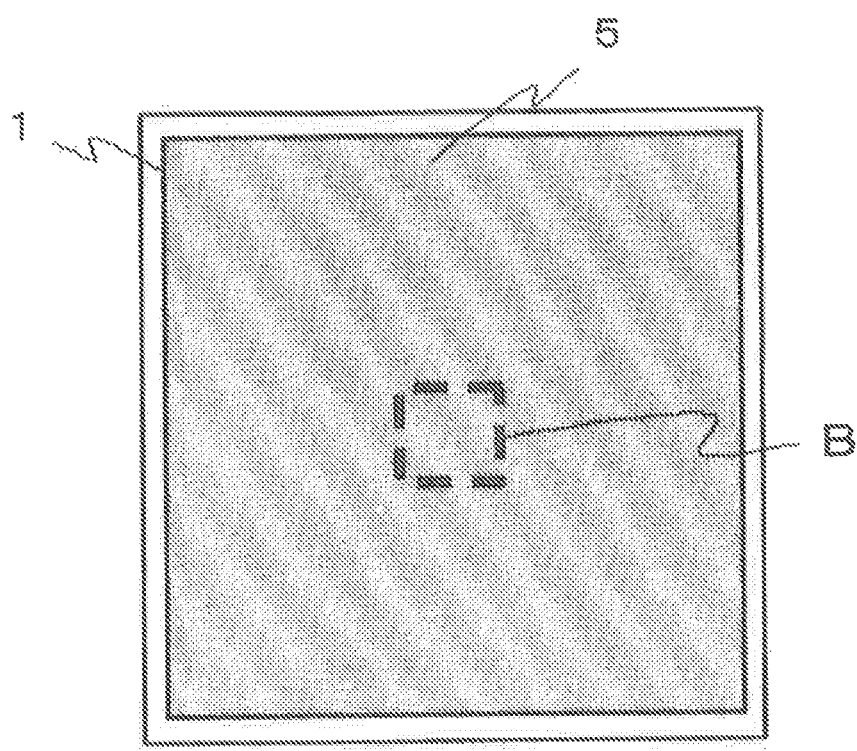
FIG. 6 is a cross sectional view that schematically shows an example of a pattern formed at a back surface of a passivation layer.

After the formation of anti-reflection film 4, the composition for forming a passivation layer is applied, as shown in FIG. 3 (25). In FIG. 6, an example of a pattern of a passivation layer at the back surface, as is shown in a schematic plan view. In the pattern of a passivation layer shown in FIG. 6, dotted openings are arranged on the entire back surface, and dotted openings are arranged also at a portion at which a back surface power extraction electrode is to be formed in the subsequent process.

Subsequently, boron or aluminum is allowed to diffuse at a portion of the back surface of semiconductor substrate 1 at which semiconductor substrate 1 is exposed in a dotted pattern (a portion at which passivation layer 5 is not formed), as shown in FIG. 3 (26), and $p^+$-type diffusion layer 10 is formed. When boron is allowed to diffuse during formation of a $p^+$-type diffusion layer, the diffusion can be performed by a method of performing treatment in a gas containing boron trichloride ($BCl_3$) at a temperature of approximately 1,000° C. However, since diffusion is performed with a gas, as with the case of using phosphorus oxychloride, $p^+$-type diffusion layer 10 may be formed on a light receiving surface, a back surface and a side surface of semiconductor substrate 1. Therefore, it is necessary to suppress unnecessary diffusion of boron in p-type semiconductor substrate 1, by forming a mask at a portion other than the dotted openings or the like.

When aluminum is allowed to diffuse during the formation of $p^+$-type diffusion layer 10, the diffusion can be performed by applying an aluminum paste to the dotted openings, performing thermal treatment (sintering) at a temperature of from 450° C. to 900° C., allowing aluminum to diffuse through the dotted openings to form $p^+$-type diffusion layer 10, and then performing etching with hydrochloric acid or the like to remove a thermally-treated product layer (sintered product layer) derived from the aluminum paste formed on $p^+$-type diffusion layer 10.

Subsequently, aluminum is physically vapor-deposited on the entire back surface to form aluminum electrode 11, as shown in FIG. 3 (27).

Thereafter, as shown in FIG. 3 (28), a silver electrode paste including glass particles is applied onto the light receiving surface by screen printing or the like, and a silver electrode paste including glass particles is applied onto the back surface by screen printing or the like. The silver electrode paste is applied onto the light receiving surface in the shape of a pattern of the light receiving surface electrode as shown in FIG. 4, and the silver electrode paste is applied on the back surface in the form of a pattern of the back surface electrode as shown in FIG. 9.

After applying the electrode paste to the light receiving surface and the back surface, respectively, both of the light receiving surface and the back surface are subjected to thermal treatment (sintering) in an air atmosphere at a temperature of from approximately 450° C. to 900° C., thereby forming light receiving surface current collector electrode 8 and light receiving surface power extraction electrode 9 on the light receiving surface, and forming aluminum electrode 11 and back surface power extraction electrode 7 on the back surface, respectively, as shown in FIG. 3 (29). At the light receiving surface, a light receiving surface electrode and $n^+$-type diffusion layer 2 are electrically connected to each other, and at the back surface, aluminum electrode 11 formed by vapor deposition and back surface power extraction electrode 7 are electrically connected to each other.

<Photovoltaic Cell>

The photovoltaic cell includes the photovoltaic cell element as described above and a wiring material provided on an electrode of the photovoltaic cell element. In a preferred embodiment, the photovoltaic cell includes at least one photovoltaic cell element, and a wiring material is provided on a power extraction electrode of the photovoltaic cell element. As necessary, the photovoltaic cell includes plural photovoltaic cell elements that are connected via wiring material 13, and is sealed with a sealing material. The wiring material and the sealing material are not particularly limited, and may be appropriately selected from those conventionally used in the art.

EXAMPLES

The invention is hereinafter specifically explained with reference to the examples, but the invention is not limited thereto.

Example 1

(Preparation of Composition for Forming Passivation Layer 1)

Niobium pentaethoxide (1.2 g; Hokko Chemical Industry Co., Ltd., structural formula: $Nb(OC_2H_5)_5$, molecular weight: 318.2) and terpineol (18.8 g; Nippon Terpene Chemicals, Inc., also referred to as TPO) were mixed to prepare composition for forming a passivation layer 1.

(Evaluation of Thixotropy)

Immediately after the preparation (within 12 hours) of composition for forming a passivation layer 1, the shear viscosity of the composition was measured at a temperature of 25° C. at a shear rate of 1.0 $s^{-1}$ and 10 $s^{-1}$, respectively, with a rotational viscometer (Anton Paar GmbH, MCR301) with a cone plate (diameter: 50 mm, cone angle: 1°).

The shear viscosity ($\eta_1$) at a shear rate of 1.0 $s^{-1}$ was 22.3 Pa·s, and the shear viscosity ($\eta_2$) at a shear rate of 10 $s^{-1}$ was 18.9 Pa·s. The thixotropic ratio ($\eta_1/\eta_2$) at a shear rate of 1.0 $s^{-1}$ and at a shear rate of 10 $s^{-1}$ was 1.18.

(Evaluation of Storage Stability)

The shear viscosity of composition for forming a passivation layer 1 as prepared above was measured immediately after the preparation (within 12 hours) and after being stored at 25° C. for 30 days, respectively. The shear viscosity was measured with a rotational viscometer (Anton Paar GmbH, MCR301) equipped with a cone plate (diameter: 50 mm, cone angle: 1°) at a temperature of 25° C. at a shear rate of 1.0 $s^{-1}$. The shear viscosity immediately after the preparation at 25° C. was 22.3 Pa·s, and the shear viscosity after being stored at 25° C. for 30 days was 23.9 Pa·s.

In the evaluation of storage stability, the result in which a change in shear viscosity after storage for 30 days is less than 10% is scored as A, the result in which a change in shear viscosity is 10% or more and less than 30% is scored as B, and the result in which a change in shear viscosity is 30% or more is scored as C. When the result is A or B, the storage stability of the composition for forming a passivation layer is considered to be favorable. The value of the shear viscosity measured immediately after the preparation and the evaluation results of the storage stability are shown in Table 2.

(Evaluation of Printability)

In order to evaluate the printability of the composition for forming a passivation layer, two types of semiconductor substrates were used. Specifically, a monocrystalline p-type silicon substrate having a mirror-shaped surface (50 mm square, thickness: 625 µm or less, hereinafter referred to as Substrate A) and a monocrystalline p-type silicon substrate having a textured structure on its surface (50 mm square, thickness: 180 µm or less, hereinafter referred to as Substrate B) were used.

In order to evaluate the unevenness in printing, composition for forming a passivation layer 1 was applied by screen printing 10 times in succession onto Substrates A and B, respectively. As a result of visual observation, it was confirmed that nine of Substrate A and eight of Substrate B did not have unevenness in printing.

The result in which nine or more of the ten substrates did not have unevenness in printing is scored as A, the result in which six to eight of the ten substrates did not have unevenness in printing is scored as B, and the result in which five or less of the ten substrates did not have unevenness in printing is scored as C. When the result is A or B, the printability of the composition for forming a passivation layer is considered to be favorable.

In the present specification, unevenness in printing refers to a phenomenon in which variation in the thickness of the composition layer occurs as a result of partially failing to readily separating a screen from the silicon substrate.

In order to evaluate print blur, composition for forming a passivation layer 1 was applied by screen printing onto the entire surface of Substrates A and B, respectively, excluding the dotted openings formed in a pattern shown in FIG. 8. The dotted opening pattern used in the evaluation has a dot diameter ($L_a$) of 368 µm and an interval ($L_b$) of 0.5 mm.

Subsequently, Substrates A and B applied with the composition for forming a passivation layer 1 was subjected to drying treatment by heating at 150° C. for three minutes to evaporate a liquid medium. Then, Substrates A and B were subjected to thermal treatment (sintering) at a temperature of 700° C. for 10 minutes, and allowed to cool at room temperature (25° C.).

For the evaluation of print blur, a dot diameter ($L_a$) of dotted openings in a passivation layer formed on a substrate after the thermal treatment (sintering) was measured. The dot diameter ($L_a$) was measured at ten points, and an average thereof was calculated. The dot diameter ($L_a$) was 332 µm for Substrate A, and 270 µm for Substrate B. When the result is A or B, evaluation for the print blur of the composition for forming a passivation layer is considered to be favorable.

The result in which a decrease ratio of the dot diameter ($L_a$) after the thermal treatment (sintering) with respect to a dot diameter ($L_a$) immediately after printing (368 µm) is less than 10% is scored as A, the result in which the decrease ratio is from 10% to less than 30% is scored as B, and the result in which the decrease ratio is 30% or more is scored as C.

In the present specification, print blur refers to a phenomenon in which the composition for forming a passivation layer spreads on the semiconductor substrate on which the passivation layer is formed.

(Measurement of Effective Lifetime)

One of the ten Substrates A onto which composition for forming a passivation layer 1 was entirely applied, which were prepared for the evaluation of unevenness in printing as described above, was subjected to drying treatment by heating at 150° C. for 3 minutes to evaporate a liquid medium. Subsequently, a semiconductor substrate was subjected to thermal treatment (sintering) at a temperature of 700° C. for 10 minutes, and allowed to cool to room temperature (25° C.), thereby preparing a substrate for evaluation. The thermal treatment (sintering) was performed using a diffusion furnace (ACCURON CQ-1200, Hitachi Kokusai Electric Inc.) in an air atmosphere at the highest temperature of 700° C. and a retention time of 10 minutes.

An effective lifetime (µs) of the substrate for evaluations obtained above was measured with a lifetime measurement device (Semilab Japan K.K., WT-2000PVN) at room temperature (25° C.) by a microwave reflection photoconductivity decay method. The effective lifetime of a region of the obtained substrate for evaluation, at which the composition for forming a passivation layer was applied, was 203 µs.

(Measurement of Thickness of Passivation Layer)

The thickness of the passivation layer on the substrate for evaluation obtained above was measured with an interference-type film thickness meter (Filmetrics Corporation, F20 Thin Film Thickness Measurement System). The thickness of the passivation layer was 75 nm.

(Measurement of Fixed Charge Density)

A capacitor having a MIS (Metal-Insulator-Semiconductor; metal/insulator/semiconductor) structure was prepared by forming plural aluminum electrodes having a diameter of 1 mm on the passivation layer of the substrate for evaluation by vapor deposition through a metal mask.

The voltage dependency of electrostatic capacitance (C-V property) of the capacitor was measured with a commercially available prober and a commercially available LCR meter (Hewlett-Packard Company, 4275A). In a C-V curve obtained by plotting the voltage along the abscissa and the electrostatic capacitance along the ordinate, the voltage value at which the electrostatic capacitance begins to decrease as the voltage is increased ($V_{fb}$: flat band voltage) was determined, and the difference from the ideal flat band voltage in the case of not forming a passivation layer ($\Phi_{ms}$; −0.81 [V]) was calculated. Then, fixed charge density $N_f$ was calculated from the difference in flat band voltage ($V_{fb}-\Phi_{ms}$), the measured value of the electrostatic capacitance, the area of the aluminum electrode, and the elementary charge.

The fixed charge density $N_f$ is a negative value when the value of $V_{fb}-\Phi_{ms}$ is positive, i.e., $V_{fb}$ is greater than −0.81 [V]. As a result, the passivation layer exhibits a negative fixed charge.

In the passivation layer prepared in Example 1, flat band voltage $V_{fb}$ shifted from −0.81 [V] to +0.23 [V]. The fixed charge density $N_f$ was calculated from this amount of shift. As a result, it was found that the fixed charge was negative at $-3.8 \times 10^{11}$ cm$^2$.

(Preparation of Photovoltaic Cell Element)

A monocrystalline p-type semiconductor substrate (125 mm square, 200 µm in thickness) was prepared, and a textured structure was formed at a light receiving surface and at a back surface by performing alkaline etching. Then, in an atmosphere of a mixed gas of phosphorus oxychloride ($POCl_3$), nitrogen and oxygen, thermal treatment was performed at 900° C. for 20 minutes, thereby forming an n$^+$-type diffusion layer at the light receiving surface, the back surface and the side surfaces. Subsequently, side etching was performed to remove a PSG layer and an n$^+$-type diffusion layer formed at the side surface, and a PSG layer formed at the light receiving surface and a PSG layer formed at the back surface were removed with an etching solution including hydrofluoric acid. Further, another etching treatment was performed to remove an n$^+$-type diffusion layer at the back surface. Then, an anti-reflection film including silicon nitride of approximately 90 nm in thickness was formed on the n$^+$-type diffusion layer at the light receiving surface by PECVD.

Subsequently, composition for forming a passivation layer 1 as prepared above was applied onto the back surface in the form of patterns shown in FIGS. 5, 7 and 8, dried at a temperature of 150° C. for 5 minutes, and thermal treatment (sintering) was performed with a diffusion furnace (ACCURON CQ-1200, Hitachi Kokusai Electric Inc.) in an air atmosphere at the highest temperature of 700° C. and a retention time of 10 minutes, thereby forming passivation layer 1. In FIGS. 5, 7 and 8, passivation layer 1 was formed at the back surface in the form of a pattern in which the p-type semiconductor was exposed in a dotted manner, excluding the area in which a back surface power extraction electrode was to be formed in the subsequent process. The pattern of the dotted openings was the same as that used for the evaluation of print blur, and the dot diameter ($L_a$) was 368 µm and the interval ($L_b$) was 0.5 mm.

Subsequently, a commercially available silver electrode paste (PV-16A, Du Pont Kabushiki Kaisha) was applied onto the light receiving surface by screen printing in the form of a pattern shown in FIG. 4. The electrode pattern composed of a light receiving surface current collector electrode of 120 μm in width and a light receiving surface power extraction electrode of 1.5 mm in width. The printing conditions (mesh of a screen block, printing speed, and printing pressure) were adjusted such that the thickness after performing thermal treatment (sintering) was 20 μm. Then, drying treatment was performed by heating at a temperature of 150° C. for 5 minutes to evaporate a liquid medium.

On the back surface, a commercially available aluminum electrode paste (PVG-AD-02, PVG Solutions) and a commercially available silver electrode paste (PV-505, Du Pont Kabushiki Kaisha) were applied by screen printing in the form of a pattern shown in FIG. 9. The pattern of the back surface power extraction electrode formed from a silver electrode paste was 123 mm×4 mm.

Printing conditions (mesh of screen block, printing speed, and printing pressure) of a silver electrode paste and an aluminum electrode paste were adjusted such that the thickness of the back surface power extraction electrode and the back surface current collector electrode after thermal treatment (sintering) was 20 μm.

After performing printing with each of the electrode pastes, drying treatment was performed by heating at a temperature of 150° C. for 5 minutes to evaporate a liquid medium.

Subsequently, thermal treatment (sintering) was performed with a tunnel furnace (single line delivery W/B tunnel furnace, Noritake Company, Limited) in an air atmosphere at the highest temperature of 800° C. and a retention time of 10 seconds, thereby preparing photovoltaic cell element 1 on which intended electrodes were formed.

A wiring member (solder-plated flat wire for photovoltaic cell, product name: SSA-TPS 0.2×1.5 (20); plated with a Sn—Ag—Cu-based lead-free solder to a thickness up to 20 μm per either side of a copper wire of 0.2 mm in thickness and 1.5 mm in width, Hitachi Cable, Ltd.) was placed on the light receiving surface power extraction electrode and the back surface power extraction electrode of photovoltaic cell element 1 as obtained above, and the solder was melted with a tab wire stringing machine (NTS-150-M, Tabbing & Stringing Machine, NPC Incorporated) at the highest temperature of 250° C. and a retention time for 10 seconds, thereby stringing the wiring member with the light receiving surface power extraction electrode and the back surface power extraction electrode.

Figure 10:
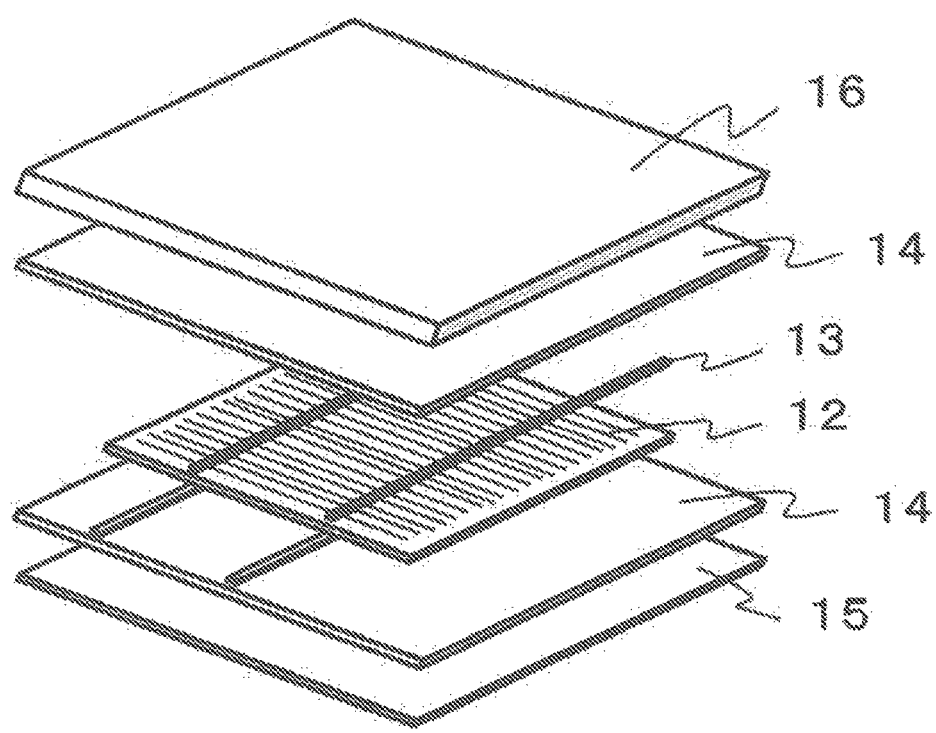
FIG. 10 shows an example of a method of producing a photovoltaic cell.

Subsequently, a laminate having a structure of a glass plate 16/sealant 14/photovoltaic cell element 12 connected with wiring material 13/sealant 14/back sheet 15 in this order, as shown in FIG. 10, was prepared using a glass plate (tempered white glass plate, 3KWE33, Asahi Glass Co., Ltd.), a sealant (ethylene vinyl acetate; EVA) and a back sheet. The laminate was subjected to vacuum lamination at a temperature of 140° C. for 5 minutes with a vacuum laminator (LM-50×50, NPC Incorporated) so that a portion of the wiring member is exposed, thereby preparing photovoltaic cell 1.

The power performance of the photovoltaic cell was evaluated with a solar simulator (WXS-155S-10, Wacom Electric Co., Ltd.) and a measuring apparatus of a voltage-current (I-V) evaluation system (I-V CURVE TRACER MP-180, Eko Instruments). The measured values of Jsc (short-circuit current), Voc (open voltage), F.F. (form factor) and η (conversion efficiency), which indicate a power generation performance as a photovoltaic cell, were obtained according to JIS-C-8913 (2005) and JIS-C-8914 (2005). The obtained values were converted to a relative value with respect to the measured values of a photovoltaic cell as prepared in Comparative Example 1 (photovoltaic cell C1) that were defined as 100.0.

Example 2

Ethyl cellulose (Nissin Kasei Co., Ltd., trade name: ETHOCEL 200 cps, abbreviated as EC) was added to the composition for forming a passivation layer prepared in Example 1.

Specifically, the composition for forming a passivation layer 2 was prepared in the same manner as Example 1, except that the content of niobium pentaethoxide (Hokko Chemical Industry Co., Ltd., structural formula: $Nb(OC_2H_5)_5$, molecular weight: 318.2) was 1.2 g, the content of terpineol was 18.5 g and the content of ethyl cellulose was 0.3 g.

Subsequently, the thixotropic property, storage stability and printability (unevenness in printing and print blur) of composition for forming a passivation layer 2, and the effective lifetime of passivation layer 2 were evaluated in the same manner as Example 1, and the thickness and the fixed charge density were measured in the same manner as Example 1. Further, photovoltaic cell element 2 and photovoltaic cell 2 were prepared and the power generation performance was evaluated in the same manner as Example 1.

Example 3

Aluminum ethylacetoacetate diisopropylate (Kawaken Fine Chemicals Co., Ltd., trade name: ALCH) was added to the composition for forming a passivation layer. Specifically, composition for forming a passivation layer 3 was prepared in the same manner as Example 1, except that the content of niobium pentaethoxide (Hokko Chemical Industry Co., Ltd., structural formula: $Nb(OC_2H_5)_5$, molecular weight: 318.22) was 1.2 g, the content of ALCH was 1.2 g and the content of terpineol was 17.6 g.

Subsequently, the thixotropic property, storage stability and printability (unevenness in printing and print blur) of composition for forming a passivation layer 3, and the effective lifetime of passivation layer 3 were evaluated in the same manner as Example 1, and the thickness and the fixed charge density were measured in the same manner as Example 1. Further, photovoltaic cell element 3 and photovoltaic cell 3 were prepared and the power generation performance was evaluated in the same manner as Example 1.

Example 4

Ethyl cellulose (ETHOCEL 200 cps) and aluminum ethylacetoacetate diisopropylate (ALCH) were added to the composition for forming a passivation layer. Specifically, composition for forming passivation layer 4 was prepared in the same manner as Example 1, except that the content of niobium pentaethoxide (Hokko Chemical Industry Co., Ltd., structural formula: $Nb(OC_2H_5)_5$, molecular weight: 318.2) was 1.6 g, the content of ALCH was 1.0 g, the content of terpineol was 17.1 g and the content of ethyl cellulose was 0.3 g.

Subsequently, the thixotropic property, storage stability and printability (unevenness in printing and print blur) of the composition for forming passivation layer 4, and the effective lifetime of passivation layer 4 were evaluated in the same manner as Example 1, and the thickness and the fixed charge density were measured in the same manner as Example 1. Further, photovoltaic cell element 4 and photovoltaic cell 4 were prepared and the power generation performance was evaluated in the same manner as Example 1.

Example 5

The composition for forming a passivation layer prepared in Example 4 was used for the evaluation. Specifically, the printability (unevenness in printing and print blur) of composition for forming a passivation layer 5, and the effective lifetime of passivation layer 5 were evaluated in the same manner as Example 1, and the thickness and the fixed charge density were measured in the same manner as Example 1, and photovoltaic cell element 5 and photovoltaic cell 5 were prepared and the power generation performance was evaluated in the same manner as Example 1, except that the conditions for the thermal treatment (sintering) for composition for forming a passivation layer 4, which was performed in the preparation of the substrate for evaluating printability (unevenness in printing and print blur), the preparation of the substrate for evaluating the effective lifetime and the thickness of the passivation layer, and the preparation of the photovoltaic cell element, were changed from 700° C. for 10 minutes to 600° C. for 15 minutes.

Example 6

The composition for forming a passivation layer prepared in Example 4 was used for the evaluation. Specifically, the printability (unevenness in printing and print blur) of composition for forming a passivation layer 6, and the effective lifetime of passivation layer 6 were evaluated in the same manner as Example 1, and the thickness and the fixed charge density were measured in the same manner as Example 1, and photovoltaic cell element 6 and photovoltaic cell 6 were prepared and the power generation performance was evaluated in the same manner as Example 1, except that the conditions for the thermal treatment (sintering) for composition for forming a passivation layer 4, which was performed in the preparation of the substrate for evaluating printability (unevenness in printing and print blur), the preparation of the substrate for evaluating the effective lifetime and the thickness of the passivation layer, and the preparation of the photovoltaic cell element, were changed from 700° C. for 10 minutes to 800° C. for 8 minutes.

Example 7

Tantalum penta-n-butoxide (Kojundo Chemical Lab. Co., Ltd., structural formula: $Ta(O-n-C_4H_9)_5$, molecular weight: 546.4) was used instead of niobium pentaethoxide. Specifically, composition for forming a passivation layer 7 was prepared in the same manner as Example 1, except that the content of tantalum penta-n-butoxide was 1.6 g, and the content of terpineol was 18.4 g.

Subsequently, the thixotropic property, storage stability and printability (unevenness in printing and print blur) of composition for forming a passivation layer 7, and the effective lifetime of passivation layer 7 were evaluated in the same manner as Example 1, and the thickness and the fixed charge density were measured in the same manner as Example 1. Further, photovoltaic cell element 7 and photovoltaic cell 7 were prepared and the power generation performance was evaluated in the same manner as Example 1.

Example 8

Aluminum ethylacetoacetate diisopropylate (Kawaken Fine Chemicals Co., Ltd., trade name: ALCH) was added to the composition for forming a passivation layer in Example 7. Specifically, composition for forming a passivation layer 8 was prepared in the same manner as Example 7, except that the content of tantalum penta-n-butoxide was 1.2 g, the content of ALCH was 1.2 g, and the content of terpineol was 17.6 g.

Subsequently, the thixotropic property, storage stability and printability (unevenness in printing and print blur) of composition for forming a passivation layer 8, and the effective lifetime of passivation layer 8 were evaluated in the same manner as Example 1, and the thickness and the fixed charge density were measured in the same manner as Example 1. Further, photovoltaic cell element 8 and photovoltaic cell 8 were prepared and the power generation performance was evaluated in the same manner as Example 1.

Example 9

Vanadium (V) triethoxide oxide (Kojundo Chemical Lab. Co., Ltd., structural formula: $VO(OC_2H_5)_3$, molecular weight: 546.4) was used in place of niobium pentaethoxide in the composition in Example 1. Specifically, composition for forming a passivation layer 9 was prepared in the same manner as Example 1, except that the content of vanadium (V) triethoxide oxide was 1.6 g and the content of terpineol was 18.4 g.

Subsequently, the thixotropic property, storage stability and printability (unevenness in printing and print blur) of composition for forming a passivation layer 9, and the effective lifetime of passivation layer 9 were evaluated in the same manner as Example 1, and the thickness and the fixed charge density were measured in the same manner as Example 1. Further, photovoltaic cell element 9 and photovoltaic cell 9 were prepared and the power generation performance was evaluated in the same manner as Example 1.

Example 10

Aluminum ethylacetoacetate diisopropylate (Kawaken Fine Chemicals Co., Ltd., trade name: ALCH) and ethyl cellulose (ETHOCEL200cps) were added to the composition for forming a passivation layer in Example 9. Specifically, composition for forming a passivation layer 10 was prepared in the same manner as Example 9, except that the content of vanadium (V) triethoxide oxide (Kojundo Chemical Lab. Co., Ltd., structural formula: $VO(OC_2H_5)_3$, molecular weight: 546.4) was 1.2 g, the content of ALCH was 0.8 g, the content of terpineol was 17.7 g and the content of ethyl cellulose was 0.3 g.

Subsequently, the thixotropic property, storage stability and printability (unevenness in printing and print blur) of composition for forming passivation layer 10, and the effective lifetime of passivation layer 10 were evaluated in the same manner as Example 1, and the thickness and the fixed charge density were measured in the same manner as Example 1. Further, photovoltaic cell element 10 and photovoltaic cell 10 were prepared and the power generation performance was evaluated in the same manner as Example 1.

Example 11

Hafnium tetra-t-butoxide (Kojundo Chemical Lab. Co., Ltd., structural formula: $Hf(O-t-C_4H_9)_4$, molecular weight:

470.9) was used in place of niobium pnetaethoxide in Example 1. Specifically, composition for forming a passivation layer 11 was prepared in the same manner as Example 1, except that the content of hafnium tetra-t-butoxide was 2.0 g and the content of terpineol was 18.0 g.

Subsequently, the thixotropic property, storage stability and printability (unevenness in printing and print blur) of composition for forming a passivation layer 11, and the effective lifetime of passivation layer 11 were evaluated in the same manner as Example 1, and the thickness and the fixed charge density were measured in the same manner as Example 1. Further, photovoltaic cell element 11 and photovoltaic cell 11 were prepared and the power generation performance was evaluated in the same manner as Example 1.

Example 12

Aluminum trisethylacetoacetate (Kawaken Fine Chemicals Co., Ltd., trade name: ALCH-TR) and ethyl cellulose (ETHOCEL 200 cps) were added to composition for forming a passivation layer in Example 11. Specifically, composition for forming a passivation layer 12 was prepared in the same manner as Example 11, except that the content of hafnium tetra-t-butoxide (Kojundo Chemical Lab. Co., Ltd., structural formula: $Hf(O-t-C_4H_9)_4$, molecular weight: 470.9) was 1.2 g, the content of ALCH-TR was 1.2 g, the content of terpineol was 17.3 g and the content of ethyl cellulose was 0.3 g.

Subsequently, the thixotropic property, storage stability and printability (unevenness in printing and print blur) of composition for forming a passivation layer 12, and the effective lifetime of passivation layer 12 were evaluated in the same manner as Example 1, and the thickness and the fixed charge density were measured in the same manner as Example 1. Further, photovoltaic cell element 12 and photovoltaic cell 12 were prepared and the power generation performance was evaluated in the same manner as Example 1.

Example 13

In the preparation of a composition for forming a passivation layer, niobium pentaethoxide (Hokko Chemical Industry Co., Ltd., structural formula: $Nb(OC_2H_5)_5$, molecular weight: 318.2), tantalum penta-n-butoxide (Kojundo Chemical Lab. Co., Ltd., structural formula: $Ta(O-n-C_4H_9)_5$, molecular weight: 546.4), terpineol and ethyl cellulose (ETHOCEL 200 cps) were used. Specifically, composition for forming a passivation layer 13 was prepared in the same manner as Example 1, except that the content of niobium pentaethoxide was 1.4 g, the content of tantalum penta-n-butoxide was 1.0 g, the content of terpineol was 17.3 g, and the content of ethyl cellulose was 0.3 g.

Subsequently, the thixotropic property, storage stability and printability (unevenness in printing and print blur) of composition for forming a passivation layer 13, and the effective lifetime of passivation layer 13 were evaluated in the same manner as Example 1, and the thickness and the fixed charge density were measured in the same manner as Example 1. Further, photovoltaic cell element 13 and photovoltaic cell 13 were prepared and the power generation performance was evaluated in the same manner as Example 1.

Example 14

In the preparation of a composition for forming a passivation layer, niobium penta-n-butoxide (Kojundo Chemical Lab. Co., Ltd., structural formula: $Nb(O-n-C_4H_9)_5$, molecular weight: 458.5), vanadium (V) triethoxide oxide (Kojundo Chemical Lab. Co., Ltd., structural formula: $VO(OC_2H_5)_3$, molecular weight: 546.4), aluminum ethylacetoacetate diisopropylate (Kawaken Fine Chemicals Co., Ltd., trade name: ALCH), terpineol and ethyl cellulose (ETHOCEL 200 cps) were used. Specifically, composition for forming a passivation layer 14 was prepared in the same manner as Example 1, except that the content of niobium penta-n-butoxide was 1.6 g, the content of vanadium (V) tri-n-propoxide oxide was 0.6 g, the content of ALCH was 0.6 g, the content of terpineol was 17.0 g, and the content of ethyl cellulose was 0.2 g.

Subsequently, the thixotropic property, storage stability and printability (unevenness in printing and print blur) of composition for forming a passivation layer 14, and the effective lifetime of a passivation layer 14 were evaluated in the same manner as Example 1, and the thickness and the fixed charge density were measured in the same manner as Example 1. Further, photovoltaic cell element 14 and photovoltaic cell 14 were prepared and the power generation performance was evaluated in the same manner as Example 1.

Comparative Example 1

In the formation of a passivation layer on a semiconductor substrate, passivation layer C1 composed of aluminum oxide ($Al_2O_3$) was formed by an ALD (Atomic Layer Deposition) method without using a composition for forming a passivation layer.

Specifically, passivation layer C1 was formed by adjusting the film formation conditions with an atomic layer deposition device such that the thickness of the $Al_2O_3$ layer was 20 nm. The thickness after the film formation was measured with an interference type film thickness meter (F20 FILM THICKNESS MEASUREMENT SYSTEM, Filmetrics Corporation).

A substrate for evaluation of effective lifetime and thickness of passivation layer C1, and photovoltaic cell element C1 and photovoltaic cell C1 were prepared by the method as described above, and the measurement of effective lifetime, thickness and fixed charge density, and the evaluation of power generation performance of photovoltaic cell C1 were performed. The semiconductor substrate, the type, the film formation pattern and the method of forming an electrode at the light receiving surface and at the back surface used for the evaluation were the same as those performed in Examples 1 to 16.

Comparative Example 2

Composition for forming a passivation layer C2 that includes bismuth triethoxide (Kojundo Chemical Lab. Co., Ltd., structural formula: $Bi(OC_2H_5)_3$, molecular weight 344.2), terpineol and ethyl cellulose (ETHOCEL 200 cps), as shown in Table 1, was prepared without using a compound of Formula (I) used in the preparation of the composition for forming a passivation layer in Example 1.

Subsequently, the thixotropic property, storage stability and printability (unevenness in printing and print blur) of the composition for forming passivation layer C2, and the effective lifetime of passivation layer C2 were evaluated in the same manner as Example 1, and the thickness and the fixed charge density were measured in the same manner as Example 1. Further, photovoltaic cell element C2 and photovoltaic cell C2 were prepared and the power generation performance was evaluated in the same manner as Example 1.

Comparative Example 3

Composition for forming a passivation layer C3 that includes titanium tetra-i-propoxide (Kojundo Chemical Lab. Co., Ltd., structural formula: $Ti(O-i-C_3H_7)_4$, molecular weight 284.2), terpineol and ethyl cellulose (ETHOCEL 200 cps), as shown in Table 1, was prepared without using a compound of Formula (I) used in the preparation of the composition for forming a passivation layer in Example 1.

Subsequently, the thixotropic property, storage stability and printability (unevenness in printing and print blur) of composition for forming a passivation layer C3, and the effective lifetime of passivation layer C3 were evaluated in the same manner as Example 1, and the thickness and the fixed charge density were measured in the same manner as Example 1. Further, photovoltaic cell element C3 and photovoltaic cell C3 were prepared and the power generation performance was evaluated in the same manner as Example 1.

Comparative Example 4

Photovoltaic cell element C4 and photovoltaic cell C4 were prepared and the power generation performance was evaluated, while not forming a passivation layer at the back surface in the preparation of a photovoltaic cell element.

Specifically, a textured structure was formed at a light receiving surface and at a back surface, and an $n^+$-type diffusion layer and an anti-reflection film of silicon nitride were formed to a thickness of approximately 90 nm at the light receiving surface by PECVD. Then, on the light receiving surface, a commercially available silver electrode paste (PV-16A, Du Pont Kabushiki Kaisha) was applied by screen printing in the form of a pattern shown in FIG. 4, and subjected to drying treatment by heating at a temperature of 150° C. for 5 minutes to evaporate a liquid medium. On the back surface, a commercially available aluminum electrode paste (PVG-AD-02, PVG Solutions) and a commercially available silver electrode paste (PV-505, Du Pont Kabushiki Kaisha) were applied by screen printing in the form of a pattern shown in FIG. 9. After the application of the electrode pastes, drying treatment was performed by heating at a temperature of 150° C. for 5 minutes to evaporate a liquid medium. The size and the printing conditions for the electrode pastes were the same as Example 1.

Subsequently, thermal treatment (sintering) was performed with a tunnel furnace (single line delivery W/B tunnel furnace, Noritake Company, Limited) in an air atmosphere at the highest temperature of 800° C. and a retention time of 10 seconds, thereby preparing photovoltaic cell element C4 in which intended electrodes were formed.

Photovoltaic cell C4 was prepared by using photovoltaic cell element C4 in the same manner as Example 1, i.e., by connecting a wiring member to the light receiving surface power extraction electrode and the back surface power extraction electrode, assembling a laminate with a glass plate, a sealant and a back sheet, and performing vacuum lamination with a laminator.

TABLE 1

| Example | Compound (1) Represented by Formula (I) | | | Compound (2) Represented by Formula (I) | | | Compound Represented by Formula (II) | |
|---|---|---|---|---|---|---|---|---|
| | M | Type | % by mass | M | Type | % by Mass | Type | % by Mass |
| Example 1 | Nb | Niobium Ethoxide | 6.0 | — | — | 0.0 | — | 0.0 |
| Example 2 | Nb | Niobium Ethoxide | 6.0 | — | — | 0.0 | — | 0.0 |
| Example 3 | Nb | Niobium Ethoxide | 6.0 | — | — | 0.0 | ALCH | 6.0 |
| Example 4 | Nb | Niobium Ethoxide | 8.0 | — | — | 0.0 | ALCH | 5.0 |
| Example 5 | Nb | Niobium Ethoxide | 8.0 | — | — | 0.0 | ALCH | 5.0 |
| Example 6 | Nb | Niobium Ethoxide | 8.0 | — | — | 0.0 | ALCH | 5.0 |
| Example 7 | Ta | Tantalum n-Butoxide | 8.0 | — | — | 0.0 | — | 0.0 |
| Example 8 | Ta | Tantalum n-Butoxide | 6.0 | — | — | 0.0 | ALCH | 6.0 |
| Example 9 | V | Vanadium Ethoxideoxide | 8.0 | — | — | 0.0 | — | 0.0 |
| Example 10 | V | Vanadium Ethoxideoxide | 6.0 | — | — | 0.0 | ALCH | 4.0 |
| Example 11 | Hf | Hafnium t-Butoxide | 10.0 | — | — | 0.0 | — | 0.0 |
| Example 12 | Hf | Hafnium t-Butoxide | 6.0 | — | — | 0.0 | ALCH-TR | 6.0 |
| Example 13 | Nb | Niobium Ethoxide | 7.0 | Ta | Tantalum n-Butoxide | 5.0 | — | 0.0 |
| Example 14 | Nb | Niobium n-Butoxide | 8.0 | V | Vanadium Ethoxideoxide | 3.0 | ALCH | 3.0 |
| Ref. Ex. 1 | — | — | — | — | — | — | — | — |
| Ref. Ex. 2 | Bi | Bismuth Ethoxide | 12.0 | — | — | 0.0 | — | 0.0 |
| Ref. Ex. 3 | Ti | Titanium i-Propoxide | 10.0 | — | — | 0.0 | — | 0.0 |
| Ref. Ex. 4 | — | — | — | — | — | — | — | — |

| Example | Solvent | | Resin | | Composition for Passivation Film | Thermal treatment (Sintering) Conditions | |
|---|---|---|---|---|---|---|---|
| | Type | % by Mass | Type | % by Mass | | Temp [° C.] | Time [min] |
| Example 1 | TPO | 94.0 | — | 0.0 | Composition 1 | 700 | 10 |
| Example 2 | TPO | 92.5 | EC | 1.5 | Composition 2 | 700 | 10 |
| Example 3 | TPO | 88.0 | — | 0.0 | Composition 3 | 700 | 10 |
| Example 4 | TPO | 85.5 | EC | 1.5 | Composition 4 | 700 | 10 |

TABLE 1-continued

|  |  |  |  |  |  |  |  |
|---|---|---|---|---|---|---|---|
| Example 5 | TPO | 85.5 | EC | 1.5 | Composition 4 | 600 | 15 |
| Example 6 | TPO | 85.5 | EC | 1.5 | Composition 4 | 800 | 8 |
| Example 7 | TPO | 92.0 | — | 0.0 | Composition 7 | 700 | 10 |
| Example 8 | TPO | 88.0 | — | 0.0 | Composition 8 | 700 | 10 |
| Example 9 | TPO | 92.0 | — | 0.0 | Composition 9 | 700 | 10 |
| Example 10 | TPO | 88.5 | EC | 1.5 | Composition 10 | 700 | 10 |
| Example 11 | TPO | 90.0 | — | 0.0 | Composition 11 | 700 | 10 |
| Example 12 | TPO | 85.5 | EC | 1.5 | Composition 12 | 700 | 10 |
| Example 13 | TPO | 86.5 | EC | 1.5 | Composition 13 | 700 | 10 |
| Example 14 | TPO | 83.0 | EC | 1.0 | Composition 14 | 700 | 10 |
| Ref. Ex. 1 | — | — | — | — | — | — | — |
| Ref. Ex. 2 | TPO | 86.0 | EC | 2.0 | Composition C2 | 700 | 10 |
| Ref. Ex. 3 | TPO | 88.5 | EC | 1.5 | Composition C3 | 700 | 10 |
| Ref. Ex. 4 | — | — | — | — | — | — | — |

TABLE 2

| Example | Composition for Passivation on Film | Properties of Composition for Passivation Film | | | | Evaluation of Printability | | | |
|---|---|---|---|---|---|---|---|---|---|
| | | Shear Viscosity (1 S$^{-4}$) [Pa·s] | Shear Viscosity (10 S$^{-4}$) [Pa·s] | Thixotropic Property | Storage Stability | Substrate A (Mirror) | | Substrate B (Texture) | |
| | | | | | | Unevenness in Printing | Print Blur | Unevenness in Printing | Print Blur |
| Example 1 | 1 | 22.3 | 18.9 | 1.18 | A | A | A | B | B |
| Example 2 | 2 | 35.4 | 26.8 | 1.32 | A | A | A | A | A |
| Example 3 | 3 | 23.0 | 20.8 | 1.11 | A | A | A | B | B |
| Example 4 | 4 | 37.5 | 27.0 | 1.39 | A | A | A | A | A |
| Example 5 | 4 | 37.5 | 27.0 | 1.39 | A | A | A | A | A |
| Example 6 | 4 | 37.5 | 27.0 | 1.39 | A | A | A | A | A |
| Example 7 | 7 | 24.3 | 19.4 | 1.25 | A | A | A | B | B |
| Example 8 | 8 | 27.4 | 20.5 | 1.34 | A | A | A | B | B |
| Example 9 | 9 | 29.7 | 25.9 | 1.10 | B | A | A | B | B |
| Example 10 | 10 | 33.1 | 28.5 | 1.16 | B | A | A | B | A |
| Example 11 | 11 | 22.1 | 18.3 | 1.21 | B | A | A | B | B |
| Example 12 | 12 | 37.5 | 30.3 | 1.24 | A | A | A | A | A |
| Example 13 | 13 | 25.6 | 19.9 | 1.29 | A | A | A | A | B |
| Example 14 | 14 | 37.0 | 29.7 | 1.25 | A | A | A | A | A |
| Com. Ex. 1 | — | — | — | — | — | — | — | — | — |
| Com. Ex. 2 | C2 | 41.3 | 30.5 | 1.35 | B | A | A | A | A |
| Com. Ex. 3 | C3 | 23.1 | 18.8 | 1.23 | B | A | A | A | B |
| Com. Ex. 4 | — | — | — | — | — | — | — | — | — |

| Example | Effective Lifetime [μs] | Film Thickness after Thermal treatment (Sintering) [nm] | Fixed Charge Density [cm$^{-2}$] | Performance of Photovoltaic Cell | | | |
|---|---|---|---|---|---|---|---|
| | | | | Short-Circuit Current Jsc (Relative Value) | Open Voltage Vac (Relative Value) | Form Factor FF (Relative Value) | Conversion Efficiency η (Relative Value) |
| Example 1 | 203 | 75 | −3.5E+11 | 99.2 | 100.3 | 99.3 | 99.2 |
| Example 2 | 198 | 74 | −8.9E+11 | 101.3 | 100.3 | 100.9 | 100.4 |
| Example 3 | 480 | 66 | −7.5E+11 | 103.4 | 103.5 | 102.8 | 103.6 |
| Example 4 | 475 | 70 | −9.8E+11 | 103.4 | 102.8 | 102.0 | 103.5 |
| Example 5 | 420 | 73 | −8.6E+11 | 102.4 | 101.9 | 102.4 | 103.1 |
| Example 6 | 466 | 65 | −3.4E+12 | 103.5 | 100.8 | 101.5 | 101.4 |
| Example 7 | 188 | 69 | −3.4E+10 | 98.5 | 95.6 | 98.4 | 98.2 |
| Example 8 | 244 | 71 | −4.5E+11 | 100.2 | 100.4 | 99.8 | 99.9 |
| Example 9 | 177 | 80 | −2.0E+10 | 97.5 | 96.4 | 96.1 | 94.3 |
| Example 10 | 247 | 77 | −9.7E+10 | 100.3 | 100.4 | 101.0 | 100.2 |
| Example 11 | 188 | 80 | −1.3E+10 | 97.4 | 96.5 | 97.2 | 96.9 |
| Example 12 | 256 | 73 | −2.4E+11 | 99.3 | 99.4 | 98.7 | 99.2 |
| Example 13 | 276 | 77 | −8.0E+11 | 100.4 | 101.3 | 101.0 | 100.8 |
| Example 14 | 492 | 72 | −2.3E+12 | 104.3 | 103.4 | 102.7 | 103.0 |
| Com. Ex. 1 | 305 | 21 | −2.4E+12 | 100.0 | 100.0 | 100.0 | 100.0 |
| Com. Ex. 2 | 36 | 560 | 5.3E+09 | 45.0 | 50.2 | 56.5 | 55.4 |
| Com. Ex. 3 | 18 | 100 | 4.7E+09 | 38.2 | 52.0 | 52.1 | 48.9 |
| Com. Ex. 4 | — | — | — | 95.4 | 90.3 | 94.6 | 93.2 |

The results of the evaluation of shear viscosity, thixotropic property and storage stability of the compositions for forming a passivation layer, the evaluation of printability, the measurement of lifetime and thickness, and the evaluation of power generation performance of the photovoltaic cells, as performed in Examples 1 to 14 and Comparative Examples 1 to 4, are shown in Table 2.

The compositions for a passivation layer prepared in Examples 1 to 14 exhibited a favorable storage stability and a favorable printability. In the evaluation of print blur in printability, the composition for forming a passivation layer including a resin (ethyl cellulose) exhibited a favorable result, as compared with the other examples.

In addition, the effective lifetime and power generation performance of a photovoltaic cell evaluated in Examples 1 to 14 were almost the same as those measured in Comparative Example 1, showing that a passivation layer having a passivation effect that was comparable to that of aluminum oxide ($Al_2O_3$) formed by an ALD method was formed by using the composition for forming a passivation layer of the invention. The result of the measurement of the fixed charge density showed that the passivation layers prepared in Examples 1 to 14 exhibited a negative fixed charge, although the values were different thereamong.

The power generation performance of the photovoltaic cell tended to be relatively higher when the composition for forming a passivation layer included a resin (ethyl cellulose). The reason for this is considered to be, as described above, that the printability is improved (print blur is suppressed) and the size of a dot diameter ($L_a$) that defines the pattern of a passivation layer in the fabrication of a photovoltaic cell is maintained, and the percentage of the contact area between an aluminum electrode paste and a semiconductor substrate is maintained, as a result of including a resin in the composition for forming a passivation layer.

However, it is thought that an effect to the power generation performance of the print blur is reduced by employing, for example, a method of applying a composition for forming a passivation layer onto an entire area of the back surface and, after performing thermal treatment (sintering), removing the passivation layer in the form of a desired pattern, instead of a screen printing method as used in the Examples. Accordingly, as is seen in the Examples, it is thought that the occurrence of print blur per se would not cause a reduction in the power generation of a photovoltaic cell.

In addition, the power generation performance of the photovoltaic cell tends to become relatively higher in the case in which the composition for forming a passivation layer includes a compound of Formula (I) and an organic aluminum compound. It is thought that, by including a compound of Formula (I) and an organic aluminum compound in the composition for forming a passivation layer, for example, a composite oxide of a metal derived from a compound of Formula (I) and aluminum is formed by performing thermal treatment (sintering), and a passivation layer that is denser and greater in negative fixed charge is formed, thereby further improving a passivation layer.

The results of Examples 13 and 14 showed that in a case in which two kinds of Formula (I) compounds also exhibited a high passivation effect and contributed to an increase in the power generation performance of a photovoltaic cell.

The power generation performance of a photovoltaic cell prepared in Comparative Examples 2 and 3 was lower than Comparative Example 1 and Examples 1 to 14. As is seen from the measurement result of the fixed charge density, it is thought that a greater value of a fixed charge was generated from an oxide, i.e., bismuth oxide ($Bi_2O_3$) and titanium oxide ($TiO_2$, TiO, or the like) that was formed by performing thermal treatment (sintering) to the composition for forming a passivation layer C2 of Comparative Example 2, in which triethoxy bismuth was used, or the composition for forming a passivation layer C3 of Comparative Example 3, in which titanium tetra-i-propoxide was used, and therefore a sufficient passivation effect was not obtained.

The power generation performance of a photovoltaic cell prepared in Comparative Example 4 was lower than that in Comparative Example 1 and Examples 1 to 14. The reason for this is thought to be that aluminum was diffused at an entire area of the back surface of the semiconductor substrate during performing thermal treatment (sintering) after applying an aluminum electrode paste to the back surface, thereby increasing back surface recombination of minority carriers generated in a photovoltaic cell, as a result of not forming a passivation layer.

Reference Embodiment 1

A passivation film, an application material, a photovoltaic cell element, and a silicon substrate having a passivation film of Reference Embodiment 1 are hereinafter described.

<1> A passivation film that comprises aluminum oxide and niobium oxide and is used for a photovoltaic cell element having a silicon substrate.

<2> The passivation film according to <1>, wherein a mass ratio of the niobium oxide to the aluminum oxide (niobium oxide/aluminum oxide) is from 30/70 to 90/10.

<3> The passivation film according to <1> or <2>, wherein a total content of the niobium oxide and the aluminum oxide is 90% by mass or more.

<4> The passivation film according to any one of from <1> to <3>, further comprising an organic component.

<5> The passivation film according to any one of from <1> to <4>, which is a thermally-treated product of an application material comprising an aluminum oxide precursor and a niobium oxide precursor.

<6> An application material that comprises an aluminum oxide precursor and a niobium oxide precursor, and is used for formation of a passivation film of a photovoltaic cell element having a silicon substrate.

<7> A photovoltaic cell element that comprises:
 a p-type silicon substrate that comprises monocrystalline silicon or polycrystalline silicon, and has a light receiving surface and a back surface that is opposite to the light receiving surface;
 an n-type impurity diffusion layer that is formed on the light receiving surface of the silicon substrate;
 a first electrode that is formed on the n-type impurity diffusion layer of the light receiving surface of the silicon substrate;
 a passivation film that is formed on the back surface of the silicon substrate, the passivation film having plural openings and comprising aluminum oxide and niobium oxide; and
 a second electrode that is electrically connected to the back surface of the silicon substrate through the plural openings.

<8> A photovoltaic cell element that comprises:
 a p-type silicon substrate that comprises monocrystalline silicon or polycrystalline silicon, and has a light receiving surface and a back surface that is opposite to the light receiving surface;
 an n-type impurity diffusion layer that is formed on a light receiving surface of the silicon substrate;

a first electrode that is formed on a surface of the n-type impurity diffusion layer of the light receiving surface of the silicon substrate;

a p-type impurity diffusion layer formed on a portion or on the area of the back surface of the silicon substrate, and doped with an impurity at a higher concentration than the silicon substrate;

a passivation film that is formed on the back side surface of the silicon substrate, the passivation film having plurality openings and including aluminum oxide and niobium oxide; and a second electrode that is electrically connected to the back side surface of the p-type impurity diffusion layer of the silicon substrate through the plural openings.

<9> A photovoltaic cell element that comprises:

an n-type silicon substrate that comprises monocrystalline silicon or polycrystalline silicon and has a light receiving surface and a back surface that is opposite to the light receiving surface;

a p-type impurity diffusion layer that is formed on the light receiving surface of the silicon substrate;

a second electrode that is formed on the back surface of the silicon substrate;

a passivation film that is formed on the light receiving surface of the silicon substrate, the passivation film having plural openings and including aluminum oxide and niobium oxide; and a first electrode that is formed on the light receiving surface of the p-type impurity diffusion layer of the silicon substrate, and forms electrical connection with a surface at the light receiving side of the silicon substrate.

<10> The photovoltaic cell element according to any one of from <7> to <9>, wherein a mass ratio of niobium oxide to aluminum oxide (niobium oxide/aluminum oxide) in the passivation film is from 30/70 to 90/10.

<11> The photovoltaic cell element according to any one of from <7> to <10>, wherein a total content of the niobium oxide and the aluminum oxide in the passivation film is 90% by mass or more.

<12> A silicon substrate having a passivation film that comprises:

a silicon substrate; and the passivation film according to any one of from <1> to <5> that is provided on an entire or partial surface of the silicon substrate.

According to the Reference Embodiment, a passivation film that can extend the carrier lifetime of a silicon substrate and has a negative fixed charge can be attained at low cost. Further, an application material for forming the passivation film can be provided. Further, a photovoltaic cell element that has the passivation film and exhibits a high efficiency can be attained at low cost. Further, a silicon substrate having a passivation film that extends the carrier lifetime and has a negative fixed charge can be attained at low cost.

The passivation film of the present embodiment is a passivation film used for a silicon photovoltaic cell element, and includes aluminum oxide and niobium oxide.

In the present embodiment, the amount of the fixed charge of the passivation film can be controlled by changing the composition of the passivation film.

From the viewpoint of stabilizing a negative fixed charge, the mass ratio of niobium oxide and aluminum oxide is preferably from 30/70 to 80/20. From the viewpoint of further stabilizing a negative fixed charge, the mass ratio of niobium oxide and aluminum oxide is more preferably from 35/65 to 70/30. From the viewpoint of achieving both an improvement in carrier lifetime and a negative fixed charge, the mass ratio of niobium oxide and aluminum oxide is preferably from 50/50 to 90/10.

The mass ratio of niobium oxide and aluminum oxide in the passivation film can be measured by energy dispersive X-ray spectrometry (EDX), secondary ion mass spectrometry (SIMS) and induced coupled plasma-mass spectrometry (ICP-MS). Specific conditions for the measurement are as follows. A passivation film is dissolved in an acid or an alkaline aqueous solution, and the resulting solution is atomized and introduced in an Ar plasma. Then, a light that is released when an excited element returns to the ground state is dispersed, and its wavelength and intensity are measured. Then, qualitative analysis of the element is performed from the resulting wavelength, and quantitative analysis is performed from the resulting intensity.

The total content of niobium oxide and aluminum oxide in the passivation film is preferably 80% by mass or more, more preferably 90% by mass or more, from the viewpoint of maintaining favorable properties. The more the content of niobium oxide and aluminum oxide in the passivation film is, the greater the effect of the negative fixed charge is.

The total content of niobium oxide and aluminum oxide in the passivation film can be measured by thermogravimetric analysis, fluorescent X-ray analysis, ICP-MS, and X-ray absorption spectroscopy in combination. Specific conditions for the measurement are as follows. The proportion of an inorganic component is calculated by thermogravimetric analysis, the proportion of niobium and aluminum is calculated by fluorescent X-ray or ICP-MS analysis, and the proportion of an oxide is determined by X-ray absorption spectroscopy.

From the viewpoint of improving the film quality and adjusting the elasticity, the passivation film may include a component other than niobium oxide and aluminum oxide as an organic component. The existence of an organic component in the passivation film can be confirmed by elemental analysis and FT-IR measurement of the film.

The content of an organic component in the passivation film is more preferably less than 10% by mass, still more preferably less than 5% by mass or less, especially preferably 1% by mass or less, in the passivation film.

The passivation film may be obtained as a thermally-treated product of an application material that includes an aluminum oxide precursor and a niobium oxide precursor. The details of the application material are described below.

The application material of the present embodiment includes an aluminum oxide precursor and a niobium oxide precursor, and is used for the formation of a passivation film for a photovoltaic cell element having a silicon substrate.

The aluminum oxide precursor is not particularly limited so long as it can produce an aluminum oxide. As an aluminum oxide precursor, an organic aluminum oxide precursor is preferably used in view of dispersing aluminum oxide onto a silicon substrate in a uniform manner, and chemical stability. Examples of the organic aluminum oxide precursor include an aluminum triisopropoxide (structural formula: $Al(OCH(CH_3)_2)_3$, Kojundo Chemical Lab. Co., Ltd., SYM-AL04.

The niobium oxide precursor is not particularly limited so long as it produces niobium oxide. As a niobium oxide precursor, an organic niobium oxide precursor is preferably used from the viewpoint of dispersing the niobium oxide precursor onto a silicon substrate in a uniform manner and chemical stability. Examples of the organic niobium oxide precursor include niobium (V) ethoxide (structural formula: $Nb(OC_2H_5)_5$, molecular weight: 318.21), Kojundo Chemical Lab. Co., Ltd., Nb-05.

The application material including an organic-based niobium oxide precursor and an organic-based aluminum oxide precursor may be used to obtain a passivation film by forming a film by coating or printing, and removing an organic component by the subsequent thermal treatment (sintering). Therefore, as a result, the passivation film may include an organic component.

<Description of Structure of Photovoltaic Cell Element>

The structure of a photovoltaic cell element of the embodiment will be illustrated by referring to FIGS. 12 to 15. FIGS. 12 to 15 are cross sectional views of first to fourth structural examples in which a passivation film is provided at a back surface of the embodiment.

Silicon substrate used in this embodiment (a crystalline silicon substrate, a semiconductor substrate) 101 may be either monocrystalline silicon or polycrystalline silicon. Further, silicon substrate 101 may be either crystalline silicon having a p-type conductivity or crystalline silicon having an n-type conductivity. From the viewpoint of exhibiting an effect of the embodiment, a crystalline silicon having a p-type conductivity is more suitable.

In FIGS. 12 to 15, an example in which a p-type monocrystalline silicon as silicon substrate 101 is used is illustrated. The type of the monocrystalline silicon or polycrystalline silicon used for silicon substrate 101 is not particularly limited, but a monocrystalline silicon or a polycrystalline silicon having a resistivity of from 0.5 Ω·cm to 10 Ω·cm is preferred.

Figure 12:
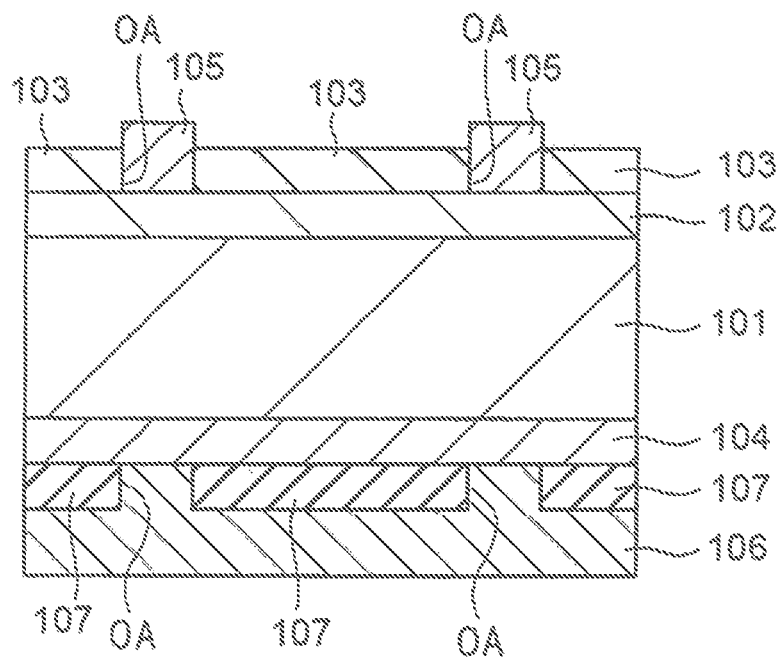
FIG. 12 is a cross sectional view of a first constitutional example of a photovoltaic cell element according to a reference embodiment.

As shown in FIG. 12 (first structural example), n-type diffusion layer 102 doped with a V-group element such as phosphorus is formed at a light receiving surface (upper side in the drawing, a first surface) of p-type silicon substrate 101. Then, a pn conjunction is formed between silicon substrate 101 and diffusion layer 102. On a surface of diffusion layer 102, light receiving surface anti-reflection film 103 such as a silicon nitride (SiN) film, and first electrode 105 (an electrode formed at the light receiving surface, a first electrode, a top electrode or a light receiving surface electrode) of silver (Ag) or the like are formed. Light receiving surface anti-reflection film 103 may function as a passivation film of a light receiving surface. By using a SiN film, the film can function as an anti-reflection film of a light receiving surface and function as a passivation film of a light receiving surface, respectively.

The photovoltaic cell element of the embodiment may have light receiving surface anti-reflection film 103, or may not. At the light receiving surface of a photovoltaic cell element, it is preferred to form a concave-convex structure (textured structure) in order to reduce the reflectivity at the surface. However, a photovoltaic cell element of the embodiment may not have a textured structure.

At the back surface (lower side in the drawing, second surface or a back surface) of silicon substrate 101, BSF (Back Surface Field) layer 104, which is a layer doped with a III-group element such as aluminum or boron, is formed. However, the photovoltaic cell element of the embodiment may include BSF layer 104, or may not.

At the back surface of silicon substrate 101, second electrode 106 (a back surface electrode, a second electrode or a back surface electrode) formed of aluminum or the like is formed in order to achieve a contact (electrical contact) with BSF layer 104 (or the back surface of silicon substrate 101 when BSF layer 104 is not formed).

In addition, FIG. 12 (first constitutional example), passivation film (a passivation layer) 107 that includes aluminum oxide and niobium oxide is formed at an area excluding a contact region (opening OA) at which BSF layer 104 (or back side surface of the silicon substrate 101 when BSF layer 104 is not formed) and second electrode 106 are electrically connected. Passivation film 107 of the present embodiment may have a negative fixed charge. By this fixed charge, electrons that correspond to minority carriers among those generated in silicon substrate 101 by light are reflected toward the surface side. Therefore, it is expected that a short-circuit current is increased and an incident photon-to-current conversion efficiency is improved.

Figure 13:
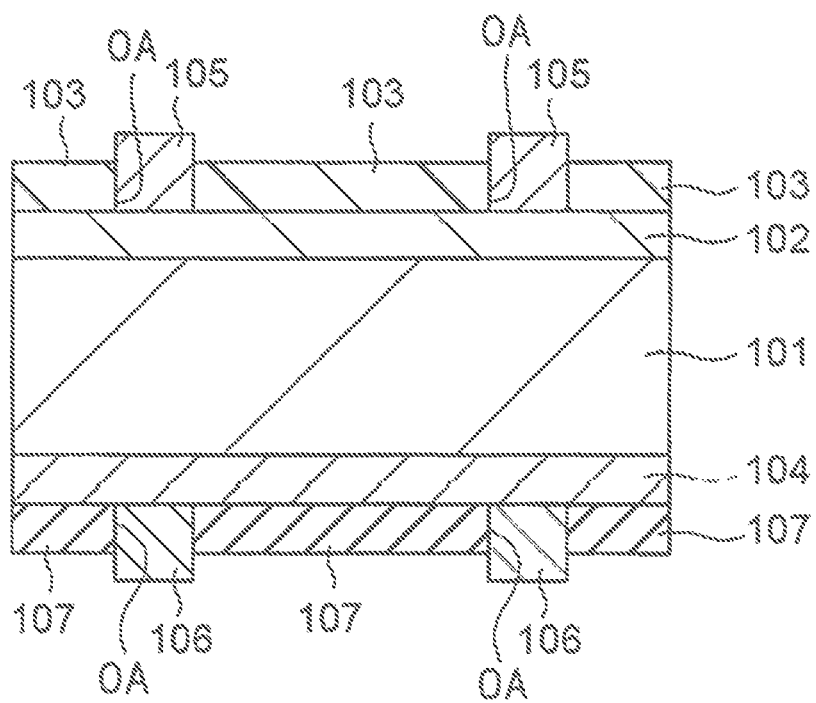
FIG. 13 is a cross sectional view of a second constitutional example of a photovoltaic cell element according to a reference embodiment.

Next, a second constitutional example shown in FIG. 13 will be explained. In FIG. 12 (first constitutional example), second electrode 106 is formed at a contact region (an opening OA) and at an entire surface of passivation film 107. In FIG. 13 (second constitutional example), second electrode 106 is formed only at a contact region (opening OA). It is also possible that second electrode 106 is formed at a contact region (opening OA) and at a portion of passivation film 107. With the photovoltaic cell element having a constitution shown in FIG. 13, a similar effect to the photovoltaic cell element shown in FIG. 12 (first constitutional example) can be obtained.

Figure 14:
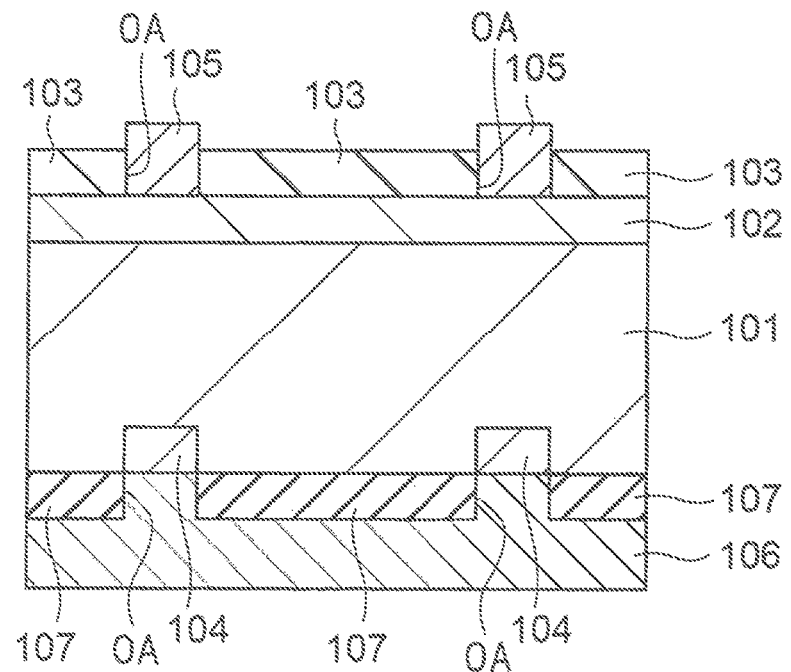
FIG. 14 is a cross sectional view of a third constitutional example of a photovoltaic cell element according to a reference embodiment.

Subsequently, a third constitutional example shown in FIG. 14 will be explained. In the third constitutional example shown in FIG. 14, BSF layer 104 is formed only at a portion of a back surface including a contact region (opening OA) with second electrode 106, rather than at an entire area of the back surface as shown in FIG. 12 (first constitutional example). A photovoltaic cell element having a constitution as described above (FIG. 14) can exhibit a similar effect to the photovoltaic cell element shown in FIG. 12 (first constitutional example). Further, in the photovoltaic cell element of the third constitutional example as shown in FIG. 14, since the area of BSF layer 104, i.e., the region that is doped with an impurity such as a third group element such as aluminum or boron at a higher concentration than that of silicon substrate 101 is small. Therefore, it is possible to obtain a higher incident photon-to-current conversion efficiency than the photovoltaic cell element shown in FIG. 12 (first constitutional example).

Figure 15:
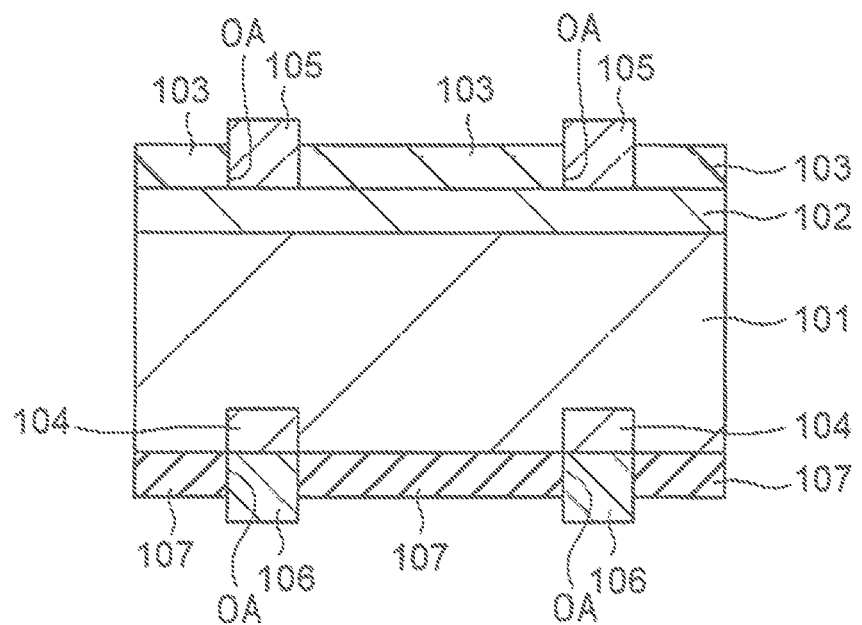
FIG. 15 is a cross sectional view of a fourth constitutional example of a photovoltaic cell element according to a reference embodiment.

Subsequently, a fourth constitutional example shown in FIG. 15 will be explained. In FIG. 14 (third constitutional example), second electrode 106 is formed at a contact region (opening OA) and at an entire surface of passivation film 107. In FIG. 15 (fourth constitutional example), second electrode 106 is formed only at a contact region (opening OA). Second electrode 106 may be formed at the contact region (opening OA) and at a portion of passivation film 107. With a photovoltaic cell element shown in FIG. 15, a similar effect to the photovoltaic cell element shown in FIG. 14 (third constitutional example) can be obtained.

In the case in which second electrode 106 is formed at an entire back surface by printing and sintering at high temperature, a convex warpage tends to occur as the temperature decreases. Such a warpage may cause a damage to a photovoltaic cell element and affect the production yield. Further, as the thickness of a silicon substrate becomes smaller, the problem associated with a warpage becomes greater. The warpage is caused by a stress generated by contraction of second electrode 106 including a metal (such as aluminum) that is greater than that of a silicon substrate, which occurs during the temperature decrease because of its greater thermal expansion coefficient than that of the silicon substrate.

As described above, it is preferred not to form second electrode 106 on an entire area of the back surface, as is shown in FIG. 13 (second constitutional example) and FIG. 15 (fourth constitutional example), because the electrode structures at the upper and lower sides tend to be symmetry and a stress caused by a difference in the thermal expansion coefficient is less likely to occur. In that case, however, it is preferred to provide an anti-reflection layer.

<Description of Method of Producing Photovoltaic Cell Element>

Subsequently, an example of a method for producing a photovoltaic cell element of this embodiment having a constitution as described above (FIGS. 12 to 15) will be explained. However, this embodiment is not limited to a photovoltaic cell element that is prepared by the method described below.

First, a textured structure is formed at a surface of silicon substrate 101, as shown in FIG. 12, for example. The textured structure may be formed at both sides of silicon substrate 101, or only at one side (a light receiving surface side) of silicon substrate 101. In order to form a textured structure, silicon substrate 101 is immersed in a heated solution of potassium hydroxide or sodium hydroxide to remove a damaged layer of silicon substrate 101. Subsequently, by immersing silicon substrate 101 in a solution including potassium hydroxide and isopropyl alcohol as major components, a textured structure is formed at both sides or at one side (a light receiving surface side) of silicon substrate 101. As described above, this process may be omitted because the photovoltaic cell element of this embodiment may have a textured structure or may not.

Subsequently, after washing silicon substrate 101 with a solution of hydrochloric acid, hydrofluoric acid or the like, a phosphorus diffusion layer ($n^+$ layer) is formed as diffusion layer 102 on silicon substrate 101 by performing thermal diffusion of phosphorus oxychloride ($POCl_3$) or the like. The phosphorus diffusion layer may be formed by, for example, applying an application-type doping material solution containing phosphorus to silicon substrate 101 and performing thermal treatment. After the thermal treatment, by removing the phosphorus glass layer formed at a surface with an acid such as hydrofluoric acid, a phosphorus diffusion layer ($n^+$ layer) is formed as diffusion layer 102. The method of forming a phosphorus diffusion layer is not particularly limited. It is preferred to form a phosphorus diffusion layer such that the depth is in the range of from 0.2 μm to 0.5 μm from the surface of silicon substrate 101, and the sheet resistance is in the range of from 40 Ω/square to 100 Ω/square (ohm/square).

Subsequently, BSF layer 104 is formed at a back surface by applying an application doping material solution including boron, aluminum or the like at a back surface of silicon substrate 101 and performing thermal treatment. For the application, a method such as screen printing, ink-jetting, dispensing and spin coating may be used. After the thermal treatment, BSF layer 104 is formed by removing a layer of boron glass, aluminum or the like that is formed at the back surface with hydrofluoric acid, hydrochloric acid or the like. The method of forming BSF layer 104 is not particularly limited. Preferably, BSF layer 104 is formed such that the concentration of boron, aluminum or the like is in the range of from $10^{18}$ $cm^{-3}$ to $10^{22}$ $cm^{-3}$, and BSF layer 104 is formed in the form of a dot or a line. Since the photovoltaic cell element of this embodiment may include BSF layer 104 or may not, this process may be omitted.

Further, when both diffusion layer 102 at the light receiving surface, and BSF layer 104 at the back surface are formed with an application solution of a doping material, it is possible to apply the doping material solution onto both sides of silicon substrate 101, form a phosphorus diffusion layer ($n^+$ layer) as diffusion layer 102 and BSF layer 104 at one process, and then remove phosphorus glass, boron glass, or the like formed on the surface at one process.

Subsequently, a silicon nitride film, which is light receiving surface anti-reflection film 103, is formed on diffusion layer 102. The method of forming light receiving surface anti-reflection film 103 is not particularly limited. It is preferred to form light receiving surface anti-reflection film 103 such that the thickness is in the range of from 50 to 100 nm, and the refractive index is in the range of from 1.9 to 2.2. Light receiving surface anti-reflection film 103 is not limited to a silicon nitride film, and may be a silicon oxide film, an aluminum oxide film, a titanium oxide film or the like. Light receiving surface anti-reflection film 103 such as a silicon nitride film may be formed by plasma CVD, thermal CVD or the like, and is preferably formed by plasma CVD that can be performed at a temperature range of from 350° C. to 500° C.

Subsequently, passivation film 107 is formed at the back surface of silicon substrate 101. Passivation film 107 includes aluminum oxide and niobium oxide, and is formed by, for example, applying a material including an aluminum oxide precursor represented by a metal-organic-decomposition application material that produces aluminum oxide upon thermal treatment (burning), and a niobium oxide precursor represented by a commercially available metal-organic-decomposition application material, from which niobium oxide is obtained upon thermal treatment (sintering) (a passivation material) and performing thermal treatment (sintering).

Passivation film 107 may be formed by a process as described below, for example. The application material is applied by spin coating onto one side of a p-type silicon substrate (from 8 Ωcm to 12 Ωcm) of 8 inches (20.32 cm) with a thickness of 725 μm, from which a spontaneously oxidized film had been removed in advance with hydrofluoric acid at a concentration of 0.049% by mass. Then, the silicon substrate is placed on a hot plate and pre-baked at 120° C. for 3 minutes. Subsequently, thermal treatment is performed at 650° C. for an hour in a nitrogen atmosphere. In that case, a passivation film including aluminum oxide and niobium oxide is obtained. The film thickness of passivation film 107 formed by the above method as measured with an ellipsometer is generally approximately several ten nm.

The above application material is applied by printing such as screen printing, offset printing, ink-jet printing, or with a dispenser, in the form of a predetermined pattern including a contact region (opening OA). Passivation film 107 (oxide film) is preferably formed by evaporating a solvent by performing pre-baking to the application material in a temperature range of 80° C. to 180° C. after application thereof, and performing thermal treatment (annealing) in a nitrogen atmosphere or an air atmosphere at a temperature of from 600° C. to 1000° C. for approximately 30 minutes to approximately 3 hours.

Opening (opening for contact) OA is preferably formed on BSF layer 104 in the form of a dot or a line.

Passivation film 107 used for the photovoltaic cell element as described above preferably has a mass ratio of niobium oxide and aluminum oxide (niobium oxide/aluminum oxide) of from 30/70 to 90/10, more preferably from 30/70 to 80/20, even more preferably from 35/65 to 70/30. By satisfying this range, a negative fixed charge can be stabilized. From the viewpoint of attaining both improvement in carrier lifetime and a negative fixed charge, the mass ratio of niobium oxide and aluminum oxide is preferably from 50/50 to 90/10.

Further, passivation film 107 preferably has a total content of niobium oxide and aluminum oxide of 80% by mass or more, more preferably 90% by mass or more.

Subsequently, first electrode 105, which is formed at the light receiving surface side, is formed. First electrode 105 is formed by applying a paste mainly composed of silver (Ag) onto light receiving surface anti-reflection film 103 by screen printing, and performing thermal treatment (fire through). The shape of first electrode 105 may be any form, such as a known shape formed of a finger electrode and a bus bar electrode.

Then, second electrode 106, which is a back surface electrode, is formed. Second electrode 106 may be formed by applying a paste mainly composed of aluminum by screen printing or with a dispenser, and subjecting the paste to thermal treatment. The shape of second electrode 106 is preferably the same shape as that of BSF layer 104, a shape covering the entire back surface, a comb-shape, a lattice-shape, or the like. It is also possible to perform printing of the paste for forming first electrode 105, which is an electrode formed at the light receiving surface side, and perform printing of the paste for forming second electrode 106, and subsequently performing thermal treatment (sintering) to form first electrode 105 and second electrode 106 at one process.

By using a paste mainly composed of aluminum (Al) for the formation of second electrode 106, aluminum diffuses as a dopant and BSF layer 104 is formed at a contact portion of second electrode 106 and silicon substrate 101 by self-aligning. As mentioned previously, BSF layer 104 may be formed separately by applying an application solution of a doping material containing boron, aluminum or the like, and subjecting the same to thermal treatment.

In the above description, although a p-type silicon is used as silicon substrate 101 in the structural and production examples, an n-type silicon may be used as silicon substrate 101. In that case, diffusion layer 102 is formed as a layer doped with a III-group element such as boron, and BSF layer 104 is formed by doping a V-group element such as phosphorus. However, it should be noted that there are cases in which a leakage current flows through a portion at which an inversion layer formed at an interface by a negative fixed charge contacts a metal at the back surface side, and it is difficult to increase conversion efficiency.

Figure 16:
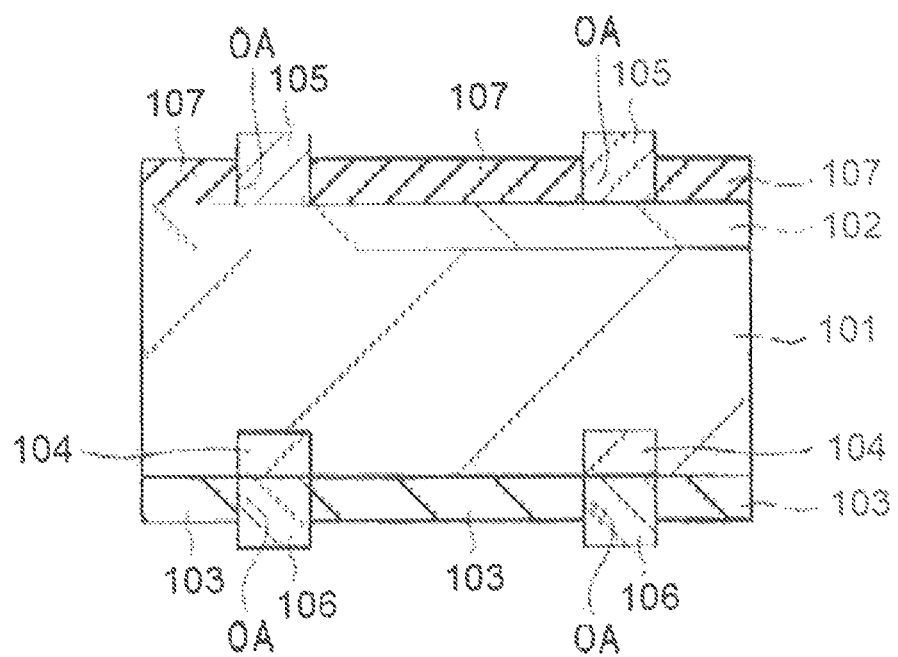
FIG. 16 is a cross sectional view of another constitutional example of a photovoltaic cell element according to a reference embodiment.

In a case in which an n-type silicon substrate is used, passivation film 107 that includes niobium oxide and aluminum oxide can be used at the light receiving surface, as shown in FIG. 16. FIG. 16 shows a constitutional example of a photovoltaic cell element in which a light receiving surface passivation film of the present embodiment is used.

In that case, diffusion layer 102 formed at the light receiving surface is converted to p-type by doping with boron, and among the generated carriers, holes are collected at the light receiving surface side and electrons are collected at the back surface side. Therefore, passivation film 107, which has a negative fixed charge, is preferably formed at the light receiving surface side.

On the passivation film that includes niobium oxide and aluminum oxide, an anti-reflection film composed of SiN or the like may be further formed by CVD or the like.

In the following, details of the present embodiment will be explained by referring to the Reference Examples and the Comparative Examples.

Reference Example 1-1

Passivation material (a-1) as an application material was prepared by mixing 3.0 g of a commercially available metal-organic-decomposition application material [Kojundo Chemical Lab. Co., Ltd., SYM-AL04, concentration: 2.3% by mass], from which aluminum oxide ($Al_2O_3$) is obtained upon thermal treatment (sintering) and 3.0 g of a commercially available metal-organic-decomposition application material [Kojundo Chemical Lab. Co., Ltd., Nb-05, concentration: 5% by mass], from which niobium oxide ($Nb_2O_5$) is produced upon thermal treatment (sintering).

Passivation material (a-1) was applied by spin-coating on one side of a p-type silicon substrate (from 8 Ω·cm to 12 Ω·cm) having a size of 8 inches and 725 μm in thickness, from which a spontaneously oxidized film had been previously removed with hydrofluoric acid at 0.049% by mass concentration, and the silicon substrate was pre-baked on a hot plate at 120° C. for 3 minutes. Subsequently, thermal treatment (sintering) was performed under a nitrogen atmosphere at 650° C. for an hour, thereby obtaining a passivation film including aluminum oxide and niobium oxide [niobium oxide/aluminum oxide=68/32 (mass ratio)]. The film thickness as measured with an ellipsometer was 43 nm. As a result of FT-IR measurement of the passivation film, a slight peak derived from an alkyl group was observed at approximately 1,200 $cm^{-1}$.

Subsequently, a capacitor having a MIS (metal-insulator-semiconductor) structure was prepared by forming plural aluminum electrodes having a diameter of 1 mm on the passivation film by vapor deposition though a metal mask. The voltage dependency of electrostatic capacitance (C-V property) of the capacitor was measured with a commercially available prober and a commercially available LCR meter (Hewlett-Packard Company, 4275A). As a result, it was found that the flat band voltage (Vfb) shifted from the ideal value of −0.81 V to +0.32 V. From this amount of shift, it was found that the passivation film obtained from passivation material (a-1) exhibited a negative fixed charge at a fixed charge density (Nf) of $-7.4 \times 10^{11}$ $cm^{-2}$.

In the same manner as the above, passivation material (a-1) was applied onto both sides of an 8-inch p-type silicon substrate. Then, the silicon substrate was pre-baked and subjected to thermal treatment (sintering) under a nitrogen atmosphere at 650° C. for an hour, thereby preparing a sample of a silicon substrate having both sides covered with a passivation film. The carrier lifetime of this sample was measured with a lifetime measurement device (Kobelco Research Institute Inc., RTA-540). As a result, the carrier lifetime was 530 μs. For comparison, the carrier lifetime of the same 8-inch p-type silicon substrate, which was passivated by an iodine passivation method, was measured. The result was 1,100 μs.

From the above description, it was found that a passivation film obtained by thermal treatment (sintering) of the passivation material (a-1) exhibited a certain degree of passivation performance, and had a negative fixed charge.

Reference Example 1-2

In the same manner as Reference Example 1-1, a commercially available metal-organic decomposition application material [Kojundo Chemical Lab. Co., Ltd., SYM-AL04, concentration: 2.3% by mass] from which aluminum oxide ($Al_2O_3$) is obtained upon thermal treatment (sintering) and a commercially available metal-organic decomposition application material [Kojundo Chemical Lab. Co., Ltd., Nb-05, concentration: 5% by mass] from which niobium oxide ($Nb_2O_5$) is obtained upon thermal treatment (sintering) were mixed at different ratios, and passivation materials (a-2) to (a-7) shown in Table 3 were prepared.

In the same manner as Reference Example 1-1, a passivation film was prepared by applying each of passivation materials (a-2) to (a-7) onto one side of a p-type silicon substrate, and performing thermal treatment (sintering). The voltage dependency of the electrostatic capacitance of the resulting passivation film was measured, and the fixed charge density was calculated therefrom.

Further, in the same manner as Reference Example 1-1, a sample was prepared by applying a passivation material onto both sides of a p-type silicon substrate, and performing thermal treatment (sintering). The sample was used for the measurement of carrier lifetime. The results are summarized in Table 3.

Since passivation material (a-2) to (a-7) exhibited a certain degree of carrier lifetime after thermal treatment (sintering), although the results were different depending on the ratios of niobium oxide/aluminum oxide (mass ratio) after thermal treatment (sintering), it was suggested that these passivation materials were capable of functioning as passivation films. It was found that all of the passivation films obtained from passivation materials (a-2) to (a-7) exhibited a negative fixed charge in a stable manner, and that the passivation films were suitable for the purpose of passivating a p-type silicon substrate.

TABLE 3

| Material | Niobium Oxide/Aluminum Oxide After Thermal treatment (Mass Ratio) | Film Thickness After Thermal treatment (nm) | Fixed Charge Density ($cm^{-2}$) | Carrier Lifetime (μs) |
|---|---|---|---|---|
| a-2 | 30/70 | 35 | $-1.1 \times 10^{10}$ | 610 |
| a-3 | 40/60 | 42 | $-2.1 \times 10^{10}$ | 540 |
| a-4 | 40/50 | 41 | $-7.1 \times 10^{10}$ | 530 |
| a-5 | 60/40 | 42 | $-4.1 \times 10^{11}$ | 400 |
| a-6 | 80/20 | 53 | $-8.3 \times 10^{11}$ | 280 |
| a-7 | 90/10 | 55 | $-9.5 \times 10^{11}$ | 100 |

Reference Example 1-3

3.18 g (0.010 mol) of a commercially available niobium (V) ethoxide (structural formula: $Nb(OC_2H_5)_5$, molecular weight: 318.21) and 1.02 g (0.005 mol) of a commercially available aluminum triisopropoxide (structural formula: $Al(OCH(CH_3)_2)_3$, molecular weight: 204.25) were dissolved in 80 g of cyclohexane, and passivation material (c-1) at a concentration of 5% by mass was prepared.

Passivation material (c-1) was applied by spin coating on one side of a p-type silicon substrate (from 8 Ω·cm to 12 Ω·cm) having a size of 8 inches and 725 μm in thickness, from which a spontaneously oxidized film had been previously removed with hydrofluoric acid at 0.049% by mass concentration, and the silicon substrate was pre-baked on a hot plate at 120° C. for 3 minutes. Subsequently, thermal treatment (sintering) was performed under a nitrogen atmosphere at 600° C. for an hour, thereby obtaining a passivation film including aluminum oxide and niobium oxide. The film thickness as measured with an ellipsometer was 50 nm. As a result of elemental analysis, the ratio Nb/Al/C was 81/14/5 (% by mass). As a result of FT-IR measurement of the passivation film, a slight peak derived from an alkyl group was observed at approximately 1,200 $cm^{-1}$.

Subsequently, a capacitor having a MIS (metal-insulator-semiconductor) structure was prepared by forming plural aluminum electrodes having a diameter of 1 mm on the passivation film by vapor deposition through a metal mask. The voltage dependency of electrostatic capacitance (C-V property) of the capacitor was measured with a commercially available prober and a commercially available LCR meter (Hewlett-Packard Company, 4275A). As a result, it was found that the flat band voltage (Vfb) shifted from the ideal value of −0.81 to +4.7 V. From this amount of shift, it was found that the passivation film obtained from passivation material (c-1) exhibited a negative fixed charge at a fixed charge density (Nf) of $-3.2 \times 10^{12}$ $cm^{-2}$.

In the same manner as the above, passivation material (c-1) was applied onto both sides of an 8-inch p-type silicon substrate, and the silicon substrate was pre-baked and subjected to thermal treatment (sintering) under a nitrogen atmosphere at 600° C. for an hour, and a sample of a silicon substrate having both sides covered with a passivation film was prepared. The carrier lifetime of the sample was measured with a lifetime measurement device (Kobelco Research Institute Inc., RTA-540). As a result, the carrier lifetime was 330 μs. For comparison, the carrier lifetime of the same 8-inch p-type silicon substrate that had been passivation by an iodine passivation method was measured. The result was 1,100 μs.

In view of the above, it was found that a passivation film obtained by performing thermal treatment (sintering) to passivation material (c-1) exhibited a certain degree of passivation performance and a negative fixed charge.

Reference Example 1-4

Passivation material (c-2) was prepared by dissolving 2.35 g (0.0075 mol) of a commercially available niobium (V) ethoxide (structural formula: $Nb(OC_2H_5)_5$, molecular weight: 318.21), 1.02 g (0.005 mol) of a commercially available aluminum triisopropoxide (structural formula: $Al(OCH(CH_3)_2)_3$, molecular weight: 204.25) and 10 g of a novolac resin in 10 g of diethyleneglycol monobutyl ether acetate and 10 g of cyclohexane.

Passivation material (c-2) was applied by spin coating onto one side of a p-type silicon substrate (from 8 Ω·cm to 12 Ω·cm) having a size of 8 inches and 725 μm in thickness, from which a spontaneously oxidized film had been previously removed with hydrofluoric acid at 0.049% by mass concentration. The silicon substrate was pre-baked on a hot plate at 120° C. for 3 minutes. Subsequently, thermal treatment (sintering) was performed under a nitrogen atmosphere at 600° C. for an hour, and a passivation film including aluminum oxide and niobium oxide was prepared. The film thickness as measured with an ellipsometer was 14 nm. As a result of elemental analysis, the ratio Nb/Al/C was 75/17/8 (% by mass). As a result of FT-IR measurement of a passivation film, a slight peak derived from an alkyl group was observed at approximately 1,200 $cm^{-1}$.

Subsequently, a capacitor having a MIS (metal-insulator-semiconductor) structure was prepared by forming plural aluminum electrodes having a diameter of 1 mm on the passivation film by vapor deposition through a metal mask. The voltage dependency of electrostatic capacitance (C-V property) of the capacitor was measured with a commercially available prober and a commercially available LCR meter (Hewlett-Packard Company, 4275A). As a result, it was found that the flat band voltage (Vfb) shifted from the ideal value of −0.81 V to +0.10V. From this amount of shift, it was found that the passivation film obtained from passivation material (c-2) exhibited a negative fixed charge at a fixed charge density (Nf) of $-0.8 \times 10^{11}$ cm$^{-2}$.

In the same manner as the above, passivation material (c-2) was applied on both sides of an 8-inch p-type silicon substrate. The silicon substrate was pre-baked and subjected to thermal treatment (sintering) under a nitrogen atmosphere at 600° C. for an hour, and a sample of a silicon substrate having both sides covered with a passivation film was prepared. The carrier lifetime of the sample was measured with a lifetime measurement device (Kobelco Research Institute, Inc., RTA-540). As a result, the carrier lifetime was 200 μs. For comparison, the carrier lifetime of the same 8-inch p-type silicon substrate, which was passivated by an iodine passivation method, was measured. The result was 1,100 μs.

In view of the above, it was found that a passivation film obtained by performing thermal treatment (sintering) of passivation material (c-2) exhibited a certain degree of passivation performance and a negative fixed charge.

Reference Example 1-5 and Reference Comparative Example 1-1

In the same manner as Reference Example 1-1, a commercially available metal-organic decomposition application material [Kojundo Chemical Lab. Co., Ltd., SYM-AL04, concentration: 2.3% by mass] from which aluminum oxide ($Al_2O_3$) is obtained upon thermal treatment (sintering), a commercially available metal-organic decomposition application material [Kojundo Chemical Lab. Co., Ltd., Nb-05, concentration: 5% by mass] from which niobium oxide ($Nb_2O_5$) is obtained upon thermal treatment (sintering) were mixed at different ratios, and passivation materials (b-1) to (b-7) shown in Table 4 were prepared.

In the same manner as Reference Example 1-1, a passivation film was prepared by applying each of passivation materials (b-1) to (b-7) on one side of a p-type silicon substrate and performing thermal treatment (sintering). By using the passivation film, voltage dependency of the electrostatic capacitance was measured and a fixed charge density was calculated therefrom.

In the same manner as Reference Example 1-1, a sample obtained by applying a passivation material (an application material) on both sides of a p-type silicon substrate and curing the same was used for the measurement of a carrier lifetime. The results are shown in Table 4.

TABLE 4

| Material | Niobium Oxide/Aluminum Oxide after Thermal treatment (Weight Ratio) | Film Thickness after Thermal treatment (nm) | Fixed Charge Density (cm$^{-2}$) | Carrier Lifetime (μs) |
|---|---|---|---|---|
| b-1 | 10/90 | 35 | $2.3 \times 10^{11}$ | 600 |
| b-2 | 20/80 | 36 | $2.2 \times 10^{11}$ | 540 |
| b-3 | 10/90 | 40 | $1.1 \times 10^{10}$ | 480 |
| b-4 | 10/90 | 42 | $-1.2 \times 10^{10}$ | 520 |
| b-5 | 20/80 | 45 | $-1.0 \times 10^{10}$ | 440 |
| b-6 | 20/80 | 38 | $1.3 \times 10^{10}$ | 470 |
| b-7 | 0/100 | 34 | $2.2 \times 10^{11}$ | 600 |

It was found that all of the passivation films obtained from passivation materials (b-1) to (b-6) had a long carrier lifetime and were capable of functioning as a passivation film. In the cases in which niobium oxide/aluminum oxide was 10/90 and 20/80, there was a significant variability among the values of the fixed charge density and a negative fixed charge density was not obtained in a stable manner. However, it was confirmed that a negative fixed charge density could be achieved by using aluminum oxide and niobium oxide. When the measurement was performed by a CV method using a passivation material in which niobium oxide/aluminum oxide was 10/90 and 20/80, the resulting passivation film exhibited a positive fixed charge in some cases, and did not exhibit a negative fixed charge in a stable manner. A passivation film that exhibits a positive fixed charge can be used for passivation of an n-type silicon substrate.

On the other hand, a negative fixed charge density could not be obtained from passivation material (b-7) composed of 100% by mass of aluminum oxide.

Reference Comparative Example 1-2

As passivation material (d-1), a commercially available metal-organic decomposition application material [Kojundo Chemical Lab. Co., Ltd., Ti-03-P, concentration: 3% by mass] from which titanium oxide ($TiO_2$) is obtained upon thermal treatment (sintering); as a passivation material (d-2), a commercially available metal-organic decomposition application material [Kojundo Chemical Lab. Co., Ltd., BT-06, concentration: 6% by mass] from which barium titanate ($BaTiO_3$) is obtained upon thermal treatment (sintering); and as passivation material (d-3), a commercially available metal-organic decomposition application material [Kojundo Chemical Lab. Co., Ltd., Hf-05, concentration: 5% by mass] from which hafnium oxide ($HfO_2$) is obtained upon thermal treatment (sintering), were prepared.

In the same manner as Reference Example 1-1, each of passivation materials (d-1) to (d-3) was applied on one side of a p-type silicon substrate, and the silicon substrate was subjected to thermal treatment (sintering) to prepare a passivation film. The passivation film was used for the measurement of voltage dependency of electrostatic capacitance, and a fixed charge density was calculated therefrom.

Moreover, in the same manner as Reference Example 1-1, a passivation material was applied on both sides of a p-type silicon substrate, and the carrier lifetime was measured using a sample obtained by performing thermal treatment (sintering). The results are shown in Table 5.

TABLE 5

| Material | Metal Oxide | Film Thickness after Thermal treatment (nm) | Fixed Charge Density (cm$^{-2}$) | Carrier Lifetime (μs) |
|---|---|---|---|---|
| d-1 | $TiO_2$ | 53 | $5.0 \times 10^9$ | 4 |
| d-2 | $BaTiO_3$ | 51 | $4.2 \times 10^9$ | 5 |
| d-3 | $HfO_2$ | 60 | $-4.0 \times 10^8$ | 54 |

All of the passivation film obtained from passivation materials (d-1) to (d-3) exhibited a small carrier lifetime, and exhibited an insufficient passivation performance. In addition, these passivation films exhibited a positive fixed charge. A passivation film obtained from passivation material (d-3) exhibited a negative fixed charge, but the value was small. In addition, the carrier lifetime was relatively small, which proved an insufficient function as a passivation film.

Reference Example 1-6

A photovoltaic cell element of a structure shown in FIG. 14 was prepared using a monocrystalline silicon substrate doped with boron as silicon substrate 101. After performing texture processing to a surface of silicon substrate 101, the application-type phosphorus diffusion material was applied onto a light receiving surface, and diffusion layer 102 (a phosphorus diffusion layer) was formed by performing thermal treatment. Subsequently, the application-type phosphorus diffusion material was removed with dilute hydrofluoric acid.

Subsequently, a SiN film was formed by plasma CVD as light receiving surface anti-reflection film 103 on a light receiving surface. Then, passivation material (a-1) as prepared in Reference Example 1-1 was applied onto a region excluding a contact region (opening OA) at a back surface of silicon substrate 101 by an ink-jet method. Subsequently, passivation film 107 having opening OA was formed by performing thermal treatment.

As a sample, passivation film 107 was prepared, by using passivation material (c-1) prepared in Reference Example 1-3.

Subsequently, on light receiving surface anti-reflection film 103 (SiN film) formed on silicon substrate 101, a paste mainly composed of silver was applied by screen printing in the shape of predetermined finger electrodes and bus bar electrodes. On the back surface, a paste mainly composed of aluminum was applied onto an entire surface by screen printing. Subsequently, thermal treatment (fire through) was performed at 850° C. to form an electrode (first electrode 105 and second electrode 106), and BSF layer 104 was formed by allowing aluminum to diffuse in a portion of opening OA at the back surface. A photovoltaic cell element having a structure shown in FIG. 14 was thus prepared.

In the aforementioned method, the silver electrode at the light receiving surface was formed by a fire through process without forming an opening in the SiN film. However, it is also possible to form a silver electrode by forming opening OA to the SiN film, and then forming the silver electrode.

For comparison, an aluminum paste was applied onto an entire back surface according to the above preparation process, except that passivation film 107 was not formed. Then, $p^+$ layer 114 corresponding to BSF layer 104 and electrode 116 corresponding to second electrode were formed on the entire surface, thereby forming a photovoltaic cell element having a structure shown in FIG. 11. With these photovoltaic cell elements, characterization (short-circuit current, open-voltage, fill factor, and conversion efficiency) was performed. The characterization was performed according to JIS-C-8913 (2005) and JIS-C-8914 (2005). The results are shown in Table 6.

From the results shown in Table 6, it was found that a photovoltaic cell element having passivation film 107 including niobium oxide and aluminum oxide exhibited an increased short-circuit current and an increased open voltage, as compared to a photovoltaic cell element not having passivation film 107, and that the conversion efficiency (incident photon-to-current conversion efficiency) was increased by up to 1%.

TABLE 6

| Back Surface Passivation Film | Short-Circuit Current (mA/cm$^2$) | Open Voltage (V) | Fill Factor | Conversion Efficiency (%) |
|---|---|---|---|---|
| a-1 | 33.5 | 0.635 | 0.804 | 17.0 |
| c-1 | 33.4 | 0.625 | 0.803 | 16.7 |
| None | 32.8 | 0.61 | 0.80 | 16.0 |

Reference Embodiment 2

The following are a passivation film, an application material, a photovoltaic cell element and a silicon substrate having a passivation film, according to Reference Embodiment 2.

<1> A passivation film comprising an oxide of at least one vanadium-group element (vanadium-group element oxide) selected from the group consisting of aluminum oxide, vanadium oxide and tantalum oxide, the passivation film being used for a photovoltaic cell element having a silicon substrate.

<2> The passivation film according to <1>, wherein a mass ratio of the vanadium-group element oxide to the aluminum oxide (vanadium group element oxide/aluminum oxide) is from 30/70 to 90/10.

<3> The passivation film according to <1> or <2>, wherein a total content of the vanadium-group element oxide and the aluminum oxide is 90% or more.

<4> The passivation film according to any one of from <1> to <3>, comprising two or three vanadium-group element oxides selected from the group consisting of vanadium oxide, niobium oxide and tantalum oxide, as the oxide of vanadium-group element.

<5> The passivation film according to any one of from <1> to <4>, which is a thermally-treated product of an application material that comprises a precursor of at least one vanadium-group element oxide selected from the group consisting of an aluminum oxide precursor, a vanadium oxide precursor and a tantalum oxide precursor.

<6> An application material, comprising a precursor of at least one vanadium-group element oxide selected from the group consisting of an aluminum oxide precursor, a vanadium oxide precursor, and a tantalum oxide precursor, the application material being used for formation of a passivation film of a photovoltaic cell element having a silicon substrate.

<7> A photovoltaic cell element, comprising:
a p-type silicon substrate;
an n-type impurity diffusion layer formed at a first surface that is a light receiving surface of the silicon substrate;
a first electrode formed on the impurity diffusion layer;
a passivation film that has an opening and is formed on a second surface of the silicon substrate that is opposite to the light receiving surface; and
a second electrode that is formed on the second surface of the silicon substrate and is electrically connected through the opening of the passivation film to the second surface of the silicon substrate,
the passivation film being at least one vanadium-group element oxide selected from the group consisting of aluminum oxide, vanadium oxide and tantalum oxide.

<8> The photovoltaic cell element according to <7>, comprising a p-type impurity diffusion layer that is formed on a partial or an entire surface of the second surface of the silicon substrate, and is added with an impurity at a concentration higher than the concentration of the silicon substrate,
the second electrode being electrically connected through an opening of the passivation film to the p-type impurity diffusion layer.

<9> A photovoltaic cell element, comprising:
an n-type silicon substrate;
a p-type impurity diffusion layer that is formed on a first surface that is a light receiving surface of the silicon substrate;

a first electrode that is formed on the impurity diffusion layer;

a passivation film that has an opening and is formed on a second surface of the silicon substrate that is opposite to the light receiving surface; and a second electrode that is formed on a second surface of the silicon substrate and is electrically connected through the opening of the passivation film to the second surface of the silicon substrate, the passivation film comprising at least one vanadium-group element oxide selected from the group consisting of aluminum oxide, vanadium oxide and tantalum oxide.

<10> The photovoltaic cell according to <9>, comprising an n-type impurity diffusion layer that is formed on a partial or an entire surface of a second surface of the silicon substrate, and is added with an impurity at a concentration higher than the concentration of the silicon substrate, the second electrode being electrically connected through the opening of the passivation film to the n-type impurity diffusion layer.

<11> The photovoltaic cell element according to any one of from <7> to <10>, wherein a mass ratio of the vanadium-group element oxide and the aluminum oxide in the passivation film is from 30/70 to 90/10.

<12> The photovoltaic cell element according to any one of from <7> to <11>, wherein a total content of the vanadium-type element oxide and the aluminum oxide in the passivation film is 90% or more.

<13> The photovoltaic cell element according to any one of from <7> to <12>, comprising two or three vanadium-group element oxides selected from the group consisting of vanadium oxide, niobium oxide, and tantalum oxide as the vanadium-group element oxide.

<14> The silicon substrate having a passivation film, comprising:

a silicon substrate; and the passivation film for a photovoltaic cell element according to any one of from <1> to <5> which is provided on an entire or partial surface of the silicon substrate.

According to the Reference Embodiments as described above, a passivation film that can extend a carrier lifetime of a silicon substrate and has a negative fixed charge can be attained at low cost. In addition, an application material that attains formation the passivation film can be provided. In addition, a photovoltaic cell element that utilizes the passivation film and exhibits a high efficiency at low cost can be provided. Moreover, a silicon substrate having a passivation film that extends a carrier lifetime of a silicon substrate and has a negative fixed charge can be attained at low cost.

The passivation film of the present embodiment is a passivation film used for a silicon photovoltaic cell element, and includes at least one vanadium-group element oxide selected from the group consisting of aluminum oxide, vanadium oxide, and tantalum oxide.

In addition, in the present embodiment, the amount of a fixed charge of the passivation film can be controlled by changing the composition of the passivation film. A vanadium-group element herein refers to an element that belongs to group 5 in the periodic table, which is selected from vanadium, niobium and tantalum.

From the viewpoint of being able to stabilizing a negative fixed charge, the mass ratio of a vanadium-group element oxide to an aluminum oxide is more preferably from 35/65 to 90/10, further preferably from 50/50 to 90/10.

The mass ratio of a vanadium-group element oxide to an aluminum oxide in the passivation film can be measured by energy dispersive X-ray spectrometry (EDX), secondary ion mass spectrometry (SIMS) and induced coupled plasma-mass spectrometry (ICP-MS). Specific conditions for the measurement are as follows. A passivation film is dissolved in an acid or an alkaline aqueous solution, and the resulting solution is atomized and introduced in an Ar plasma. The light released when an excited element returns to the ground state is dispersed, and its wavelength and intensity are measured. The resulting wavelength is used for a qualitative analysis of an element, and the resulting intensity is used for quantitative analysis.

The total content of a vanadium-group element oxide and an aluminum oxide in a passivation film is preferably 80% by mass or more, and more preferably 90% by mass or more from the viewpoint of being able to maintaining a favorable property. The more the components other than a vanadium-group element oxide and an aluminum oxide in the passivation film are, the greater the effect of a negative fixed charge is.

From the viewpoint of improving the film quality and adjusting the elastic modulus, a component other than a vanadium-group element oxide and an aluminum oxide may be included in the passivation film as an organic component. The existence of an organic component in the passivation film can be confirmed by elemental analysis and FT-IR measurement of the film.

From the viewpoint of obtaining a greater negative fixed charge, vanadium oxide ($V_2O_5$) is preferably selected as the vanadium-group element oxide.

The passivation film may include, as a vanadium-group element oxide, two or three kinds of vanadium-group element oxides selected from the group consisting of vanadium oxide, niobium oxide and tantalum oxide.

The passivation film is preferably obtained by performing thermal treatment of an application material, more preferably obtained by forming a film from an application material by a coating method or a printing method, and performing thermal treatment to remove an organic component from the film. That is, the passivation film may be obtained as a thermally-treated product of an application material that includes an aluminum oxide precursor and a vanadium-group element oxide precursor. Details of the application material will be described below.

The application material of the present embodiment is an application material used for a passivation film for a photovoltaic cell element having a silicon substrate, and includes a precursor of an aluminum oxide precursor and at least one vanadium-group element oxide precursor selected from a vanadium oxide precursor and a tantalum oxide precursor. As a vanadium-group element oxide precursor included in the application material, a vanadium oxide ($V_2O_5$) precursor is preferably selected from the viewpoint of a negative fixed charge of a passivation film formed from the applicable material. The application material may include, as a vanadium-group element oxide precursor, two or three kinds of vanadium-group element oxide precursor selected from the group consisting of a vanadium oxide precursor, a niobium oxide precursor and a tantalum oxide precursor.

The aluminum oxide precursor is not particularly limited so long as it can produce aluminum oxide. From the viewpoint of dispersing aluminum oxide to a silicon substrate in a uniform manner, and chemical stability, the aluminum oxide precursor is preferably an organic aluminum oxide precursor. Examples of an organic aluminum oxide precursor include aluminum triisopropoxide (structural formula: Al(OCH(CH$_3$)$_2$)$_3$, Kojundo Chemical Lab. Co., Ltd., SYM-AL04.

The vanadium-group element oxide precursor is not particularly limited so long as it can produce a vanadium-group element oxide. From the view point of dispersing aluminum oxide to a silicon substrate in a uniform manner, and chemical stability, the vanadium-group element oxide precursor is preferably an organic vanadium-group element oxide precursor.

Examples of an organic vanadium oxide precursor include vanadium (V) oxytriethoxide (structural formula: VO(OC$_2$H$_5$)$_3$, molecular weight: 202.13), Kojundo Chemical Lab. Co., Ltd., V-02. Examples of an organic tantalum oxide precursor include tantalum (V) methoxide (structural formula: Ta(OCH$_3$)$_5$, molecular weight: 336.12), Kojundo Chemical Lab. Co., Ltd., Ta-10-P. Example of an organic niobium oxide precursor include niobium (V) ethoxide (structural formula: Nb(OC$_2$H$_5$)$_5$, molecular weight: 318.21), Kojundo Chemical Lab. Co., Ltd., Nb-05.

A passivation film can be obtained by forming a film from the application material that includes an organic vanadium-group element oxide precursor and an organic aluminum oxide precursor by a coating method or a printing method, and then performing thermal treatment to remove an organic component from the film. Accordingly, the passivation film may include an organic component. The content of an organic component in the passivation film is more preferably less than 10% by mass, still more preferably 5% by mass or less, especially preferably 1% by mass or less.

The photovoltaic cell element (photoelectric conversion device) of the present embodiment includes a passivation film (an insulating film, a protective insulating film) as described in the above embodiment, i.e., a film including aluminum oxide and at least one vanadium-group element oxide selected from vanadium oxide and tantalum oxide, near a photoelectric interface of a silicon substrate. By including aluminum oxide and at least one vanadium-group element oxide selected from the group consisting of vanadium oxide and tantalum oxide, it is possible to extend a carrier lifetime of a silicon substrate and exhibit a negative fixed charge, thereby improving the properties of a photovoltaic cell element (incident photon-to-current conversion efficiency).

For the description of the structure and the production method of the photovoltaic cell element according to the present embodiment, the description of the structure of and the production method of the photovoltaic cell element according to Reference Embodiment 1 may be referred to.

The present embodiments will be hereinafter described in detail by referring to the Reference Examples and the Comparative Examples.

<Vanadium Oxide Used as Vanadium-Group Element Oxide>

Reference Example 2-1

Passivation material (a2-1) as an application material was prepared by mixing 3.0 g of a commercially available organic metal film application material [Kojundo Chemical Lab. Co., Ltd., SYM-AL04, concentration: 2.3% by mass] from which aluminum oxide (Al$_2$O$_3$) is obtained upon thermal treatment (sintering), and 6.0 g of a commercially available organic metal film application material [Kojundo Chemical Lab. Co., Ltd., V-02, concentration: 2% by mass] from which vanadium oxide (V$_2$O$_5$) is obtained upon thermal treatment (sintering).

Passivation material (a2-1) was applied by spin coating on one side of a p-type silicon substrate (from 8 Ω·cm to 12 Ω·cm) having a size of 8 inches and 725 μm in thickness, from which a spontaneously oxidized film had been previously removed with hydrofluoric acid at 0.49% by mass concentration. The silicon substrate was pre-baked on a hot plate at 120° C. for 3 minutes. Subsequently, thermal treatment (sintering) was performed under a nitrogen atmosphere at 700° C. for 30 minutes, thereby obtaining a passivation film including aluminum oxide and vanadium oxide [vanadium oxide/aluminum oxide=63/37 (% by mass)]. The film thickness as measured with an ellipsometer was 51 nm. As a result of FT-IR measurement of the passivation film, a slight peak derived from an alkyl group was observed at approximately 1,200 cm$^{-1}$.

Subsequently, a capacitor having a MIS (metal-insulator-semiconductor) structure was prepared by forming plural aluminum electrodes having a diameter of 1 mm on the passivation film by vapor deposition through a metal mask. The voltage dependency of electrostatic capacitance (C-V property) of the capacitor was measured with a commercially available prober and a commercially available LCR meter (Hewlett-Packard Company, 4275A). As a result, it was found that the flat band voltage (Vfb) shifted from the ideal value of −0.81 V to +0.02 V. From this amount of shift, it was found that the passivation film obtained from passivation material (a2-1) exhibited a negative fixed charge at a fixed charge density (Nf) of −5.2×10$^{11}$ cm$^{-2}$.

In a similar manner to the above, passivation material (a2-1) was applied on both sides of an 8-inch p-type silicon substrate, and the silicon substrate was pre-baked and subjected to thermal treatment (sintering) under a nitrogen atmosphere at 650° C. for an hour, thereby preparing a sample of a silicon substrate having both sides covered with a passivation film. The carrier lifetime of the sample was measured with a lifetime measurement device (Kobelco Research Institute Inc., RTA-540). As a result, the carrier lifetime was 400 μs. For comparison, the carrier lifetime of the same 8-inch p-type silicon substrate, which was passivated by an iodine passivation method, was measured. The result was 1,100 μs. Further, the carrier lifetime was measured again after 14 days from the preparation of the sample. The result was 380 μs. From these results, it was found that a decrease in the carrier lifetime (from 400 μs to 380 μs) was less than −10%, indicating that a decrease in carrier lifetime was small.

In view of the above, it was found that a passivation film obtained by performing thermal treatment (sintering) of passivation material (a2-1) exhibited a certain degree of passivation performance and a negative fixed charge.

Reference Example 2-2

In the same manner as Reference Example 2-1, a commercially available organic metal film application material [Kojundo Chemical Lab. Co., Ltd., SYM-AL04, concentration: 2.3% by mass] from which aluminum oxide (Al$_2$O$_3$) is obtained upon thermal treatment (sintering), and a commercially available organic metal film application material [Kojundo Chemical Lab., Co., Ltd., V-02, concentration: 2% by mass] from which vanadium oxide (V$_2$O$_5$) is obtained upon thermal treatment were mixed at different ratios, and passivation materials (a2-2) to (a2-7) as shown in Table 7 were prepared.

In the same manner as Reference Example 2-1, a passivation film was prepared by applying each of passivation materials (a2-2) to (a2-7) onto one side of a p-type silicon substrate, and subjecting the same to thermal treatment (sintering). The voltage dependency of the electrostatic capacitance of the resulting passivation film was measured, and the fixed charge density was calculated therefrom.

In addition, in the same manner as Reference Example 2-1, a sample was prepared by applying a passivation material onto both sides of a p-type silicon substrate and performing thermal treatment (sintering), and the carrier lifetime of the sample was measured.

The obtained results are shown in Table 7. Further, the carrier lifetime was measured again after 14 days from the preparation of the sample. As a result, it was found that a decrease in the carrier lifetime of all of the passivation films obtained from passivation materials (a2-2) to (a2-7) as shown in Table 7 was less than −10%, indicating that the decrease in the carrier lifetime was small.

From the results that all of passivation materials (a2-2) to (a2-7) showed a negative fixed charge and a certain degree of carrier lifetime after the thermal treatment (sintering), it is suggested that the samples can function as a passivation film, although the results are different depending on the ratio of vanadium oxide/aluminum oxide (mass ratio) after the thermal treatment (sintering). All of the passivation films obtained from passivation materials (a2-2) to (a2-7) exhibited a negative fixed charge in a stable manner, and found to be suitably utilized for passivation of a p-type silicon substrate.

TABLE 7

| | Vanadium Oxide/Aluminum Oxide after Thermal treatment (Mass Ratio) | Film Thickness after Thermal treatment (nm) | Fixed Charge Density ($cm^{-2}$) | Carrier Lifetime ($\mu s$) |
|---|---|---|---|---|
| a2-2 | 30/70 | 71 | $-1.0 \times 10^{10}$ | 600 |
| a2-3 | 40/60 | 69 | $-1.7 \times 10^{10}$ | 540 |
| a2-4 | 50/50 | 73 | $-6.3 \times 10^{10}$ | 530 |
| a2-5 | 60/40 | 77 | $-4.9 \times 10^{11}$ | 420 |
| a2-6 | 80/20 | 75 | $-7.2 \times 10^{11}$ | 220 |
| a2-7 | 90/10 | 75 | $-8.3 \times 10^{11}$ | 130 |

Reference Example 2-3

As a compound from which vanadium oxide ($V_2O_5$) is obtained upon thermal treatment (sintering), 1.02 g (0.010 mol) of a commercially available vanadium (V) oxytriethoxide (structural formula: $VO(OC_2H_5)_3$, molecular weight: 202.13) and, as a compound from which aluminum oxide ($Al_2O_3$) is obtained upon thermal treatment (sintering), 2.04 g (0.010 mol) of a commercially available aluminum triisopropoxide (structural formula: $Al(OCH(CH_3)_2)_3$, molecular weight: 204.25) were dissolved in 60 g of cyclohexane, thereby preparing passivation material (b2-1) at a concentration of 5% by mass.

Passivation material (b2-1) was applied by spin coating on one side of a p-type silicon substrate (from 8 Ω·cm to 12 Ω·cm) having a size of 8 inches and 725 μm in thickness, from which a spontaneously oxidized film had been previously removed with hydrofluoric acid at 0.49% by mass concentration. The silicon substrate was pre-baked on a hot plate at 120° C. for 3 minutes. Subsequently, the silicon substrate was subjected to thermal treatment under a nitrogen atmosphere at 650° C. for an hour, thereby obtaining a passivation film including aluminum oxide and vanadium oxide. The film thickness as measured with an ellipsometer was 60 nm. As a result of elemental analysis, the ratio V/Al/C was 64/33/3 (% by mass). As a result of FT-IR measurement of a passivation film, a slight peak derived from an alkyl group was observed at approximately 1,200 $cm^{-1}$.

Subsequently, a capacitor having a MIS (metal-insulator-semiconductor) structure was prepared by forming plural aluminum electrodes having a diameter of 1 mm on the passivation film by vapor deposition through a metal mask. The voltage dependency of electrostatic capacitance (C-V property) of the capacitor was measured with a commercially available prober and a commercially available LCR meter (Hewlett-Packard Company, 4275A). As a result, it was found that the flat band voltage (Vfb) shifted from the ideal value of −0.81 V to +0.10V. From this amount of shift, it was found that the passivation film obtained from passivation material (b2-1) exhibited a negative fixed charge at a fixed charge density (Nf) of $-6.2 \times 10^{11}$ $cm^{-2}$.

In the same manner as the above, passivation material (b2-1) was applied on both sides of an 8-inch p-type silicon substrate, and the silicon substrate was pre-baked and subjected to thermal treatment (sintering) under a nitrogen atmosphere at 600° C. for an hour, thereby preparing a sample of a silicon substrate having both sides covered with a passivation film. The carrier lifetime of the sample was measured with a lifetime measurement device (Kobelco Research Institute Inc., RTA-540). As a result, the carrier lifetime was 400 μs. For comparison, the carrier lifetime of the same 8-inch p-type silicon substrate, which was passivated by an iodine passivation method, was measured. The result was 1,100 μs.

In view of the above, it was found that a passivation film obtained by performing thermal treatment (sintering) of passivation material (b2-1) exhibited a certain degree of passivation performance and a negative fixed charge.

Reference Example 2-4

Passivation material (b2-2) was prepared by dissolving 1.52 g (0.0075 mol) of a commercially available vanadium (V) oxytriethoxide (structural formula: $VO(OC_2H_5)_3$, molecular weight: 202.13), 1.02 g (0.005 mol) of a commercially available aluminum triisopropoxide structural formula: $Al(OCH(CH_3)_2)_3$, molecular weight: 204.25) and 10 g of a novolac resin were dissolved in 10 g of diethyleneglycol monobutyl ether acetate and 10 g of cyclohexane.

Passivation material (b2-2) was applied by spin coating on one side of a p-type silicon substrate (from 8 Ω·cm to 12 Ω·cm) having a size of 8 inches and 725 μm in thickness, from which a spontaneously oxidized film had been previously removed with hydrofluoric acid at 0.49% by mass concentration. The silicon substrate was pre-baked on a hot plate at 120° C. for 3 minutes. Subsequently, the silicon substrate was subjected to thermal treatment under a nitrogen atmosphere at 650° C. for an hour, thereby obtaining a passivation film including aluminum oxide and vanadium oxide. The film thickness as measured with an ellipsometer was 22 nm. As a result of elemental analysis, the ratio V/Al/C was 71/22/7 (% by mass). As a result of FT-IR measurement of a passivation film, a slight peak derived from an alkyl group was observed at approximately 1,200 $cm^{-1}$.

Subsequently, a capacitor having a MIS (metal-insulator-semiconductor) structure was prepared by forming plural aluminum electrodes having a diameter of 1 mm on the passivation film by vapor depression through a metal mask. The voltage dependency of electrostatic capacitance (C-V property) of the capacitor was measured with a commercially available prober and a commercially available LCR meter (Hewlett-Packard Company, 4275A). As a result, it was found that the flat band voltage (Vfb) shifted from the ideal value of −0.81 V to +0.03 V. From this amount of shift, it was found that the passivation film obtained from passivation material (b2-2) exhibited a negative fixed charge at a fixed charge density (Nf) of $-2.0 \times 10^{11}$ cm$^{-2}$.

In the same manner as the above, passivation material (b2-2) was applied on both sides of an 8-inch p-type silicon substrate. The silicon substrate was pre-baked and subjected to thermal treatment (sintering) under a nitrogen atmosphere at 600° C. for an hour, thereby preparing a sample of a silicon substrate having both sides covered with a passivation film. The carrier lifetime of the sample was measured with a lifetime measurement device (Kobelco Research Institute Inc., RTA-540). As a result, the carrier lifetime was 170 μs. For comparison, the carrier lifetime of the same 8-inch p-type silicon substrate, which was passivated by an iodine passivation method, was measured. The result was 1,100 μs.

In view of the above, it was found that a passivation film obtained by curing passivation material (b2-2) exhibited a certain degree of passivation performance and a negative fixed charge.

<Tantalum Oxide Used as Vanadium-Group Element Oxide>

Reference Example 2-5

A commercially available organic metal film application material [Kojundo Chemical Lab. Co., Ltd., SYM-AL04, concentration: 2.3% by mass] from which aluminum oxide ($Al_2O_3$) is obtained upon thermal treatment (sintering) and a commercially available organic metal film application material [Kojundo Chemical Lab. Co., Ltd., Ta-10-P, concentration: 10% by mass] from which tantalum oxide ($Ta_2O_5$) was obtained upon thermal treatment were mixed at different ratios, and passivation materials (c2-1) to (c2-6) as shown in Table 8 were prepared.

Each of passivation materials (c2-1) to (c2-6) was applied by spin coating on one side of a p-type silicon substrate (from 8 Ω·cm to 12 Ω·cm) having a size of 8 sizes and 725 μm in thickness, from which a spontaneously oxidized film had been previously removed with hydrofluoric acid at 0.49% by mass concentration. The silicon substrate was pre-baked on a hot plate at 120° C. for 3 minutes. Subsequently, thermal treatment (sintering) was performed under a nitrogen atmosphere at 700° C. for 30 minutes, thereby obtaining a passivation film including aluminum oxide and tantalum oxide. This passivation film was used to measure the voltage dependency of electrostatic capacitance, and the fixed charge density was calculated therefrom.

Subsequently, each of passivation materials (c2-1) to (c2-6) was applied on both sides of an 8-inch p-type silicon substrate, and the silicon substrate was subjected to pre-baking and thermal treatment (sintering) under a nitrogen atmosphere at 650° C. for an hour, and a sample of a silicon substrate having both sides covered with a passivation film was prepared. The carrier lifetime of the sample was measured with a lifetime measurement device (Kobelco Research Institute Inc., RTA-540).

The results are shown in Table 8. Further, the carrier lifetime was measured again 14 days after the preparation of the sample. As a result, a decrease in carrier lifetime was less than −10% in all of the passivation films obtained from passivation materials (c2-1) to (c2-6) as shown in Table 8, indicating that a decrease in carrier lifetime is small.

Since all of passivation materials (c2-1) to (c2-6) exhibited a negative fixed charge and a certain level of carrier lifetime after the thermal treatment (sintering), although the results were different depending on the ratio of tantalum oxide/aluminum oxide (mass ratio) after the thermal treatment (sintering), suggesting that they can function as a passivation film.

TABLE 8

| | Tantalum Oxide/Aluminum Oxide after Thermal treatment (Mass Ratio) | Film Thickness after Thermal treatment (nm) | Fixed Charge Density (cm$^{-2}$) | Carrier Lifetime (μs) |
| --- | --- | --- | --- | --- |
| c2-1 | 30/70 | 44 | $-1.1 \times 10^{10}$ | 710 |
| c2-2 | 40/60 | 48 | $-1.3 \times 10^{10}$ | 580 |
| c2-3 | 50/50 | 43 | $-3.2 \times 10^{10}$ | 600 |
| c2-4 | 60/40 | 51 | $-5.8 \times 10^{10}$ | 520 |
| c2-5 | 80/20 | 52 | $-5.5 \times 10^{10}$ | 300 |
| c2-6 | 90/10 | 52 | $-7.3 \times 10^{10}$ | 150 |

Reference Example 2-6

As a compound from which tantalum oxide ($Ta_2O_5$) is obtained upon thermal treatment (sintering), a 1.18 g (0.0025 mol) of a commercially available tantalum (V) methoxide (structural formula: $Ta(OCH_3)_5$, molecular weight: 336.12) and as a compound from which aluminum oxide ($Al_2O_3$) is obtained upon thermal treatment (sintering), 2.04 g (0.010 mol) of a commercially available aluminum triisopropoxide (structural formula: $Al(OCH(CH_3)_2)_3$, molecular weight: 204.25) were dissolved in 60 g of cyclohexane, and passivation material (d2-1) at a concentration of 5% by mass was prepared.

Passivation material (d2-1) was applied by spin coating on one side of a p-type silicon substrate (from 8 Ω·cm to 12 Ω·cm) having a size of 8 inches and 725 μm in thickness, from which a spontaneously oxidized film had been previously removed with hydrofluoric acid at 0.49% by mass concentration. The silicon substrate was pre-baked on a hot plate at 120° C. for 3 minutes. Subsequently, the silicon substrate was subjected to thermal treatment under a nitrogen atmosphere at 700° C. for an hour, thereby obtaining a passivation film including aluminum oxide and tantalum oxide. The film thickness as measured with an ellipsometer was 40 nm. As a result of elemental analysis, the ratio Ta/Al/C was 75/22/3 (wt %). As a result of FT-IR measurement of the passivation film, a slight peak derived from an alkyl group was observed at approximately 1,200 cm$^{-1}$.

Subsequently, a capacitor having a MIS (metal-insulator-semiconductor) structure was prepared by forming plural aluminum electrodes having a diameter of 1 mm on the passivation film by vapor deposition through a metal mask. The voltage dependency of electrostatic capacitance (C-V property) of the capacitor was measured with a commercially available prober and a commercially available LCR meter (Hewlett-Packard Company, 4275A). As a result, it was found that the flat band voltage (Vfb) shifted from the ideal value of −0.81 V to −0.30 V. From this amount of shift, it was found that the passivation film obtained from passivation material (d2-1) exhibited a negative fixed charge at a fixed charge density (Nf) of $-6.2 \times 10^{10}$ cm$^{-2}$.

In the same manner as the above, passivation material (d2-1) was applied on both sides of an 8-inch p-type silicon substrate, and the silicon substrate was pre-baked and subjected to thermal treatment (sintering) under a nitrogen atmosphere at 600° C. for an hour, thereby preparing a sample of a silicon substrate having both sides covered with a passivation film. The carrier lifetime of the sample was measured with a lifetime measurement device (Kobelco Research Institute Inc., RTA-540). As a result, the carrier lifetime was 610 μs. For comparison the carrier lifetime of the same 8-inch p-type silicon substrate, which was passivated by an iodine passivation method, was measured. The result was 1,100 μs.

In view of the above, it was found that the passivation film obtained by performing thermal treatment to passivation material (d2-1) exhibited a certain level of passivation performance and a negative fixed charge.

Reference Example 2-7

As a compound from which tantalum oxide ($Ta_2O_5$) is obtained upon thermal treatment (sintering), 1.18 g (0.005 mol) of a commercially available tantalum (V) methoxide (structural formula: $Ta(OCH_3)_5$, molecular weight: 336.12), as a compound from which aluminum oxide ($Al_2O_3$) is obtained upon thermal treatment (sintering), 1.02 g (0.005 mol) of a commercially available aluminum triisopropoxide (structural formula: $Al(OCH(CH_3)_2)_3$, molecular weight: 204.25), and 10 g of a novolac resin were dissolved in a mixture of 10 g of diethyleneglycol monobutyl ether acetate and 10 g of cyclohexane, thereby preparing passivation material (d2-2).

Passivation material (d2-2) was applied by spin coating on one side of a p-type silicon substrate (from 8 Ω·cm to 12 Ω·cm) having a size of 8 inches and 725 μm in thickness, from which a spontaneously oxidized film had been previously removed with hydrofluoric acid at 0.49% by mass concentration. The silicon substrate was pre-baked on a hot plate at 120° C. for 3 minutes. Subsequently, thermal treatment was performed under a nitrogen atmosphere at 650° C. for an hour, thereby obtaining a passivation film including aluminum oxide and tantalum oxide. The film thickness as measured with an ellipsometer was 18 nm. As a result of elemental analysis, it was found that the ratio Ta/Al/C was 72/20/8 (wt %). As a result of FT-IR measurement of the passivation film, a slight peak derived from an alkyl group was observed at approximately 1,200 $cm^{-1}$.

Subsequently, a capacitor having a MIS (metal-insulator-semiconductor) structure was prepared by forming plural aluminum electrodes having a diameter of 1 mm on the passivation film though a metal mask. The voltage dependency of electrostatic capacitance (C-V property) of the capacitor was measured with a commercially available prober and a commercially available LCR meter (Hewlett-Packard Company, 4275A). As a result, it was found that the flat band voltage (Vfb) shifted from the ideal value of −0.81 V to −0.43 V. From this amount of shift, it was found that the passivation film obtained from passivation material (d-2) exhibited a negative fixed charge at a fixed charge density (Nf) of $-5.5 \times 10^{10}$ $cm^{-2}$.

In the same manner as the above, passivation material (d2-2) was applied on both sides of an 8-inch p-type silicon substrate. The silicon substrate was pre-baked and subjected to thermal treatment (sintering) under a nitrogen atmosphere at 600° C. for an hour, thereby preparing a sample of a silicon substrate having both sides covered with a passivation film. The carrier lifetime of the sample was measured with a lifetime measurement device (Kobelco Research Institute Inc., RTA-540). As a result, the carrier lifetime was 250 μs. For comparison, the carrier lifetime of the same 8-inch p-type silicon substrate, which was passivated by an iodine passivation method, was measured. The result was 1,100 μs.

In view of the above, it was found that the passivation film obtained by performing thermal treatment (sintering) of passivation material (d2-2) exhibited a certain level of passivation performance and a negative fixed charge.

<Combination Use of Two or More Vanadium-Group Element Oxides>

Reference Example 2-8

A commercially available organic metal film application material [Kojundo Chemical Lab. Co., Ltd., SYM-AL04, concentration: 2.3% by mass] from which aluminum oxide ($Al_2O_3$) is obtained upon thermal treatment (sintering), a commercially available organic metal film application material [Kojundo Chemical Lab. Co., Ltd., V-02, concentration: 2% by mass] from which vanadium oxide ($V_2O_5$) is obtained upon thermal treatment (sintering) and a commercially available organic metal film application material [Kojundo Chemical Lab. Co., Ltd., Ta-10-P, concentration: 10% by mass] from which tantalum oxide ($Ta_2O_5$) is obtained upon thermal treatment (sintering) were mixed to produce passivation material (e2-1) as an application material (see Table 9).

A commercially available organic metal film application material [Kojundo Chemical Lab. Co., Ltd., SYM-AL04, concentration: 2.3% by mass] from which aluminum oxide ($Al_2O_3$) is obtained upon thermal treatment (sintering), a commercially available organic metal film application material [Kojundo Chemical Lab. Co., Ltd., V-02, concentration: 2% by mass] from which vanadium oxide ($V_2O_5$) is obtained upon thermal treatment (sintering) and a commercially available organic metal film application material [Kojundo Chemical Lab. Co., Ltd., Nb-05, concentration: 5% by mass] from which niobium oxide ($Nb_2O_5$) is obtained upon thermal treatment (sintering) were mixed, thereby preparing passivation material (e2-2) as an application material (see Table 9).

A commercially available organic metal film application material [Kojundo Chemical Lab. Co., Ltd., SYM-AL04, concentration: 2.3% by mass] from which aluminum oxide ($Al_2O_3$) is obtained upon thermal treatment (sintering), a commercially available organic metal film application material [Kojundo Chemical Lab. Co., Ltd., Ta-10-P, concentration: 10% by mass] from which tantalum oxide ($Ta_2O_5$) is obtained upon thermal treatment (sintering) and a commercially available organic metal film application material [Kojundo Chemical Lab. Co., Ltd., Nb-05, concentration: 5% by mass] from which niobium oxide ($Nb_2O_5$) is obtained upon thermal treatment (sintering) were mixed, thereby preparing a passivation material (e2-3) as an application material (see Table 9).

A commercially available organic metal film application material [Kojundo Chemical Lab. Co., Ltd., SYM-AL04, concentration: 2.3% by mass] from which aluminum oxide ($Al_2O_3$) is obtained upon thermal treatment (sintering), a commercially available organic metal film application material [Kojundo Chemical Lab. Co., Ltd., V-02, concentration: 2% by mass] from which vanadium oxide ($V_2O_5$) is obtained upon thermal treatment (sintering), a commercially available organic metal film application material [Kojundo Chemical Lab. Co., Ltd., Ta-10-P, concentration: 10% by mass] from which tantalum oxide ($Ta_2O_5$) is obtained upon thermal treatment (sintering) and a commercially available organic metal film application material [Kojundo Chemical Lab. Co., Ltd., Nb-05, concentration: 5% by mass] from which niobium oxide ($Nb_2O_5$) is obtained upon thermal treatment (sintering) were mixed, thereby preparing passivation material (e2-4) as an application material (see Table 9).

In the same manner as Reference Example 2-1, each of passivation materials (e2-1) to (e2-4) was applied by spin coating on one side of a p-type silicon substrate (from 8μ·cm to 12 Ω·cm) having a size of 8 inches and 725 μm in thickness from which a spontaneously oxidized film had been removed with hydrofluoric acid at a concentration of 0.49% by mass, and the silicon substrate was pre-baked on a hot plate at 120° C. for 3 minutes. Subsequently, the silicon substrate was subjected to thermal treatment (sintering) under a nitrogen atmosphere at 650° C. for an hour, thereby obtaining a passivation film including aluminum oxide and two or more kinds of vanadium-group element oxides.

With the passivation film obtained above, the voltage dependency of electrostatic capacitance was measured and the fixed charge density was calculated therefrom.

Subsequently, each of passivation materials (e2-1) to (e2-4) was applied on both sides of a 8-inch p-type silicon substrate, and the silicon substrate was pre-baked and subjected to thermal treatment (sintering) under a nitrogen atmosphere at 650° C. for an hour, thereby preparing a sample of a silicon substrate having both sides covered with a passivation film. The carrier lifetime of the sample was measured with a lifetime measurement device (Kobelco Research Institute Inc., RTA-540).

The results are shown in Table 9.

All of the passivation films obtained from passivation materials (e2-1) to (e2) exhibited a negative fixed charge after performing thermal treatment (sintering) and a certain degree of carrier lifetime, although the results were different depending on the ratio (mass ratio) of the two or more kinds of vanadium-group element oxides to aluminum oxide after the thermal treatment (burning), suggesting that they can function as a passivation film.

vation materials (f2-1) to (f2-8) as an application material (see Table 10).

Further, passivation material (f2-9) in which aluminum oxide was used alone was prepared (see Table 10).

In the same manner as Reference Example 2-1, each of passivation materials (f2-1) to (f2-9) was applied on one side of a p-type silicon substrate, and the silicon substrate was subjected to thermal treatment (sintering) to prepare a passivation film. With the passivation film, the voltage dependency of electrostatic capacitance was measured and the fixed charge density was calculated therefrom.

Further, in the same manner as Reference Example 2-1, each of passivation materials (f2-1) to (f2-9) was applied on both sides of a p-type silicon substrate, and the silicon substrate was subjected to thermal treatment (sintering), thereby preparing a sample. The carrier lifetime of the sample was measured, and the results are shown in Table 10.

As shown in Table 10, the cases in which aluminum oxide/vanadium oxide or tantalum oxide of the passivation material is 90/10 and 80/20, there was a significant variability among fixed charge density values, and a negative fixed charge density could not be obtained in a stable manner. However, it was determined that a negative fixed charge density could be attained by using aluminum oxide and niobium oxide. When the measurement was performed by a CV method in the cases in which aluminum oxide/vanadium oxide or tantalum oxide of the passivation material was 90/10 and 80/20 by a CV method, the passivation film exhibited a positive fixed charge in some cases and did not exhibit a negative fixed charge in a stable manner. A passivation film that exhibits a positive fixed charge can be used as a passivation film for an n-type silicon substrate. On the other hand, a negative fixed charge density could not be obtained with passivation material (f2-9) including 100% by mass of aluminum oxide.

TABLE 9

| | Mass Ratio of Metal Oxide after Thermal treatment | | | | Film thickness after Thermal | Fixed Charge | Carrier |
|---|---|---|---|---|---|---|---|
| | $Al_2O_3$ | $V_2O_5$ | $Ta_2O_5$ | $Nb_2O_5$ | treatment (nm) | Density ($cm^{-2}$) | Lifetime (μs) |
| e2-1 | 30 | 40 | 30 | 0 | 55 | $-3.1 \times 10^{11}$ | 480 |
| e2-2 | 30 | 35 | 0 | 35 | 50 | $-8.2 \times 10^{11}$ | 440 |
| e2-3 | 30 | 0 | 30 | 40 | 41 | $-4.3 \times 10^{11}$ | 510 |
| e2-4 | 30 | 20 | 20 | 20 | 45 | $-6.5 \times 10^{11}$ | 450 |

Reference Example 2-9

In the same manner as Reference Example 2-1, a commercially available organic metal film application material [Kojundo Chemical Lab. Co., Ltd., SYM-AL04, concentration: 2.3% by mass] from which aluminum oxide ($Al_2O_3$) is obtained upon thermal treatment (sintering), a commercially available organic metal film application material [Kojundo Chemical Lab. Co., Ltd., V-02, concentration: 2% by mass] from which vanadium oxide ($V_2O_5$) is obtained upon thermal treatment (sintering) and a commercially available organic metal film application material [Kojundo Chemical Lab. Co., Ltd., Ta-10-P, concentration; 10% by mass] from which tantalum oxide ($Ta_2O_5$) is obtained upon thermal treatment (sintering) were mixed, thereby preparing passi-

TABLE 10

| | Mass Ratio of Metal Oxide after Thermal treatment | | | Film Thickness after Thermal treatment | Fixed Charge | Carrier Lifetime |
|---|---|---|---|---|---|---|
| | $Al_2O_3$ | $V_2O_5$ | $Ta_2O_5$ | (nm) | Density ($cm^{-2}$) | (μs) |
| f2-1 | 90 | 10 | 0 | 55 | $2.1 \times 10^{11}$ | 600 |
| f2-2 | 80 | 20 | 0 | 50 | $1.9 \times 10^{11}$ | 590 |
| f2-3 | 90 | 0 | 10 | 41 | $2.3 \times 10^{11}$ | 610 |
| f2-4 | 80 | 0 | 20 | 45 | $2.1 \times 10^{11}$ | 570 |
| f2-5 | 90 | 10 | 0 | 48 | $-7.8 \times 10^{9}$ | 580 |
| f2-6 | 80 | 20 | 0 | 52 | $-8.3 \times 10^{9}$ | 480 |
| f2-7 | 90 | 0 | 10 | 46 | $-1.3 \times 10^{10}$ | 560 |

TABLE 10-continued

| | Mass Ratio of Metal Oxide after Thermal treatment | | | Film Thickness after Thermal treatment (nm) | Fixed Charge Density (cm$^{-2}$) | Carrier Lifetime (μs) |
|---|---|---|---|---|---|---|
| | Al$_2$O$_3$ | V$_2$O$_5$ | Ta$_2$O$_5$ | | | |
| f2-8 | 80 | 0 | 20 | 56 | −9.6 × 10$^9$ | 490 |
| f2-9 | 100 | 0 | 0 | 34 | 2.2 × 10$^{11}$ | 600 |

Reference Example 2-10

A photovoltaic cell element having a structure shown in FIG. 14 was prepared by using as silicon substrate 101, a monocrystalline silicon substrate doped with boron. The surface of silicon substrate 101 was subjected to texture processing, and an application-type phosphorus diffusion material was applied only onto a light receiving surface, and diffusion layer 102 (a phosphorus diffusion layer) was formed by performing thermal treatment. Thereafter, the application-type phosphorus diffusion material was removed with dilute hydrofluoric acid.

Subsequently, at the light receiving surface side, a SiN film was formed by plasma CVD as light receiving surface anti-reflection film 103. Then, passivation material (a2-1) as prepared in Reference Example 2-1 was applied by an ink jet method to a region excluding a contact region (opening OA) at the back surface side of silicon substrate 101. Thereafter, thermal treatment was performed to form passivation film 107 having opening OA. A sample in which passivation film 107 was formed from passivation material (c2-1) as prepared in Reference Example 2-5 was also prepared.

Subsequently, a paste mainly composed of silver was applied by screen printing in the form of predetermined finger electrodes and bus bar electrodes, on light receiving surface anti-reflection film 103 (SiN film) formed on the light receiving surface of silicon substrate 101. At the back surface side, a paste mainly composed of aluminum was applied by screen printing on an entire surface. Thereafter, thermal treatment (fire through) was performed at 850° C. to form an electrode (first electrode 105 and second electrode 106), and BSF layer 104 was formed by allowing aluminum to diffuse in opening OA, thereby forming a photovoltaic cell element having a structure shown in FIG. 14.

Although the method of forming a silver electrode at the light receiving surface as described herein includes a fire-through process without forming an opening to the SiN film, it is also possible to form a silver electrode by a method in which opening OA is formed to the SiN film by etching or the like, and subsequently the silver electrode is formed.

Figure 11:
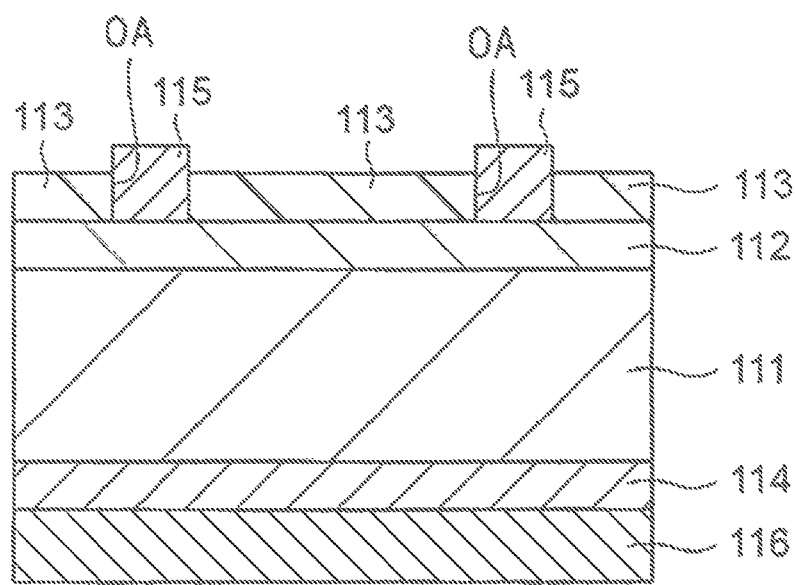
FIG. 11 is a cross sectional view showing a structure of a double-sided electrode type photovoltaic cell element.

For comparison, a photovoltaic cell element having a structure shown in FIG. 11 was prepared by a method as described above, except that passivation film 107 was not formed and an aluminum paste was applied on an entire region of the back surface, and p$^+$ layer 114 corresponding to BSF layer 104 and electrode 116 corresponding to the second electrode were formed on the entire region of the back surface. With these photovoltaic cell elements, characterization (short-circuit current, open-voltage, fill factor and conversion efficiency) was performed. The characterization was performed according to JIS-C-8913 (2005) and JIS-C-8914 (2005). The results are shown in Table 11.

From the results shown in Table 11, it was found that the photovoltaic cell element having passivation film 107 exhibited an increase in short-circuit current and open voltage, as compared with a photovoltaic cell element not having passivation film 107. In addition, it was found that the photovoltaic cell element having passivation film 107 exhibited an improved conversion efficiency (incident photon-to-current conversion efficiency) by up to 0.6%.

TABLE 11

| Passivation Film | Short-Circuit Current (mA/cm$^2$) | Open Voltage (V) | Fill Factor | Conversion Efficiency (%) |
|---|---|---|---|---|
| a2-1 | 33.3 | 0.623 | 0.798 | 16.6 |
| c2-1 | 33.2 | 0.620 | 0.799 | 16.4 |
| None | 32.8 | 0.610 | 0.800 | 16.0 |

The disclosures of Japanese Patent Application Publication Nos. 2012-160336, 2012-218389, 2013-011934 and 2013-040153 are incorporated herein by reference in their entirety. All literatures, patent applications, and technical standards described in this specification are incorporated herein by reference to the same extent as if each individual literature, patent application and technical standard were specifically and individually indicated as being incorporated by reference.

The invention claimed is:

1. A composition for forming a passivation layer, comprising a compound represented by the following Formula (I) and a compound represented by the following Formula (II):

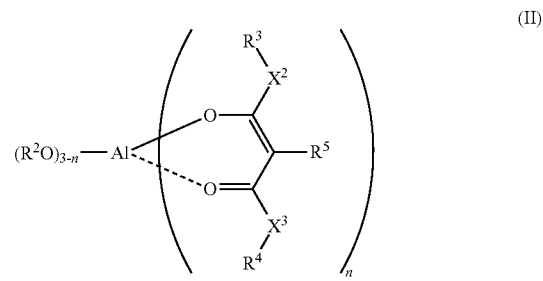

wherein, in Formula (I) and Formula (II),

M comprises at least one metal element selected from the group consisting of Nb, Ta, V, Y and Hf, each R$^1$ independently represents an alkyl group having from 1 to 8 carbon atoms or an aryl group having from 6 to 14 carbon atoms, m represents an integer from 1 to 5, each R$^2$ independently represents an alkyl group having from 1 to 8 carbon atoms, n represents an integer from 1 to 3, each of X$^2$ and X$^3$ independently represents an oxygen atom or a methylene group, and each of R$^3$, R$^4$ and R$^5$ independently represents a hydrogen atom or an alkyl group having from 1 to 8 carbon atoms, wherein the weight/weight ratio of the compound represented by Formula (I) and the compound represented by Formula (II) is from 50/50 to 90/10 and having a fixed charge density of from −7.8×10$^9$ to −8.3×10$^{11}$.

2. The composition for forming a passivation layer according to claim 1, further comprising a liquid medium.

3. The composition for forming a passivation layer according to claim 1, further comprising a resin.

4. The composition for forming a passivation layer according to claim 3, wherein the composition further comprising a liquid medium, and a total content of the liquid medium and the resin being from 5% by mass to 98% by mass based on the total content of the composition.

5. The composition for forming a passivation layer according to claim 1, wherein a total content of the compound represented by Formula (I) and the compound represented by Formula (II) being from 0.1% by mass to 80% by mass based on the total content of the composition.

6. A semiconductor substrate having a passivation layer, comprising:
   the semiconductor substrate; and
   the passivation layer that is a thermally-treated product of the composition for forming a passivation layer according to claim 1 that is provided at an entire or partial surface of the semiconductor substrate.

7. A photovoltaic cell element, comprising:
   a semiconductor substrate having a pn junction of a p-type layer and an n-type layer;
   a passivation layer that is a thermally-treated product of the composition for forming a passivation layer according to claim 1 and that is provided at an entire or partial surface of the semiconductor substrate; and
   an electrode provided at at least one of the p-type layer or the n-type layer.

8. A photovoltaic cell, comprising;
   the photovoltaic cell element according to claim 7; and
   a wiring material provided on the electrode of the photovoltaic cell element.

* * * * *